United States Patent
Kumar et al.

(10) Patent No.: US 8,741,932 B2
(45) Date of Patent: Jun. 3, 2014

(54) IMIDAZOPYRIDINE DERIVATIVES

(75) Inventors: Sanjay Kumar, Mumbai (IN);
Sivaramakrishnan Hariharan, Mumbai (IN); Mandar Bhonde, Pune (IN); Nilesh Dagia, Mumbai (IN); Rajiv Sharma, Mumbai (IN); Pallavi Hanmantrao Mane, Mumbai (IN); Pramod Bhaskar Kumar, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 13/508,135

(22) PCT Filed: Nov. 4, 2010

(86) PCT No.: PCT/IB2010/054996
§ 371 (c)(1),
(2), (4) Date: May 4, 2012

(87) PCT Pub. No.: WO2011/055320
PCT Pub. Date: May 12, 2011

(65) Prior Publication Data
US 2012/0232072 A1 Sep. 13, 2012

Related U.S. Application Data

(60) Provisional application No. 61/258,685, filed on Nov. 6, 2009.

(51) Int. Cl.
*A01N 43/40* (2006.01)
*A61K 31/44* (2006.01)
*A01N 43/54* (2006.01)
*A61K 31/535* (2006.01)
*C07D 491/02* (2006.01)
*C07D 265/36* (2006.01)
*C07D 498/02* (2006.01)
*C07D 413/00* (2006.01)

(52) U.S. Cl.
USPC ..... 514/333; 514/233.2; 514/256; 514/230.5; 546/121; 544/127; 544/105

(58) Field of Classification Search
USPC ............ 546/121; 514/300, 233.2, 256, 230.5; 544/127, 105, 333
See application file for complete search history.

(56) References Cited

U.S. PATENT DOCUMENTS 6,403,588 B1  6/2002 Hayakawa et al.

FOREIGN PATENT DOCUMENTS

WO  2004/017950 A2  3/2004

OTHER PUBLICATIONS

Jose et al., The Oncologist (2011), 16 (suppl 1): 12-19.*
Almirante et al., Journal of medicinal chemistry (1970), 13(6), pp. 1048-1051.*
Wullschleger, Stephan, et al., "TOR Signaling in Growth and Metabolism", Cell 124, Feb. 10, 2006, pp. 471-484.
Hennessy, Bryan T., et al., "Exploiting the P13K/AKT Pathway for Cancer Drug Discovery", Nature Reviews Drug Discovery, Dec. 2005, vol. 4, pp. 988-1004.
Maier, Gerhard, et al., "Absence of tumor growth stimulation in a panel of 16 human tumor cell lines by mistletoe extracts in vitro", Anti-Cancer Drugs, 2002, vol. 13, pp. 1-7.
Jansky, L., et al., "Dynamics of Cytokine Production in Human Peripheral Blood Mononuclear Cells Stimulated by LPS or Infected by *Borrelia*", Physiol. Res. 52, 2003, pp. 593-598.
Bhonde, Mandar R., et al., "A novel mTOR inhibitor is efficacious in a murine model of colitis", Am J Physiol Gastrointest Liver Physiol 295, Oct. 15, 2008, pp. G1237-G1245.
Brennan, Fionula M., et al., "Inhibitory Effect of TNFα Antibodies on Synovial Cell Interleukin-1 Production in Rheumatoid Arthritis" The Lancet, Jul. 29, 1989, pp. 244-247.
Versteeg, Henri H., et al., "A new phosphospecific cell-based ELISA for p42/p44 mitogen-activated protein kinase (MAPK), p38 MAPK, protein kinase B and cAMP-response-element-binding protein", Biochem J 350, 2000, pp. 717-722.
Knight, Zachcary A., et al., "A Pharmacological Map of the P13-K Family Defines a Role for p110α in Insulin Signaling", Cell 125, May 19, 2006, pp. 733-747.
Liu, Pixu, et al. Targeting the phosphoinositide 3-kinase pathway in cancer. Nature Reviews/Drug Discovery, vol. 8, pp. 627-644. Aug. 2009.
Bradley, J.R. TNF-mediated inflammatory disease. Journal of Pathology vol. 214. pp. 149-160. Aug. 2008.
Grunke, M., et al. Successful treatment of inflammatory knee osteoarthritis with tumour necrosis factor blockade. Ann Rheum Dis. vol. 65, p. 555. 2006.

(Continued)

*Primary Examiner* — Niloofar Rahmani
(74) *Attorney, Agent, or Firm* — Ladas & Parry LLP

(57) ABSTRACT

The present invention relates to compounds of formula (I),

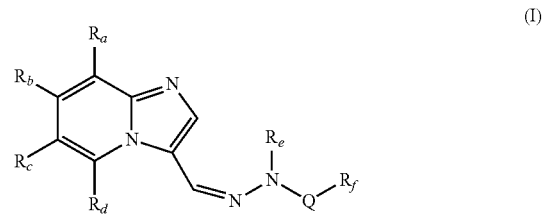

wherein $R_a$, $R_b$, $R_c$, $R_d$, $R_e$ and $R_f$ are as defined in the specification, processes for their preparation, pharmaceutical compositions containing them and their use in the treatment of diseases mediated by phosphatidylinositol-3-kinase (PI3K), mammalian target of rapamycin (mTOR), Signal transducer and activator of transcription 3 (STAT 3), tumor necrosis factor-α (TNF-α), interleukin-6 (IL-6) or a combination thereof particularly in the treatment of cancer and inflammation.

18 Claims, 1 Drawing Sheet

(56) References Cited

OTHER PUBLICATIONS

McMachon, Mark S., et al. Does Anti-TNF-Alpha Have a Role in the Treatment of Osteoporosis? Bulletin of the NYU Hospital for Joint Diseases. vol. 66(4), pp. 280-281. 2008.

Abstract of: Sands, Bruce E., al. The Role of TNFa in Ulcerative Colitis. Journal of Clinical Pharmacology, vol. 74, Issue 8, pp. 930-941. Aug. 2007.

Chang, F. et al., Involvement of P13K/Akt pathway in cell cycle progression, apoptosis, and neoplastic transformation: a target for cancer chemotherapy. Leukemia 2003, 17, 590-603.

Yuan, TL, et al., P13K pathway alterations in cancer/variations on a theme. Oncogene, 2008, 27(41), 5497-5510.

Raynaud, Florence I. et al, Biological properties of potent inhibitors of class I phosphatidylinositide 3-kinases; from PI-103 through PI-540k, PI 620 to the oral agent GCD-0941, Molecular Cancer Therapeutics, 2009 8(7), 1725-1738.

Serra, Violeta, et al, NVP-BEZ235, a Dual PI3K/mTOR Inhibitor, Prevents PI3K Signaling and Inhibits the Growth of Cancer Cells with Activating P13K Mutations. Cancer Research, 2008,68 (19), 8022-8030.

Brachmann, Saskia M., et al, Specific apoptosis induction by the dual PI3K/mTor inhibitor NVP-BEZ235 in HER 2 amplified and PIK3CA mutant breast cells. Proceedings of the National Academy of Sciences, 2009, 106 (52), 22299-22304.

Cao. P. et al, Activity of a novel, dual PI3-kinase/mTor inhibitor NVP-BEZ235 against primary human pancreatic cancers grown as orthotopic xenografts. British Journal of Cancer. 2009, 100, 1267-1276.

* cited by examiner

N : Naive Mice
D : DSS Fed Mice
A : 5-ASA Treated (25mg/kg/day, p.o) DSS Fed Mice
E : Compound of Example 25 Treated (10 mg/kg/day, p.o) DSS Fed Mice

IMIDAZOPYRIDINE DERIVATIVES

This is a 371 application of PCT/IN2010/054996 filed on 4 Nov. 2010, entitled "IMIDAZOPYRIDINE DERIVATIVES", which was published in the English language on 12 May 2011, with International Publication Number WO 2011/055320A1, and which claims priority from U.S. patent application 61/258,68 5filed 6 Nov. 2009, the content of which is incorporated herein by reference.

FIELD OF THE INVENTION

The present invention relates to imidazo[1,2-a]pyridine derivatives, processes for their preparation, pharmaceutical compositions containing them and their use in the treatment of diseases mediated by phosphatidylinositol-3-kinase (PI3K), mammalian target of rapamycin (mTOR), Signal transducer and activator of transcription 3 (STAT 3), tumor necrosis factor-α (TNF-α), interleukin-6 (IL-6) or a combination thereof. In particular these compounds can be used in the treatment of cancer and inflammation.

BACKGROUND OF THE INVENTION

Cancer can be defined as an abnormal growth of tissues characterized by a loss of cellular differentiation.

The phosphatidylinositol-3-kinase (PI3K) pathway plays an important role in cellular signaling. Phosphatidylinositol-3-kinases or phosphoinositol-3-kinases (PI3-kinases or PI3 Ks) are a family of related enzymes that are capable of phosphorylating the 3 position hydroxyl group of the inositol ring of phosphatidylinositol. The PI3K family is composed of Class I, II and Class III. The classification is based on primary structure, regulation and in vitro lipid substrate specificity. Class III PI3K enzymes phosphorylate PI alone while, Class II PI3K enzymes phosphorylate both PI and PI 4-phosphate [PI(4)P].

Class I PI3K enzymes phosphorylate PI, PI(4)P and PI 4,5-biphosphate[PI(4,5)$P_2$]. Class I PI3Ks are further divided into two groups, class Ia and class Ib, in terms of their activation mechanism. Class Ia PI3Ks include PI3K p110α, p110β and p110δ subtypes and are generally activated in response to growth factor-stimulation of receptor tyrosine kinases. The first two p110 isoforms (α and β) are expressed in all cells, but p110δ is primarily expressed in leukocytes. Class Ib enzymes consist of p110γ catalytic subunit that interacts with a p110 regulatory subunit. It is activated in response to G-protein coupled receptor systems and its expression appears to be limited to leukocytes and cardiomyocytes. Class Ia subtypes are considered to be associated with cell proliferation and carcinogenesis.

mTOR is a class IV PI-3 kinase family member with protein kinase activity, but lacks any lipid kinase activity. It regulates cell growth and metabolism in response to environmental cue hence inhibitors of mTOR may be useful in the treatment of cancer and metabolic disorders (Cell, 2006, 124, 471-484).

PI3K mediated signaling pathway plays a very important role in cancer cell survival, cell proliferation, angiogenesis and metastasis. The PI3K pathway is activated by stimuli such as growth factors, hormones, cytokines, chemokines and hypoxic stress. Activation of PI3K results in the recruitment and activation of protein kinase B (AKT) to the membrane, which gets phosphorylated at Serine 473 (Ser-473). Thus, phosphorylation of Ser-473 of AKT is a read-out/detector for the activation of the PI3K-mediated pathway. A cell-based ELISA technique can be used to study such activation.

AKT is known to positively regulate cell growth (accumulation of cell mass) by activating the mTOR serine threonine kinase. mTOR serves as a molecular sensor that regulates protein synthesis on the basis of nutrients. mTOR regulates biogenesis by phosphorylating and activating p70S6 kinase (S6K1), which in turn enhances translation of mRNAs that have polypyrimidine tracts. The phosphorylation status of S6K1 is a bonafide read-out of mTOR function.

Most tumors have an aberrant PI3K pathway (Nat. Rev. Drug Discov., 2005, 4, 988-1004). Since mTOR lies immediately downstream of PI3K, these tumors also have hyperactive mTOR function. Thus, most of the cancer types can be treated using the molecules that target PI3K and mTOR pathways.

The compounds that are PI3K and/or mTOR and/or STAT3 inhibitors, find use in the treatment of cancers. Compounds are used to reduce, inhibit, or diminish the proliferation of tumor cells, and thereby assist in reducing the size of a tumor.

Signal transducer and activator of transcription 3 also known as STAT3 is a transcription factor which in humans is encoded by the STAT3 gene. The protein encoded by this gene is a member of the STAT protein family. In response to cytokines and growth factors, STAT family members are phosphorylated by the receptor associated kinases, and then form homo- or heterodimers that translocate to the cell nucleus where they act as transcription activators. STAT3 mediates the expression of a variety of genes in response to cell stimuli, and thus plays a key role in many cellular processes such as cell growth and apoptosis. Constitutive STAT3 activation is associated with various human cancers and commonly suggests poor prognosis. It has anti-apoptotic as well as proliferative effects.

The compounds that are STAT3 inhibitors, find use in the treatment of cancers. These compounds are used to reduce, inhibit, or diminish the proliferation of tumor cells.

SF 1126 (Semaphore, Inc.) is a pan-PI3K inhibitor in phase I clinical trials. SF1126 is a covalent conjugate of LY294002 containing a peptide-based targeting group.

GDC-0941 (Piramed Ltd. and Genentech, Inc.) is a PI3K inhibitor and is in phase I clinical trials.

BEZ-235 (Novartis AG), which is currently in phase I/II clinical trials, inhibits all isoforms of PI3K and also inhibits the kinase activity of mTOR.

XL-765 (Exelixis Inc.) is also a dual inhibitor of mTOR and PI3K. The compound is in phase I clinical trials as an oral treatment for solid tumors.

PIK-75 (Astellas Pharma Inc.) is in preclinical studies. It is a PI3Kalpha inhibitor and inhibits p110α>200 fold more than plifβ.

Inflammation is the response of a tissue to injury that may be caused by a biological assault such as invading organisms and parasites, ischemia, antigen-antibody reactions or other forms of physical or chemical injury. It is characterized by increased blood flow to the tissue, causing pyrexia, erythema, induration and pain.

Several proinflammatory cytokines, especially TNF-α and interleukins (IL-1β, IL-6, IL-8) play an important role in the inflammatory process. Both IL-1 and TNF-α are derived from mononuclear cells and macrophages and in turn induce the expression of a variety of genes that contribute to the inflammatory process. An increase in TNF-α synthesis/release is a common phenomenon during the inflammatory process. Inflammation is an inherent part of various disease states like rheumatoid arthritis, Crohn's disease, ulcerative colitis, septic shock syndrome, psoriasis, atherosclerosis, among other clinical conditions.

The first line of treatment for inflammatory disorders involves the use of non-steroidal anti-inflammatory drugs (NSAIDs) e.g. ibuprofen, naproxen to alleviate symptoms such as pain. However, despite the widespread use of NSAIDs, many individuals cannot tolerate the doses necessary to treat the disorder over a prolonged period of time as NSAIDs are known to cause gastric erosions. Moreover, NSAIDs merely treat the symptoms of disorder and not the cause. When patients fail to respond to NSAIDs, other drugs such as methotrexate, gold salts, D-penicillamine and corticosteroids are used. These drugs also have significant toxic effects.

Monoclonal antibody drugs such as Infliximab, Etanercept and Adalimumab are useful as anti-inflammatory agents, but have drawbacks such as route of administration (only parenteral), high cost, allergy induction, activation of latent tuberculosis, increased risk of cancer and congestive heart disease.

PI3K inhibitors are known in the art. For example, U.S. Pat. No. 6,403,588 describes phosphatidylinositol 3 kinase inhibitors useful as antitumor agents. Additionally, WO 2004/017950 describes phosphatidylinositol 3,5-biphosphate inhibitors as anti-viral agents.

SUMMARY OF THE INVENTION

The present invention provides imidazo[1,2-a]pyridine derivatives of formula (I):

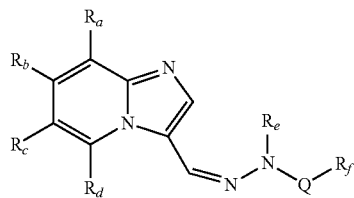

in all their stereoisomeric and tautomeric forms and mixtures thereof in all ratios, prodrugs, N-oxides, and their pharmaceutically acceptable salts and pharmaceutically acceptable solvates,
wherein,
$R_a$, $R_b$ and $R_d$ are independently selected from hydrogen, hydroxy, halogen, cyano, nitro, —$COR_1$, —$COOR_1$, —$CONH_2$, —$NR_1R_2$, —$C_1$-$C_8$ alkyl, halo-$C_1$-$C_8$ alkyl and —$C_1$-$C_8$ alkoxy;
$R_c$ is halogen or heteroaryl;
$R_e$ is hydrogen, —$C_1$-$C_8$ alkyl, —$C_6$-$C_{14}$ aryl or heteroaryl;
Q is —$SO_2$—, —C(O)$NR_1$— or —C(S)$NR_1$—;
$R_f$ is —$C_1$-$C_8$ alkyl, —$(CR_1R_2)_p$—$C_3$-$C_8$ cycloalkyl, —$(CR_1R_2)_p$—$C_6$-$C_{14}$ aryl, —$(CR_1R_2)_p$-heterocyclyl, —$(CR_1R_2)_p$-heteroaryl, —$C_3$-$C_8$cycloalkyl, —$C_6$-$C_{14}$aryl, heteroaryl or heterocyclyl;
$R_1$ and $R_2$ are independently selected from hydrogen and lower alkyl;
p is independently an integer from 1 to 3;
with the proviso that when Q is —$SO_2$—, then $R_c$ is not halogen;
wherein each of the above alkyl, haloalkyl, alkoxy, cycloalkyl, aryl, heteroaryl and heterocyclyl are unsubstituted or substituted with one or more of the same or different groups selected from halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo-$C_1$-$C_6$ alkyl, halo-$C_1$-$C_6$ alkoxy, —$C_1$-$C_6$ alkoxy, haloalkoxy, —$C_3$-$C_8$ cycloalkyl, —$(CR_1R_2)_p$-aryl, —$C_6$-$C_{10}$ aryl, —NHCOMe, —$S(O)_2$Me, aryloxy, heterocyclyl and heteroaryl.

The present invention also provides processes for producing compounds of formula (I).

The present invention further provides a pharmaceutical composition comprising a therapeutically effective amount of a compound of formula (I) or a pharmaceutically acceptable salt thereof, or a pharmaceutically acceptable solvate thereof, in combination with a pharmaceutically acceptable excipient, carrier or diluent.

The present invention also provides a method of treating diseases mediated by PI3K and/or mTOR and/or STAT3 in a mammal comprising administering to a mammal in need of such treatment an effective amount of a compound of formula (I) or a pharmaceutically acceptable salt thereof.

The present invention also provides a method of treating diseases mediated by TNF-α and/or IL-6 in a mammal comprising administering to a mammal in need of such treatment an effective amount of a compound of formula (I) or a pharmaceutically acceptable salt thereof.

The present invention also provides a method of inhibiting the tumor cell growth, tumor cell proliferation or tumorigenesis in a mammal comprising administering to a mammal in need of such treatment an effective amount of a compound of formula (I) or a pharmaceutically acceptable salt thereof.

The present invention also provides a method of treating cancer mediated by PI3K and/or mTOR and/or STAT3 comprising administering to a mammal in need of such treatment an effective amount of a compound of formula (I) or a pharmaceutically acceptable salt thereof.

The present invention further provides a method of treating cancer comprising administering to a mammal in need of such treatment an effective amount of a compound of formula (I) or a pharmaceutically acceptable salt thereof.

The present invention also provides a method of treating inflammatory conditions mediated by TNF-α and/or interleukin-6 (IL-6) comprising administering to a mammal in need of such treatment an effective amount of a compound of formula (I) or a pharmaceutically acceptable salt thereof.

The present invention further provides a method of treating inflammatory conditions comprising administering to a mammal in need of such treatment an effective amount of a compound of formula (I) or a pharmaceutically acceptable salt thereof.

The present invention further provides the use of a compound of formula (I) or a pharmaceutically acceptable salt thereof for the manufacture of a medicament containing either entity for the treatment of diseases mediated by PI3K and/or mTOR and/or STAT3.

The present invention further provides the use of a compound of formula (I) or a pharmaceutically acceptable salt thereof for the manufacture of a medicament containing either entity for the treatment of cancer.

The present invention further provides the use of a compound of formula (I) or a pharmaceutically acceptable salt thereof for the manufacture of a medicament containing either entity for the treatment of diseases mediated by TNF-α and/or IL-6.

The present invention further provides the use of a compound of formula (I) or a pharmaceutically acceptable salt thereof for the manufacture of a medicament containing either entity for the treatment of inflammatory conditions.

DETAILED DESCRIPTION OF THE INVENTION

Figure 1:
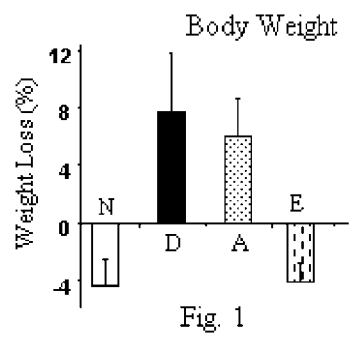
FIG. 1 is a graph depicting effect of compound of Example 25 on DSS induced weight loss (%) in C57BL/6J mice. 5-ASA was used as positive control

Listed below are definitions, which apply to the terms as they are used throughout the specification and the appended claims (unless they are otherwise limited in specific instances), either individually or as part of a larger group. It will be understood that "substitution" or "substituted with" includes the implicit proviso that such substitution is in accordance with permitted valence of the substituted atom and the substituent, as well as represents a stable compound, which does not readily undergo transformation such as by rearrangement, cyclization, elimination, etc.

As used herein, the term "alkyl" whether used alone or as part of a substituent group, refers to a saturated straight or branched chain hydrocarbon radical containing the indicated number of carbon atoms. For example, $C_1$-$C_8$ alkyl refers to alkyl group having 1 to 8 (both inclusive) carbon atoms. In case of absence of any numerical designation, "alkyl" is a straight or branched-chain containing from 1 to 6 (both inclusive) carbon atoms. Examples of alkyl include, but are not limited to, methyl, ethyl, n-propyl, n-butyl, n-pentyl, n-hexyl, n-heptyl, n-octyl, isopropyl, sec-butyl, isobutyl, tert-butyl, isopentyl, 2-methylbutyl and 3-methylbutyl.

As used herein, the term "lower alkyl" whether used alone or as part of a substituent group, refers to the radical of saturated aliphatic groups, including straight or branched chain containing from 1 to 4 carbon atoms, such as methyl, ethyl, n-propyl, isopropyl, n-butyl, sec-butyl, isobutyl and tert-butyl.

Unless stated otherwise, the alkyl and lower alkyl groups as stated above can be unsubstituted or substituted with one or more of the same or different groups selected from halogen, oxo, carbonyl, carboxy, cyano, thioester, sulfonyl, nitro, acyl, acyloxy, cycloalkyl, aryl, heterocyclyl, heteroaryl, —$OR_x$, —$SR_x$, —$NR_yR_z$, —$CONR_yR_z$, —$NR_yCOR_z$, —$NR_yCONR_yR_z$, —$NR_ySOR_z$, —$NR_ySO_2R_z$, —$S(O)_mR_y$ and —$S(O)_nNR_yR_z$, wherein $R_x$ is hydrogen, alkyl, cycloalkyl, aryl, heteroaryl or heterocyclyl; wherein $R_y$ and $R_z$ are independently selected from hydrogen, hydroxy, alkyl, alkoxy, alkenyl, alkynyl, cycloalkyl, aryl, aralkyl, heteroaryl and heterocyclyl; m is an integer from 0 to 2 and n is an integer from 0 to 1. Any kind of substituent present in substituted alkyl residues can be present in any desired position provided that the substitution does not lead to an unstable molecule.

As used herein, the term "alkenyl" whether used alone or as part of a substituent group, refers to a straight or branched chain hydrocarbon radical containing the indicated number of carbon atoms and at least one carbon-carbon double bond (two adjacent sp² carbon atoms). For example, $C_2$-$C_8$ alkenyl refers to an alkenyl group having 1 to 8 (both inclusive) carbon atoms. Depending on the placement of double bond and substituents if any, the geometry of the double bond may be entgegen (E), or zusammen (Z), cis or trans. Examples of alkenyl include, but are not limited to, vinyl and allyl. Unless stated otherwise, the alkenyl groups can be unsubstituted or substituted with one or more of the same or different groups selected from halogen, hydroxy, carboxy, acetoxy, amino, cyano, nitro, alkyl, alkoxy, cycloalkyl, aryloxy, aryl, aralkyl and heterocyclyl.

As used herein, the term "alkynyl" whether used alone or as part of a substituent group, refers to a straight or branched chain hydrocarbon radical containing the indicated number of carbon atoms and at least one carbon-carbon triple bond (two adjacent sp carbon atoms). For example, $C_2$-$C_8$ alkynyl refers to an alkynyl group having 1 to 8 (both inclusive) carbon atoms. Examples of alkynyl include, but are not limited to, ethynyl, 1-propynyl, 3-propynyl and 3-butynyl. Unless stated otherwise, the "alkynyl" may be unsubstituted or substituted with one or more of the same or different groups, selected from alkyl, halogen, hydroxy, carboxy, acetoxy, amino, cyano, nitro, cycloalkyl, alkoxy, aryloxy, aryl, aralkyl and heterocyclyl.

As used herein, the term "cycloalkyl" whether used alone or as part of a substituent group, refers to a saturated or partially unsaturated cyclic hydrocarbon radical including 1, 2 or 3 rings and including a total of 3 to 14 carbon atoms forming the rings. The term cycloalkyl includes bridged, fused and spiro ring systems. For example, $C_3$-$C_8$ cycloalkyl refers to a cycloalkyl group having 3 to 8 (both inclusive) carbon atoms. Examples of cycloalkyl include, but are not limited to, cyclopropyl, cyclobutyl, cyclopentyl, cyclohexyl, cyclopentene, adamantyl, norbornyl, bicyclo[2.1.0]pentane, bicyclo[2.2.1]heptyl, bicyclo[2.2.1]hept-2-ene, spiro[3.3] heptane and 1,2,3,3a-tetrahydropentalene. Unless stated otherwise, the "cycloalkyl" may be unsubstituted or substituted with one or more of the same or different groups selected from halogen, hydroxy, alkoxy, oxo, alkyl, cycloalkyl, carboxy, acyl, acyloxy, amino, cyano, nitro, carbonyl, ester, ether, amide, imino, alkylthio, aryl and heterocyclyl.

As used herein, the term "alkoxy" whether used alone or as part of a substituent group, refers to an alkyl group as defined above attached via oxygen linkage to the rest of the molecule. Examples of alkoxy include, but are not limited to methoxy and ethoxy.

As used herein, the term "haloalkyl" refers to an alkyl group in which one or more hydrogen atoms are replaced by one or more halogen atoms. "Halo-$C_1$-$C_8$ alkyl" groups have 1 to 8 carbon atoms, "halo-$C_1$-$C_6$ alkyl" groups have 1 to 6 carbon atoms. Examples of haloalkyl include, but not limited to, mono-, di- or tri-fluoromethyl; mono-, di- or tri-chloromethyl; mono-, di-, tri-, tetra- or pentafluoroethyl; heptafluoropropyl; difluorochloromethyl and dichlorofluoromethyl.

As used herein, the term "acyl" refers to the group —C(O)$R_a$, wherein $R_a$ is alkyl, cycloalkyl, aryl, aralkyl, heteroaryl, heterocyclyl and heterocyclylalkyl. Unless otherwise stated, the groups alkyl, cycloalkyl, aryl, aralkyl, heteroaryl, heterocyclyl and heterocyclylalkyl can be unsubstituted or substituted with halogen, carboxy, cycloalkyl, cyano, amide, alkylthio, thioester, sulfonyl, nitro, haloalkyl, —$OR_x$, —$SR_x$, —$NR_yR_z$, —$NR_yCOR_z$, —$CONR_yR_z$, —$S(O)_mR_y$, —$S(O)_nNR_yR_z$, —$NR_ySOR_z$, —$NR_ySO_2R_z$, wherein $R_x$ is hydrogen, alkyl, cycloalkyl, aryl, heteroaryl or heterocyclyl; wherein $R_y$ and $R_z$ are independently selected from hydrogen, hydroxy, alkyl, alkoxy, alkenyl, alkynyl, cycloalkyl, aryl, aralkyl and heterocyclyl; m is an integer from 0 to 2 and n is an integer from 0 to 1.

As used herein, the term "aryl" whether used alone or as part of a substituent group, refers to a monocyclic or polycyclic hydrocarbon group having 6 to 14 ring carbon atoms, in which the carbocyclic ring present has a conjugated π electron system. Examples of aryl include, but are not limited to, phenyl, naphthyl, biphenyl, fluorenyl and anthracenyl. Unless stated otherwise, the "aryl" may be unsubstituted or substituted with one or more of the same or different groups, such as halogen, alkyl, alkenyl, alkynyl, haloalkyl, hydroxy, alkoxy, haloalkoxy, cyano, nitro, acyl, carboxy, thiol, carbonyl, aryl, cycloalkyl, heteroaryl, heterocyclyl, $-OR_x$, $-SR_x$, $-NR_yR_z$, $-CONR_yR_z$, $-NR_yCOR_z$, $-NR_yCONR_yR_z$, $-NR_ySOR_z$, $-NR_ySO_2R_z$, $-S(O)_mR_y$, $-S(O)_nNR_yR_z$, wherein $R_x$ is hydrogen, alkyl, cycloalkyl, aryl, heteroaryl or heterocyclyl; $R_y$ and $R_z$ are independently selected from hydrogen, hydroxy, alkyl, alkoxy, alkenyl, alkynyl, cycloalkyl, aryl, aralkyl, heteroaryl and heterocyclyl; m is an integer from 0 to 2 and n is an integer from 0 to 1.

The term "aryloxy" refers to the —O-aryl wherein the term aryl is as defined above. Exemplary aryloxy groups include, but are not limited to, phenoxy and naphthoxy.

As used herein, the terms "heterocyclyl" or "heterocyclic" whether used alone or as part of a substituent group, refers to a saturated, partially unsaturated, monocyclic or polycyclic ring system containing 1 to 10 carbon atoms and 1 to 4 identical or different heteroatoms selected from oxygen, nitrogen and sulfur. Examples of heterocyclyl include, but are not limited to, aziridinyl, azetidinyl, pyrrolidinyl, piperidinyl, azepanyl, azocinyl, dihydrofuranyl, dihydroisoxazolyl, tetrahydrofuranyl, piperazinyl, morpholinyl, oxazinyl, dihydropyridooxazinyl, tetrahydrothiopyranyl, dihydrobenzofuryl, tetrahydroquinoline, tetrahydroisoquinoline, benzoxazinyl, phenoxazinyl, phenothiazinyl and N-oxides thereof. Unless stated otherwise, the "heterocyclyl" or "heterocyclic" may be unsubstituted or substituted with one or more of the same or different groups, such as halogen, hydroxy, cyano, nitro, acyl, oxo, alkyl, alkenyl, alkynyl, haloalkyl, alkoxy, haloalkoxy, $-OR_x$, $-SR_x$, $-C(O)R_y$—$NR_yR_z$, $-CONR_yR_z$, $-NR_yCOR_z$, $-NR_yCONR_yR_z$, $-NR_ySOR_z$, $-NR_ySO_2R_z$, $-S(O)_mR_y$, $-S(O)_nNR_yR_z$, aryl, cycloalkyl, heteroaryl wherein $R_x$ is hydrogen, alkyl, cycloalkyl, aryl, heteroaryl or heterocyclyl; wherein $R_y$ and $R_z$ are independently selected from hydrogen, hydroxy, alkyl, alkoxy, alkenyl, alkynyl, cycloalkyl, aryl, aralkyl, heteroaryl and heterocyclyl; m is an integer from 0 to 2 and n is an integer from 0 to 1.

As used herein, the term "heteroaryl" whether used alone or as part of a substituent group, refers to aromatic ring structure containing monocyclic or polycyclic ring system containing 1 to 10 carbon atoms and 1 to 4 identical or different heteroatoms selected from oxygen, nitrogen and sulfur. Examples of heteroaryl include, but are not limited to, pyrrolyl, thienyl, furanyl, oxazolyl, isoxazolyl, thiazolyl, isothiazolyl, pyrazolyl, imidazolyl, triazolyl, tetrazolyl, oxadiazolyl, thiadiazolyl, pyridinyl, pyridazinyl, pyrimidinyl, pyrazinyl, indolyl, isoindolyl, benzoxazolyl, benzothiazolyl, indazolyl, quinolinyl, isoquinolyl, benzofurazanyl and purinyl. The oxidized form of the ring nitrogen and sulfur atom of the heteroaryl to provide N-oxide, sulfinyl or sulfonyl is also encompassed. Unless stated otherwise, the "heteroaryl" may be unsubstituted or substituted with one or more of the same or different groups, such as halogen, hydroxy, cyano, nitro, acyl, oxo, ester, alkyl, alkenyl, alkynyl, haloalkyl, alkoxy, haloalkoxy, $-OR_x$, $-SR_x$, $-C(O)R_y$—$NR_yR_z$, $-CONR_yR_z$, $-NR_yCOR_z$, $-NR_yCONR_yR_z$, $-NR_ySOR_z$, $-NR_ySO_2R_z$, $-S(O)_mR_y$, $-S(O)_nNR_yR_z$, aryl, cycloalkyl, heteroaryl, heterocyclyl, wherein $R_x$ is hydrogen, alkyl, cycloalkyl, aryl, heteroaryl or heterocyclyl; wherein $R_y$ and $R_z$ are independently selected from hydrogen, hydroxy, alkyl, alkoxy, alkenyl, alkynyl, cycloalkyl, aryl, aralkyl and heterocyclyl; m is an integer from 0 to 2 and n is an integer from 0 to 1.

As used herein, the term "aralkyl" refers to an alkyl group substituted with an aryl or heteroaryl group, wherein the terms alkyl, aryl and heteroaryl are as defined above. Exemplary aralkyl groups include —$(CH_2)_p$-phenyl, —$(CH_2)_p$-pyridyl, wherein p is an integer from 1 to 6. The alkyl, aryl and heteroaryl in the said aralkyl group are as defined earlier.

As used herein, the term "heteroatom" refers to nitrogen, oxygen and sulfur. It should be noted that, unless stated otherwise, any heteroatom with unsatisfied valences is assumed to have a hydrogen atom to satisfy the valences. The ring heteroatoms can be present in any desired number and in any position with respect to each other provided that the resulting heterocyclic system is stable and suitable as a subgroup in a drug substance.

As used herein, the term "halo" or "halogen" unless otherwise stated refers to fluorine, chlorine, bromine, or iodine atom.

As used herein, the term "amino" refers to a group of formula $-NH_2$, which may be optionally substituted with alkyl, alkenyl, alkynyl, aryl, heterocyclyl, or cycloalkyl wherein the terms alkyl, alkenyl, alkynyl, aryl, heterocyclyl and cycloalkyl are as defined herein above.

As used herein, the term "amide" means —C(O)NH—R', wherein R' is hydrogen, alkyl, aryl or aralkyl.

As used herein, the term "imino" refers to a group of formula $=N-R_a$, wherein $R_a$ is selected from hydrogen, hydroxy, alkyl and alkoxy. Examples of such imino radicals include, but are not limited to, $=NH$, $=NCH_3$, $=NOH$, and $=NOCH_3$.

As used herein, the term "oxo" refers to a $=O$ moiety.

As used herein, the term "sulfonyl" refers to a $-SO_2-$ group.

As used herein, the term "carboxy" or "carboxyl" refers to a group of formula —COOH; also referred to as a carboxylic acid group.

As used herein, the term "carbonyl" whether used alone or as part of a substituent group, refers to a group of formula —(C=O)—.

As used herein, the term "ester" refers to a group of formula —$COOR_a$, wherein $R_a$ is an alkyl, cycloalkyl, aryl, aralkyl, heteroaryl or heterocyclyl as defined above.

As used herein, the term "ether" refers to a group of formula —$R_aOR_a$, wherein $R_a$ is independently selected from alkyl, cycloalkyl, aryl, aralkyl, heteroaryl or heterocyclyl as defined above.

As used herein, the term "thioester" refers to a group of formula —$R_aSCOR_a$, wherein $R_a$ is an alkyl, cycloalkyl, aryl, aralkyl, heteroaryl or heterocyclyl as defined above.

As used herein, the term "acyloxy" refers to a group of formula —O-acyl, wherein acyl is as defined above.

As used herein, the term "alkylthio" refers to an alkyl group, as defined herein, appended to the parent molecular moiety through a sulfur atom. Examples of alkylthio include, but are not limited, methylthio, ethylthio, tert-butylthio and hexylthio.

As used herein, the term "pharmaceutically acceptable salts" refers to non-toxic salts of the compounds of present invention. Salts derived from inorganic bases include, but are not limited to, ammonium, calcium, lithium, magnesium, potassium, sodium. Salts derived from pharmaceutically acceptable organic bases include, but are not limited to salts of primary, secondary, and tertiary amines, substituted amines including [(tris(hydroxymethyl)aminomethane], trimethylamine salts, diethylamine salts; salts with amino acids such as lysine, arginine, guanidine and the like. Salts derived from pharmaceutically acceptable organic and inorganic acids include, but are not limited to acetate, ascorbate, aspartate, benzenesulfonate, benzoate, bisulfate, cinnamate, citrate, fumarate, glutamate, lactate, maleate, malonate, methanesulfonate, nitrate, oxalate, propionate, phosphate, p-toluenesulfonate, salicylate, succinate, sulfamate, sulfate, tartrate, hydrochloride, hydrobromide, hydrofluoride, hydroiodide, trifluoromethanesulfonate and valproate.

The term "N-oxide" as used herein refers to the oxide of the nitrogen atom of a nitrogen-containing heteroaryl or heterocycle. N-oxide can be formed in presence of an oxidizing agent for example peroxide such as m-chloro-perbenzoic acid or hydrogen peroxide.

As used herein, the term "solvate" describes a complex wherein the compound is coordinated with a proportional amount of a solvent molecule. Specific solvates, wherein the solvent is water, are referred to as hydrates.

As used herein, the term "pharmaceutically acceptable carrier" refers to a material that is non-toxic, inert, solid, semi-solid or liquid filler, diluent, encapsulating material or formulation auxiliary of any type which is compatible with a subject, preferably a mammal, more preferably a human, and is suitable for delivering an active agent to the target site without terminating the activity of the agent.

As used herein, the term "prodrug" refers to a compound, which upon administration to a subject undergoes chemical conversion by metabolic or chemical processes to yield a compound of the formula (I) or a salt and/or solvate thereof. The preferable prodrugs are Type I, those that are converted intracellularly, more preferably Type Ia where the cellular converting location is the site of therapeutic action. Various forms of prodrugs are well known in the art and are described in: (a) "Pro-drugs as Novel Delivery Systems," by T. Higuchi and W. Stella, Vol. 14 of the A.C.S. Symposium Series, (b) Bioreversible Carriers in Drug Design, ed. Edward B. Roche, American Pharmaceutical Association and Pergamon Press, 1987 and (c) Design of Prodrugs, edited by H. Bundgaard, (Elsevier, 1985).

As used herein, the term "stereoisomer" is a general term used for all isomers of individual compounds that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers). The compounds of the present invention may have asymmetric centers and occur as racemates, racemic mixtures, individual diastereoisomers, or enantiomers, or may exist as geometric isomers, with all isomeric forms of said compounds being included in the present invention.

As used herein, the term "tautomer" refers to the coexistence of two (or more) compounds that differ from each other only in the position of one (or more) mobile atoms and in electron distribution, for example, keto-enol tautomers.

As used herein, the terms "treat" and "therapy" and the like refer to alleviate, slow the progression, prophylaxis, modulation, attenuation or cure of existing disease (e.g., cancer or inflammation).

The present invention also includes within its scope all isotopically labeled forms of compounds of formula (I), wherein one or more atoms of compounds of formula (I) are replaced by their respective isotopes. Examples of isotopes that may be incorporated into the compounds disclosed herein include, but are not limited to, isotopes of hydrogen such as $^2H$ and $^3H$, carbon such as $^{11}C$, $^{13}C$ and $^{14}C$, nitrogen such as $^{13}N$ and $^{15}N$, oxygen such as $^{15}O$, $^{17}O$ and $^{18}O$, chlorine such as $^{36}Cl$, fluorine such as $^{18}F$ and sulphur such as $^{35}S$.

Substitution with heavier isotopes, for example, replacing one or more key carbon-hydrogen bonds with carbon-deuterium bond may show certain therapeutic advantages, for example, longer metabolism cycles, improved safety or greater effectiveness.

Isotopically labeled forms of compounds of formula (I), can be prepared by conventional techniques known to those skilled in the art or by processes analogous to those described above and in the subsequent Experimental section by using an appropriate isotopically labeled reagent instead of non-labeled reagent.

Embodiments

In one embodiment, the present invention provides compounds of formula (I), wherein, $R_a$, $R_b$ and $R_d$ are independently selected from hydrogen, hydroxy, halogen, cyano, nitro, —$COR_1$, —$COOR_1$, —$CONH_2$, —$NR_1R_2$, —$C_1$-$C_8$ alkyl, halo-$C_1$-$C_8$ alkyl and —$C_1$-$C_8$ alkoxy;

$R_c$ is halogen or heteroaryl;

$R_e$ is hydrogen or —$C_1$-$C_8$ alkyl;

Q is —$SO_2$, —$C(O)NR_1$ or —$C(S)NR_1$;

$R_f$ is —$C_1$-$C_8$alkyl, —$(CR_1R_2)_p$—$C_3$-$C_8$ cycloalkyl, —$(CR_1R_2)_p$—$C_6$-$C_{14}$ aryl, —$(CR_1R_2)_p$ heterocyclyl, —$(CR_1R_2)_p$ heteroaryl, —$C_3$-$C_8$ cycloalkyl, —$C_6$-$C_{14}$ aryl, heteroaryl or heterocyclyl;

$R_1$ and $R_2$ are independently selected from hydrogen and lower alkyl;

p is independently an integer from 1 to 3;

with the proviso that when Q is —$SO_2$, then $R_c$ is not halogen; wherein each of the above alkyl, haloalkyl, alkoxy, cycloalkyl, aryl, heterocyclyl and heteroaryl are unsubstituted or substituted with one or more of the same or different groups such as halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo-$C_1$-$C_6$ alkyl, halo-$C_1$-$C_6$ alkoxy, —$C_1$-$C_6$ alkoxy, —$C_3$-$C_8$ cycloalkyl, —$(CR_1R_2)_p$—$C_6$-$C_{10}$ aryl, —$C_6$-$C_{10}$ aryl, —NHCOMe, —$S(O)_2Me$, aryloxy, heterocyclyl and heteroaryl group;

in all their stereoisomeric and tautomeric forms and mixtures thereof in all ratios, prodrugs, N-oxides, and their pharmaceutically acceptable salts and pharmaceutically acceptable solvates.

In another embodiment, the present invention provides compounds of formula (I), wherein, $R_a$, $R_b$ and $R_d$ are independently selected from hydrogen and —$C_1$-$C_8$ alkyl;

$R_c$ is halogen or heteroaryl;

$R_e$ is hydrogen or —$C_1$-$C_8$ alkyl;

Q is —$SO_2$, —$C(O)NR_1$ or —$C(S)NR_1$;

$R_f$ is —$C_1$-$C_8$ alkyl, —$(CR_1R_2)_p$—$C_3$-$C_8$ cycloalkyl, —$(CR_1R_2)_p$—$C_6$-$C_{14}$ aryl, —$(CR_1R_2)_p$-heterocyclyl, —$(CR_1R_2)_p$-heteroaryl, —$C_3$-$C_8$ cycloalkyl, —$C_6$-$C_{14}$ aryl, heteroaryl or heterocyclyl;

$R_1$ and $R_2$ are independently selected from hydrogen and lower alkyl;

p is independently an integer from 1 to 3;

with the proviso that when Q is —$SO_2$, then $R_c$ is not halogen; wherein each of the above alkyl, cycloalkyl, aryl, heterocyclyl and heteroaryl are unsubstituted or substituted with one or more of the same or different groups such as halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo-$C_1$-$C_6$ alkyl, halo-$C_1$-$C_6$ alkoxy, —$C_1$-$C_6$ alkoxy, —$C_3$-$C_8$ cycloalkyl, —$(CR_1R_2)_p$—$C_6$-$C_{10}$ aryl, —$C_6$-$C_{10}$ aryl, —NHCOMe, —$S(O)_2$Me, aryloxy, heterocyclyl and heteroaryl;

in all their stereoisomeric and tautomeric forms and mixtures thereof in all ratios, prodrugs, N-oxides, and their pharmaceutically acceptable salts and pharmaceutically acceptable solvates.

In another embodiment, the present invention provides compounds of formula (I), wherein, $R_a$, $R_b$ and $R_d$ are independently selected from hydrogen and —$C_1$-$C_4$ alkyl;

$R_c$ is halogen or heteroaryl;

$R_e$ is hydrogen or —$C_1$-$C_4$ alkyl;

Q is —$SO_2$, —C(O)NH or —C(S)NH;

$R_f$ is —$C_1$-$C_8$ alkyl, —$(CR_1R_2)_p$—$C_6$-$C_{14}$ aryl, —$(CR_1R_2)_p$ heterocyclyl, —$C_3$-$C_8$ cycloalkyl, —$C_6$-$C_{14}$ aryl, heterocyclyl, or heteroaryl;

$R_1$ and $R_2$ are independently selected from hydrogen and lower alkyl;

p is independently an integer from 1 to 3;

with the proviso that when Q is —$SO_2$, then $R_c$ is not halogen;

wherein each of the above alkyl, cycloalkyl, aryl, heteroaryl and heterocyclyl are optionally and independently substituted with one or more of the same or different groups such as halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo-$C_1$-$C_6$ alkyl, halo-$C_1$-$C_6$ alkoxy, —$C_1$-$C_6$ alkoxy, —NHCOMe, —$S(O)_2$Me, aryloxy, heterocyclyl and heteroaryl;

in all their stereoisomeric and tautomeric forms and mixtures thereof in all ratios, their pharmaceutically acceptable salts, N-oxides, pharmaceutically acceptable solvates and prodrugs.

In another embodiment, the present invention provides compound of formula (I), wherein, $R_a$, $R_b$ and $R_d$ are independently selected from hydrogen and —$C_1$-$C_4$ alkyl;

$R_c$ is halogen or heteroaryl;

$R_e$ is hydrogen or —$C_1$-$C_4$ alkyl;

Q is —C(O)NH or —C(S)NH;

$R_f$ is —$C_1$-$C_8$ alkyl, —$(CR_1R_2)_p$—$C_6$-$C_{14}$ aryl, —$(CR_1R_2)_p$— heterocyclyl, —$C_3$-$C_8$ cycloalkyl, —$C_6$-$C_{14}$ aryl or heteroaryl;

$R_1$ and $R_2$ are independently selected from hydrogen and lower alkyl;

p is independently an integer from 1 to 3;

wherein each of the above alkyl, cycloalkyl, aryl and heteroaryl are optionally and independently substituted with one or more of the same or different groups such as halogen, hydroxy, cyano, amino, nitro, alkoxy, —$C_1$-$C_6$ alkyl and halo-$C_1$-$C_6$ alkyl;

in all their stereoisomeric and tautomeric forms and mixtures thereof in all ratios, prodrugs, N-oxides, and their pharmaceutically acceptable salts and pharmaceutically acceptable solvates.

In another embodiment, the present invention provides compound of formula (I), wherein, $R_a$, $R_b$ and $R_d$ are independently selected from hydrogen and —$C_1$-$C_4$ alkyl;

$R_c$ is halogen or heteroaryl;

$R_e$ is hydrogen or —$C_1$-$C_4$ alkyl;

Q is —C(O)NH or —C(S)NH;

$R_f$ is —$(CR_1R_2)_p$-heterocyclyl, —$(CR_1R_2)_p$—$C_6$-$C_{14}$ aryl or —$C_6$-$C_{14}$ aryl;

$R_1$ and $R_2$ are independently selected from hydrogen and lower alkyl;

p is independently an integer from 1 to 3;

wherein each of the above alkyl, aryl and heteroaryl are optionally and independently substituted with one or more of the same or different groups such as halogen, hydroxy, cyano, amino, nitro, alkoxy, —$C_1$-$C_6$ alkyl and halo-$C_1$-$C_6$ alkyl;

in all their stereoisomeric and tautomeric forms and mixtures thereof in all ratios, prodrugs, N-oxides, and their pharmaceutically acceptable salts and pharmaceutically acceptable solvates.

In another embodiment, the present invention provides compound of formula (I), wherein, $R_a$, $R_b$ and $R_d$ are independently selected from hydrogen and —$C_1$-$C_4$ alkyl;

$R_c$ is halogen;

$R_e$ is hydrogen or —$C_1$-$C_4$ alkyl;

Q is —C(O)NH or —C(S)NH;

$R_f$ is —$(CR_1R_2)_p$-heterocyclyl, —$(CR_1R_2)_p$—$C_6$-$C_{14}$ aryl or —$C_6$-$C_{14}$ aryl;

$R_1$ and $R_2$ are independently selected from hydrogen and lower alkyl;

p is independently an integer from 1 to 3;

wherein each of the above alkyl, aryl and heteroaryl are optionally and independently substituted with one or more of the same or different groups such as halogen, hydroxy, cyano, amino, nitro, alkoxy, —$C_1$-$C_6$ alkyl and halo-$C_1$-$C_6$ alkyl;

in all their stereoisomeric and tautomeric forms and mixtures thereof in all ratios, their pharmaceutically acceptable salts, N-oxides, pharmaceutically acceptable solvates and prodrugs.

In another embodiment, the present invention provides compounds of formula (I), wherein, $R_a$, $R_b$ and $R_d$ are independently selected from hydrogen and —$C_1$-$C_4$ alkyl;

$R_c$ is heteroaryl;

$R_e$ is hydrogen or —$C_1$-$C_4$ alkyl;

Q is —$SO_2$, —$C(O)NR_1$ or —$C(S)NR_1$;

$R_f$ is —$C_1$-$C_8$ alkyl, —$(CR_1R_2)_p$—$C_3$-$C_8$ cycloalkyl, —$(CR_1R_2)_p$—$C_6$-$C_{14}$ aryl, —$(CR_1R_2)_p$-heterocyclyl, —$(CR_1R_2)_p$-heteroaryl, —$C_3$-$C_8$ cycloalkyl, —$C_6$-$C_{14}$ aryl, heteroaryl or heterocyclyl;

$R_1$ and $R_2$ are independently selected from hydrogen and lower alkyl;

p is independently an integer from 1 to 3;

wherein each of the above alkyl, cycloalkyl, aryl, heterocyclyl and heteroaryl are optionally and independently substituted with one or more of the same or different groups such as halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo-$C_1$-$C_6$ alkyl, —$C_1$-$C_6$ alkoxy, —$C_3$-$C_8$ cycloalkyl, —$(CR_1R_2)_p$—$C_6$-$C_{10}$ aryl, —$C_6$-$C_{10}$ aryl, —NHCOMe, —$S(O)_2$Me, aryloxy, heterocyclyl and heteroaryl;

in all their stereoisomeric and tautomeric forms and mixtures thereof in all ratios, prodrugs, N-oxides, and their pharmaceutically acceptable salts and pharmaceutically acceptable solvates.

In another embodiment, the present invention provides compound of formula (I), wherein, $R_a$, $R_b$ and $R_d$ are independently selected from hydrogen and —$C_1$-$C_4$ alkyl;

$R_c$ is heteroaryl;

$R_e$ is hydrogen or —$C_1$-$C_4$ alkyl;

Q is —$SO_2$, —C(O)NH or —C(S)NH;

$R_f$ is —$C_1$-$C_8$ alkyl, —$(CH_2)_p$—$C_6$-$C_{14}$ aryl, —$(CH_2)_p$— heterocyclyl, —$(CH_2)_p$-heteroaryl, —$C_3$-$C_8$ cycloalkyl, —$C_6$-$C_{14}$ aryl, heteroaryl or heterocyclyl;

$R_1$ and $R_2$ are independently selected from hydrogen and lower alkyl;

p is independently an integer from 1 to 3;

wherein each of the above alkyl, aryl, heterocyclyl and heteroaryl are optionally and independently substituted with one or more of the same or different groups such as halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo-$C_1$-$C_6$ alkyl, —$C_1$-$C_6$ alkoxy, —$C_3$-$C_8$ cycloalkyl, —$(CR_1R_2)_p$—$C_6$-$C_{10}$ aryl, —$C_6$-$C_{10}$ aryl, —NHCOMe, —$S(O)_2$Me, aryloxy, heterocyclyl and heteroaryl;

in all their stereoisomeric and tautomeric forms and mixtures thereof in all ratios, prodrugs, N-oxides, and their pharmaceutically acceptable salts and pharmaceutically acceptable solvates.

In another embodiment, the present invention provides compounds of formula (I), $R_a$, $R_b$ and $R_d$ are independently selected from hydrogen and methyl;

$R_c$ is halogen or heteroaryl selected from pyridyl, quinolinyl, indolyl, pyrimidinyl and pyrrolyl wherein each of pyridyl, quinolinyl, indolyl, pyrimidinyl and pyrrolyl is optionally substituted with one or more halogen, —$C_1$-$C_6$-alkyl, —$C_1$-$C_6$-alkoxy, and halo-$C_1$-$C_6$-alkyl;

$R_e$ is hydrogen or —$C_1$-$C_4$ alkyl;

Q is —$SO_2$, —C(O)NH or —C(S)NH;

$R_f$ is —$C_1$-$C_8$ alkyl, —$(CH_2)_p$—$C_6$-$C_{14}$ aryl, —$(CH_2)_p$-heterocyclyl, —$C_3$-$C_8$-cycloalkyl, —$C_6$-$C_{14}$ aryl, heterocyclyl or heteroaryl;

p is independently an integer from 1 to 3;

$R_1$ and $R_2$ are independently selected from hydrogen and lower alkyl;

with the proviso that when Q is —$SO_2$, then $R_c$ is not halogen;

wherein each of the above alkyl, cycloalkyl, aryl, heteroaryl and heterocyclyl are optionally and independently substituted with one or more of the same or different groups such as halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo-$C_1$-$C_6$ alkyl, halo-$C_1$-$C_6$ alkoxy, —$C_1$-$C_6$alkoxy, —$C_3$-$C_8$ cycloalkyl, —$(CR_1R_2)_p$—$C_6$-$C_{10}$ aryl, —$C_6$-$C_{10}$ aryl, —NHCOMe, —$S(O)_2$Me, aryloxy, heterocyclyl and heteroaryl group;

in all their stereoisomeric and tautomeric forms and mixtures thereof in all ratios, their pharmaceutically acceptable salts, N-oxides, pharmaceutically acceptable solvates and prodrugs.

In another embodiment, the present invention provides compounds of formula (I), wherein, $R_a$, $R_b$ and $R_d$ are independently selected from hydrogen and —$C_1$-$C_4$ alkyl;

$R_c$ is heteroaryl;

$R_e$ is hydrogen or —$C_1$-$C_4$ alkyl;

Q is —$SO_2$;

$R_f$ is —$C_1$-$C_8$ alkyl, —$(CR_1R_2)_p$—$C_6$-$C_{14}$ aryl, —$C_3$-$C_8$ cycloalkyl, —$C_6$-$C_{14}$ aryl, heteroaryl or heterocyclyl;

p is independently an integer from 1 to 3;

$R_1$ and $R_2$ are independently selected from hydrogen and lower alkyl;

wherein each of the above alkyl, cycloalkyl, aryl, heterocyclyl and heteroaryl are unsubstituted or substituted with one or more of the same or different groups such as halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo-$C_1$-$C_6$ alkyl, halo-$C_1$-$C_6$ alkoxy, —$C_1$-$C_6$alkoxy, —$C_3$-$C_8$ cycloalkyl, —$(CR_1R_2)_p$—$C_6$-$C_{10}$ aryl, —$C_6$-$C_{10}$ aryl, —NHCOMe, —$S(O)_2$Me, aryloxy, heterocyclyl and heteroaryl group;

in all their stereoisomeric and tautomeric forms and mixtures thereof in all ratios, their pharmaceutically acceptable salts, pharmaceutically acceptable solvates, prodrugs and N-oxides.

In another embodiment, the present invention provides compounds of formula (I), wherein, $R_a$, $R_b$ and $R_d$ are independently selected from hydrogen and methyl;

$R_c$ is heteroaryl selected from indolyl, pyrrolyl, pyridyl, pyrimidinyl and quinolinyl, wherein each of indolyl, pyrrolyl, pyridyl, pyrimidinyl and quinolinyl is optionally substituted with one or more groups selected from halogen, —$C_1$-$C_6$-alkyl, —$C_1$-$C_6$-alkoxy, and halo-$C_1$-$C_6$-alkyl;

$R_e$ is hydrogen or —$C_1$-$C_4$ alkyl;

Q is —$SO_2$;

$R_f$ is —$C_1$-$C_8$ alkyl, —$(CH_2)_p$—$C_6$-$C_{14}$ aryl, —$C_3$-$C_8$ cycloalkyl, —$C_6$-$C_{14}$ aryl, heteroaryl or heterocyclyl;

p is independently an integer from 1 to 3;

$R_1$ and $R_2$ are independently selected from hydrogen and lower alkyl;

wherein each of the above alkyl, cycloalkyl, aryl, heterocyclyl and heteroaryl are unsubstituted or substituted with one or more of the same or different groups such as halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo-$C_1$-$C_6$ alkyl, halo-$C_1$-$C_6$ alkoxy, —$C_1$-$C_6$alkoxy, —$C_3$-$C_8$ cycloalkyl, —$(CR_1R_2)_p$—$C_6$-$C_{10}$ aryl, —$C_6$-$C_{10}$ aryl, —NHCOMe, —$S(O)_2$Me, aryloxy, heterocyclyl and heteroaryl group;

in all their stereoisomeric and tautomeric forms and mixtures thereof in all ratios, their pharmaceutically acceptable salts, pharmaceutically acceptable solvates, prodrugs and N-oxides.

In another embodiment, the present invention provides compounds of formula (I), $R_a$, $R_b$ and $R_d$ are independently selected from hydrogen and methyl;

$R_c$ is halogen or heteroaryl selected from pyridyl, quinolinyl, indolyl, pyrimidinyl and pyrrolyl wherein each of pyridyl, quinolinyl, indolyl, pyrimidinyl and pyrrolyl is optionally substituted with one or more halogen, —$C_1$-$C_6$-alkyl, —$C_1$-$C_6$-alkoxy, and halo-$C_1$-$C_6$-alkyl;

$R_e$ is hydrogen or —$C_1$-$C_4$ alkyl;

Q is —$SO_2$, —C(O)NH or —C(S)NH;

$R_f$ is hexyl, —$(CH_2)$-phenyl, —$(CH_2)$-2-morpholinyl, cyclohexyl, phenyl, thiophenyl, imidazolyl, pyrrolyl, furanyl, dihydro-pyridooxazinyl or quinolinyl; wherein each of hexyl, —$(CH_2)$— phenyl, —$(CH_2)$-2-morpholinyl, cyclohexyl, phenyl, thiophenyl, imidazolyl, pyrrolyl, furanyl, dihydro-pyridooxazinyl and quinolinyl are optionally and independently substituted with one or more of the same or different groups such as halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo-$C_1$-$C_6$ alkyl, halo-$C_1$-$C_6$ alkoxy, —$C_1$-$C_6$ alkoxy, —$C_3$-$C_8$ cycloalkyl, —$(CR_1R_2)_p$—$C_6$-$C_{10}$ aryl, —$C_6$-$C_{10}$ aryl, —NHCOMe, —$S(O)_2$Me, aryloxy, heterocyclyl and heteroaryl group;

$R_1$ and $R_2$ are independently selected from hydrogen and lower alkyl;

p is independently an integer from 1 to 3;

with the proviso that when Q is —$SO_2$, then $R_c$ is not halogen;

in all their stereoisomeric and tautomeric forms and mixtures thereof in all ratios, their pharmaceutically acceptable salts, N-oxides, pharmaceutically acceptable solvates and prodrugs.

In another embodiment, the present invention provides compounds of formula (I), $R_a$, $R_b$ and $R_d$ are independently selected from hydrogen and methyl;

$R_c$ is halogen, pyridin-3-yl, pyridin-4-yl, 2-fluoropyridin-3-yl, 5-fluoropyridin-3yl, 5-trifluoromethylpyridin-3yl, 6-chloropyridin-3yl, 6-fluoropyridin-3yl, 6-fluoro-5-methylpyridin-3yl, 6-methylpyridin-3yl, 6-methoxypyridin-3y1, quinolinyl, 2-indolyl, 1-methyl-1H-indol-3-yl, pyrimidin-5-yl, 2,4-dimethoxypyrimidin-5-yl, 2-methoxypyrimidin-5-yl, and 1H-pyrrol-2-yl;

$R_e$ is hydrogen or —$C_1$-$C_4$ alkyl;

Q is —$SO_2$, —C(O)NH or —C(S)NH;

$R_f$ is hexyl, —($CH_2$)-phenyl, —($CH_2$)$_2$-morpholinyl, cyclohexyl, phenyl, 2-bromophenyl, 3-bromophenyl, 4-bromophenyl, 2,5-dibromophenyl, 2-bromo-4-fluorophenyl, 2-bromo-5-trifluoromethylphenyl, 2-bromo-4,6-difluorophenyl, 4-bromo-2,5-difluorophenyl, 4-bromo-2,6-difluorophenyl, 4-bromo-2,6-dichlorophenyl, 4-bromo-3-methylphenyl, 4-bromo-2-chlorophenyl, 4-bromo-2-trifluoromethoxyphenyl, 5-bromo-2-methoxyphenyl, 2-chlorophenyl, 3-chlorophenyl, 2-chloro-4-trifluoromethylphenyl, 2-chloro-5-trifluoromethylphenyl, 2-chloro-4-fluorophenyl, 3-chloro-2-fluorophenyl, 3-chloro-4-fluoro-phenyl, 3-chloro-2-methylphenyl, 4-chloro-3-nitrophenyl, 4-chloro-2,5-dimethylphenyl, 5-chloro-2-methoyphenyl, 5-chloro-2-fluorophenyl, 2-cyanophenyl, 3-cyanophenyl, 3-cyano-4-fluorophenyl, 4-cyanophenyl, 2-fluorophenyl, 3-fluorophenyl, 4-fluorophenyl, 2,4-difluorophenyl, 2,5-difluorophenyl, 2,6-difluorophenyl, 3,4-difluorophenyl, 3,5-difluorophenyl, 2-fluoro-5-methylphenyl, 3-fluoro-4-methylphenyl, 4-fluoro-2-methylphenyl, 5-fluoro-2-methylphenyl, 5-fluoro-2-methoxyphenyl, 2,3,4-trifluorophenyl, 4-iodophenyl, 2-methylphenyl, 2-methylsulfonylphenyl, 2-methyl-5-nitrophenyl, 3-methylphenyl, 4-methylphenyl, 2,5-dimethylphenyl, 2-methyl-5-carboxyphenyl, 2,4,6-trimethylphenyl, 3-methoxyphenyl, 4-methoxyphenyl, 2,5-dimethoxyphenyl, 2-methoxy-5-amidophenyl, 2-methoxy-4-methylphenyl, 2-methoxy-5-methylphenyl, 2-methoxy-6-methylphenyl, 3-trifluoromethylphenyl, 2-trifluoromethoxyphenyl, 3,5-bis(trifluoromethyl)phenyl, 2-nitrophenyl, 3-nitrophenyl, 2-phenoxyphenyl, 4-phenoxyphenyl, 4-acetamidophenyl, 2-morpholino-5-trifluoromethylphenyl, 2-methyl-5-methylsulfonylphenyl, benzyl, biphenyl-4-yl, 2'-fluoro-5'-(trifluoromethyl)biphenyl, thiophen-2-yl, quinolin-8-yl, 1,2-dimethyl-imidazol-4-yl, cyclohexyl, pyridin-3-yl, 6-morpholino-pyridin-3-yl, methyl(1-methyl-pyrrol-2-yl)-2-carboxylate, 3,4-dihydro-4-methyl-pyrido[3,2-b][1,4]oxazine-7-yl, methyl (thiophen-3-yl)-2-carboxylate, methyl(furan-5-yl)-2-carboxylate or 2-morpholinoethyl;

p is independently an integer from 1 to 3;

with the proviso that when Q is —$SO_2$, then $R_c$ is not halogen;

in all their stereoisomeric and tautomeric forms and mixtures thereof in all ratios, their pharmaceutically acceptable salts, N-oxides, pharmaceutically acceptable solvates and prodrugs.

Representative compounds of the present invention include any of the following compounds or their pharmaceutically acceptable salts and solvates as well as stereoisomers and tautomers thereof. However, the present invention is not limited to these compounds alone:

N-methyl-N'-((6-(pyridin-3-yl)imidazo[1,2-a]pyridin-3-yl) methylene) benzenesulfonohydrazide;

N, 3-dimethyl-N'-((6-pyridin-3-yl) imidazo[1,2-a]pyridine-3-yl)methylene) benzenesulfonohydrazide;

N, 4-dimethyl-N'-((6-(pyridine-3-yl) imidazo[1,2-a]pyridine-3-yl)methylene) benzenesulfonohydrazide;

2-Fluoro-N-methyl-N'-((6-(pyridine-3-yl) imidazo[1,2-a] pyridine-3-yl)methylene) benzenesulfonohydrazide;

3-Fluoro-N-methyl-N'-((6-(pyridine-3-yl) imidazo[1,2-a] pyridine-3-yl)methylene)benzenesulfonohydrazide;

4-Fluoro-N-methyl-N'-((6-(pyridine-3-yl) imidazo[1,2-a] pyridine-3-yl)methylene) benzenesulfonohydrazide;

3-Bromo-N-methyl-N'-((6-(pyridine-3-yl) imidazo[1,2-a] pyridine-3-yl)methylene) benzenesulfonohydrazide;

4-Bromo-N-methyl-N'-((6-(pyridine-3-yl) imidazo[1,2-a] pyridine-3-yl)methylene) benzenesulfonohydrazide;

2-Cyano-N-methyl-N'-((6-(pyridine-3-yl) imidazo[1,2-a]pyridine-3-yl)methylene) benzenesulfonohydrazide;

(E)-3-cyano-N-methyl-N'-((6-(pyridine-3-yl)imidazo[1,2-a] pyridine-3-yl)methylene) benzenesulfonohydrazide;

4-Cyano-N-methyl-N'-((6-(pyridine-3-yl) imidazo[1,2-a]pyridine-3-yl)methylene) benzenesulfonohydrazide;

4-Methoxy-N-methyl-N'-((6-(pyridine-3-yl) imidazo[1,2-a] pyridine-3-yl)methylene) benzenesulfonohydrazide;

2,4-Difluoro-N-methyl-N'-((6-(pyridine-3-yl) imidazo[1,2-a]pyridine-3-yl)methylene)benzenesulfonohydrazide;

2,6-Difluoro-N-methyl-N'-((6-(pyridine-3-yl) imidazo[1,2-a]pyridine-3-yl)methylene)benzenesulfonohydrazide;

3,4-difluoro-N-methyl-N'-((6-(pyridine-3-yl) imidazo[1,2-a] pyridine-3-yl)methylene) benzenesulfonohydrazide;

3,5-Difluoro-N-methyl-N'-((6-(pyridine-3-yl) imidazo[1,2-a]pyridine-3-yl)methylene)benzenesulfonohydrazide;

3-Chloro-2-fluoro-N-methyl-N'-((6-(pyridine-3-yl) imidazo [1,2-a]pyridine-3-yl)methylene)benzenesulfonohydrazide;

3-Chloro-4-fluoro-N-methyl-N'-((6-(pyridine-3-yl) imidazo [1,2-a]pyridine-3-yl)methylene)benzenesulfonohydrazide;

2-Fluoro-N, 5-dimethyl-N'-((6-(pyridine-3-yl) imidazo[1,2-a]pyridine-3-yl)methylene)benzenesulfonohydrazide;

3-Fluoro-N, 4-dimethyl-N'-((6-(pyridine-3-yl) imidazo[1,2-a]pyridine-3-yl)methylene)benzenesulfonohydrazide;

5-Fluoro-N, 2-dimethyl-N'-((6-(pyridine-3-yl) imidazo[1,2-a]pyridine-3-yl) methylene)benzenesulfonohydrazide;

3-(3-((2-(5-fluoro-2-methylphenylsulfonyl)-2-methylhydrazono)methyl)imidazo[1,2-a]pyridin-6-yl)pyridine 1-oxide;

4-Bromo-N, 3-dimethyl-N'-((6-(pyridine-3-yl) imidazo[1,2-a]pyridine-3-yl) methylene)benzenesulfonohydrazide;

N-methyl-N'-((6-(pyridine-3-yl) imidazo[1,2-a]pyridine-3-yl)methylene)-3,5-bis (trifluoromethyl)benzenesulfonohydrazide;

3-Cyano-4-fluoro-N-methyl-N'-((6-(pyridine-3-yl) imidazo [1,2-a]pyridine-3-yl) methylene)benzenesulfonohydrazide;

N, 2-dimethyl-5 nitro-N'-((6-pyridin-3-yl) imidazo[1,2-a]pyridine-3-yl) methylene)benzenesulfonohydrazide;

2-Bromo-4,6-difluoro-N-methyl-N'-((6-(pyridine-3-yl) imidazo[1,2-a]pyridine-3-yl) methylene)benzenesulfonohydrazide;

N, 2,4,6-tetramethyl-N'-((6-(pyridine-3-yl) imidazo[1,2-a] pyridine-3-yl)methylene) benzenesulfonohydrazide;

N-methyl-1-phenyl-N'-((6-pyridin-3-yl) imidazo[1,2-a]pyridine-3-yl)methylene) benzenesulfonohydrazide;

N-methyl-N'-((6-(pyridine-3-yl) imidazo[1,2-a]pyridine-3-yl)methylene)thiophene-2-sulfonohydrazide;

N-methyl-N'-((6-(pyridine-3-yl) imidazo[1,2-a]pyridine-3-yl)methylene) quinoline-8-sulfonohydrazide;

N-methyl-N'-((6-(pyridine-3-yl) imidazo[1,2-a]pyridine-3-yl)methylene) cyclohexanesulfonohydrazide;

3-Fluoro-N, 4-dimethyl-N'-((6-(pyridine-3-yl) imidazo[1,2-a]pyridine-3-yl)methylene) benzenesulfonohydrazide;

3-Cyano-4-fluoro-N-methyl-N'-((6-(pyridine-3-yl) imidazo[1,2-a]pyridine-3-yl) methylene)benzenesulfonohydrazide;

(E)-2,3,4-Trifluoro-N-methyl-N'-((6-(pyridin-3-yl)imidazo[1,2-a]pyridin-3-yl)methylene)benzenesulfonohydrazide;

(E)-4-bromo-2,5-difluoro —N-methyl-N'-((6-(pyridin-3-yl) imidazo[1,2-a]pyridin-3-yl)methylene)benzenesulfonohydrazide;

(E)-2-bromo-4-fluoro-N-methyl-N'-((6-(pyridin-3-yl)imidazo[1,2-a]pyridin-3-yl) methylene)benzenesulfonohydrazide;

(E)-N-methyl-N'((6-(pyridin-3-yl) imidazo[1,2-a]pyridin-3-yl)methylene)-3-(trifluoromethyl)benzenesulfonohydrazide;

(E)-4-bromo-2,6-dichloro-N-methyl-N'((6-(pyridin-3-yl) imidazo[1,2-a]pyridin-3-yl)methylene)benzenesulfonohydrazide;

(E)-3-chloro-N-methyl-N'-((6-(pyridin-3-yl)imidazo[1,2-a]pyridin-3-yl) methylene)benzenesulfonohydrazide;

(E)-2-chloro-N-methyl-N'((6-(pyridin-3-yl) imidazo[1,2-a]pyridin-3-yl)methylene)-4-(trifluoromethyl)benzenesulfonohydrazide;

(E)-2-chloro-4-fluoro-N-methyl-N'((6-(pyridin-3-yl) imidazo[1,2-a]pyridin-3-yl) methylene)benzenesulfonohydrazide;

(E)-N, 1,2-trimethyl-N'((6-(pyridin-3-yl) imidazo[1,2-a]pyridin-3-yl)methylene)-1H-imidazole-4-sulfonohydrazide;

(E)-4-chloro-N, 2,5-trimethyl-N'((6-(pyridin-3-yl) imidazo[1,2-a]pyridin-3-yl)methylene) benzenesulfonohydrazide;

(E)-2,5-difluoro-N-methyl-N'-((6-(pyridin-3-yl) imidazo[1,2-a]pyridin-3-yl)methylene) benzenesulfonohydrazide;

(E)-5-fluoro-2-methoxy-N-methyl-N'-((6-(pyridin-3-yl)imidazo[1,2-a]pyridin-3-yl)methylene)benzenesulfonohydrazide;

(E)-4-Iodo-N-methyl-N'-((6-(pyridin-3-yl)imidazo[1,2-a]pyridin-3-yl)methylene)benzenesulfonohydrazide;

(E)-2'-Fluoro-N-methyl-N'-((6-(pyridin-3-yl)imidazo[1,2-a]pyridin-3-yl)methylene)-5'-(trifluoromethyl)biphenyl-4-sulfonohydrazide;

4-Methyl-3-(1-methyl-2-((6-(pyridin-3-yl) imidazo[1,2-a]pyridin-3-yl)methylene) hydrazinylsulfonyl)benzoic acid;

4-Methoxy-3-(1-methyl-2-((6-(pyridin-3-yl)imidazo[1,2-a]pyridin-3-yl)methylene)hydrazinylsulfonyl)benzamide;

(E)-N, 2,5-trimethyl-N'((6-(pyridin-3-yl) imidazo[1,2-a]pyridin-3-yl)methylene) benzenesulfonohydrazide;

(E)-2,5-dibromo-N-methyl-N'-((6-(pyridin-3-yl) imidazo[1,2-a]pyridin-3-yl)methylene) benzenesulfonohydrazide;

(E)-2,5-dimethoxy-N-methyl-N'((6-(pyridin-3-yl) imidazo[1,2-a]pyridin-3-yl)methylene) benzenesulfonohydrazide;

(E)-N, 2-dimethyl-N'((6-(pyridin-3-yl) imidazo[1,2-a]pyridin-3-yl)methylene) benzenesulfonohydrazide;

(E)-N-methyl-N'-((6-(pyridin-3-yl) imidazo[1,2-a]pyridin-3-yl)methylene)-2-(trifluoromethoxy)benzenesulfonohydrazide;

(E)-5-chloro-2-methoxy-N-methyl-N'-((6-(pyridin-3-yl) imidazo[1,2-a]pyridin-3-yl) methylene)benzenesulfonohydrazide;

(E)-4-bromo-N-methyl-N'-((6-(pyridin-3-yl) imidazo[1,2-a]pyridin-3-yl)methylene)-2-(trifluoromethoxy)benzenesulfonohydrazide;

(E)-2-bromo-N-methyl-N'-((6-(pyridin-3-yl) imidazo[1,2-a]pyridin-3-yl)methylene)-5-(trifluoromethyl)benzenesulfonohydrazide;

(E)-N-methyl-2-nitro-N'((6-(pyridin-3-yl) imidazo[1,2-a]pyridin-3-yl) methylene)benzenesulfonohydrazide;

(E)-N-methyl-2-(methylsulfonyl)-N'-((6-(pyridin-3-yl) imidazo[1,2-a]pyridin-3-yl) methylene)benzenesulfonohydrazide;

(E)-N-methyl-2-phenoxy-N'((6-(pyridin-3-yl) imidazo[1,2-a]pyridin-3-yl) methylene)benzenesulfonohydrazide;

(E)-N-methyl-N'-((6-(pyridin-3-yl) imidazo[1,2-a]pyridin-3-yl)methylene) hexane-1-sulfonohydrazide;

(E)-N-methyl-2-morpholino-N'((6-(pyridin-3-yl) imidazo[1,2-a]pyridin-3-yl)methylene)-5-(trifluoromethyl)benzenesulfonohydrazide;

(E)-N,2-dimethyl-5-(methylsulfonyl)-N'-((6-(pyridin-3-yl) imidazo[1,2-a]pyridin-3-yl) methylene)benzenesulfonohydrazide;

(E)-2-bromo-N-methyl-N-((6-(pyridin-3-yl) imidazo[1,2-a]pyridin-3-yl)methylene) benzenesulfonohydrazide;

(E)-2-chloro-N-methyl-N-((6-(pyridin-3-yl) imidazo[1,2-a]pyridin-3-yl)methylene)-5-(trifluoromethyl)benzenesulfonohydrazide;

(E)-N-methyl-6-morpholino-N-((6-(pyridin-3-yl) imidazo [1,2-a]pyridin-3-yl)methylene) pyridine-3-sulfonohydrazide;

(E)-Methyl 1-methyl-5-(1-methyl-2-((6-(pyridin-3-yl) imidazo[1,2-a]pyridin-3-yl) methylene)hydrazinylsulfonyl)-1H-pyrrole-2-carboxylate;

(E)-N,4-dimethyl-N-((6-(pyridin-3-yl) imidazo[1,2-a]pyridin-3-yl)methylene)-3,4-dihydro-2H-pyrido[3,2-b][1,4]oxazine-7-sulfonohydrazide;

(E)-N-methyl-N-((6-(pyridin-3-yl) imidazo[1,2-a]pyridin-3-yl)methylene) pyridine-3-sulfonohydrazide;

(E)-N-methyl-4-phenoxy-N-((6-(pyridin-3-yl) imidazo[1,2-a]pyridin-3-yl)methylene) benzenesulfonohydrazide;

(E)-Methyl 3-(1-methyl-2-((6-(pyridin-3-yl)imidazo[1,2-a]pyridin-3-yl)methylene) hydrazinylsulfonyl)thiophene-2-carboxylate;

(E)-N-methyl-N-((6-(pyridin-3-yl) imidazo[1,2-a]pyridin-3-yl)methylene) biphenyl-4-sulfonohydrazide;

(E)-Methyl 5-(1-methyl-2-((6-(pyridin-3-yl) imidazo[1,2-a]pyridin-3-yl)methylene) hydrazinylsulfonyl) furan-2-carboxylate;

(E)-4-chloro-N-methyl-3-nitro-N'-((6-(pyridin-3-yl) imidazo[1,2-a]pyridin-3-yl)methylene) benzenesulfonohydrazide;

(E)-5-bromo-2-methoxy-N-methyl-N'-((6-(pyridin-3-yl) imidazo[1,2-a]pyridin-3-yl) methylene)benzenesulfonohydrazide;

(E)-3-chloro-N, 2-dimethyl-N'-((6-(pyridin-3-yl) imidazo[1,2-a]pyridin-3-yl)methylene) benzenesulfonohydrazide;

(E)-5-chloro-2-fluoro-N-methyl-N'-((6-(pyridin-3-yl) imidazo[1,2-a]pyridin-3-yl) methylene)benzenesulfonohydrazide;

(E)-4-Fluoro-N, 2-dimethyl-N'-((6-(pyridin-3-yl) imidazo[1,2-a]pyridin-3-yl)methylene) benzenesulfonohydrazide;

(E)-2-methoxy-N, 6-dimethyl-N'((6-(pyridin-3-yl) imidazo[1,2-a]pyridin-3-yl) methylene)benzenesulfonohydrazide;

(E)-4-Bromo-2-chloro-N-methyl-N'((6-(pyridin-3-yl) imidazo[1,2-a]pyridin-3-yl) methylene)benzenesulfonohydrazide;

(E)-2-chloro-N-methyl-N'((6-(pyridin-3-yl) imidazo[1,2-a]pyridin-3-yl)methylene) benzenesulfonohydrazide;

(E)-N-(4-(1-methyl-2-((6-(pyridin-3-yl) imidazo[1,2-a]pyridin-3-yl)methylene) hydrazinylsulfonyl)phenyl)acetamide;

N'-((6-(6-fluoropyridine-3-yl) imidazo[1,2-a]pyridin-3-yl) methylene)-n, 2-dimethyl-5-nitrobenzenesulfonohydrazide;

(E)-N-ethyl-2-methyl-5-nitro-N'-((6-(pyridin-3-yl)imidazo[1,2-a]pyridin-3-yl) methylene)benzenesulfonohydrazide;

N, 2-dimethyl-5-nitro-N'-((6-(pyridine-4-yl) imidazo[1,2-a]pyridine-3-yl)methylene) benzenesulfonohydrazide;
5-Fluoro-N, 2-dimethyl-N'-((6-(pyridine-4-yl) imidazo[1,2-a]pyridine-3-yl)methylene) benzenesulfonohydrazide;
(E)-5-Fluoro-N'-((6-(2-fluoropyridin-3-yl)imidazo[1,2-a]pyridin-3-yl)methylene)-N,2-dimethylbenzenesulfonohydrazide;
(E)-5-Fluoro-N'-((6-(2-fluoropyridin-3-yl)imidazo[1,2-a]pyridin-3-yl)methylene)-2-methoxy-N-methylbenzenesulfonohydrazide;
(E)-3-fluoro-N'-((6-(2-fluoropyridin-3-yl) imidazo[1,2-a]pyridin-3-yl)methylene)-N-methylbenzenesulfonohydrazide;
(E)-5-chloro-2-fluoro-N'-((6-(2-fluoropyridin-3-yl)imidazo[1,2-a]pyridin-3-yl)methylene)-N-methylbenzenesulfonohydrazide;
(E)-5-bromo-N'-((6-(2-fluoropyridin-3-yl) imidazo[1,2-a]pyridin-3-yl)methylene)-2-methoxy-N-methylbenzenesulfonohydrazide;
(E)-N'-((6-(2-fluoropyridin-3-yl) imidazo[1,2-a]pyridin-3-yl)methylene)-2,5-dimethoxy-N-methylbenzenesulfonohydrazide;
(E)-N'-((6-(2-fluoropyridin-3-yl) imidazo[1,2-a]pyridin-3-yl)methylene)-N, 2-dimethyl-5-(methylsulfonyl)benzenesulfonohydrazide;
(E)-N'-((6-(2-fluoropyridin-3-yl) imidazo[1,2-a]pyridin-3-yl)methylene)-N-methylhexane-1-sulfonohydrazide;
(E)-N'-((6-(2-fluoropyridin-3-yl) imidazo[1,2-a]pyridin-3-yl)methylene)-2-methoxy-N, 4-dimethylbenzenesulfonohydrazide;
(E)-2-bromo-N'-((6-(2-fluoropyridin-3-yl) imidazo[1,2-a]pyridin-3-yl)methylene)-N-methylbenzenesulfonohydrazide;
(E)-2-cyano-N'-((6-(2-fluoropyridin-3-yl) imidazo[1,2-a]pyridin-3-yl)methylene)-N-methylbenzenesulfonohydrazide;
(E)-N'-((6-(2-fluoropyridin-3-yl) imidazo[1,2-a]pyridin-3-yl)methylene)-2-methoxy-N,5-dimethylbenzenesulfonohydrazide;
N, 2-Dimethyl-5-nitro-N'((6-(quinolin-3-yl) imidazo[1,2-a]pyridine-3-yl)methylene) benzenesulfonohydrazide;
(E)-5-Fluoro-N,2-dimethyl-N'-((8-methyl-6-(pyridin-3-yl) imidazo[1,2-a]pyridin-3-yl)methylene)benzenesulfonohydrazide;
(E)-3,5-Difluoro-N-methyl-N'-((8-methyl-6-(pyridin-3-yl) imidazo[1,2-a]pyridin-3-yl)methylene)benzenesulfonohydrazide;
(E)-4-Bromo-2,6-difluoro-N-methyl-N'-((8-methyl-6-(pyridin-3-yl)imidazo[1,2-a]pyridin-3-yl)methylene)benzenesulfonohydrazide;
(E)-N,3-dimethyl-N'-((8-methyl-6-(pyridin-3-yl)imidazo[1,2-a]pyridin-3-yl)methylene)benzenesulfonohydrazide;
(E)-2-cyano-N-methyl-N'-((8-methyl-6-(pyridin-3-yl)imidazo[1,2-a]pyridin-3-yl)methylene)benzenesulfonohydrazide;
(E)-3-cyano-4-fluoro-N-methyl-N'-((8-methyl-6-(pyridin-3-yl)imidazo[1,2-a]pyridin-3-yl)methylene)benzenesulfonohydrazide;
(E)-3-cyano-N-methyl-N'-((8-methyl-6-(pyridin-3-yl)imidazo[1,2-a]pyridin-3-yl)methylene)benzenesulfonohydrazide;
(E)-4-Bromo-N,3-dimethyl-N'-((8-methyl-6-(pyridin-3-yl)imidazo[1,2-a]pyridin-3-yl)methylene)benzenesulfonohydrazide;
(E)-3-Methoxy-N-methyl-N'-((8-methyl-6-(pyridin-3-yl)imidazo[1,2-a]pyridin-3-yl)methylene)benzenesulfonohydrazide;
(E)-N-methyl-N'-((8-methyl-6-(pyridin-3-yl)imidazo[1,2-a]pyridin-3-yl)methylene)-3-nitrobenzenesulfonohydrazide;
(E)-3-Chloro-N-methyl-N'-((8-methyl-6-(pyridin-3-yl)imidazo[1,2-a]pyridin-3-yl)methylene)benzenesulfonohydrazide;
(E)-N-methyl-N'-((8-methyl-6-(pyridin-3-yl)imidazo[1,2-a]pyridin-3-yl)methylene)-3-(trifluoromethyl)benzenesulfonohydrazide;
(E)-2-Bromo-4,6-difluoro-N-methyl-N'-((8-methyl-6-(pyridin-3-yl)imidazo[1,2-a]pyridin-3-yl)methylene)benzenesulfonohydrazide;
(E)-4-Chloro-N-methyl-N'-((8-methyl-6-(pyridin-3-yl)imidazo[1,2-a]pyridin-3-yl)methylene)-3-nitrobenzenesulfonohydrazide;
(E)-2-Bromo-4-fluoro-N-methyl-N'-((8-methyl-6-(pyridin-3-yl)imidazo[1,2-a]pyridin-3-yl)methylene)benzenesulfonohydrazide;
(E)-N'-((6-(1H-indol-2-yl)imidazo[1,2-a]pyridin-3-yl)methylene)-5-fluoro-N,2-dimethylbenzenesulfonohydrazide;
(E)-5-fluoro-N,2-dimethyl-N'-((6-(1-methyl-1H-indol-3-yl)imidazo[1,2-a]pyridin-3-yl)methylene)benzenesulfonohydrazide;
2-Cyano-N-methyl-N'((7-methyl-6-(pyridin-3-yl) imidazo[1,2-a]pyridin-3-yl)methylene) benzenesulfonohydrazide;
5-Fluoro-N, 2-dimethyl-N'-((7-methyl-6-(pyridin-3-yl) imidazo[1,2-a]pyridin-3-yl) methylene)benzenesulfonohydrazide;
N, 3-dimethyl-N'-((7-methyl-6-(pyridin-3-yl) imidazo[1,2-a]pyridin-3-yl) methylene)benzenesulfonohydrazide;
3-Fluoro-N-methyl-N'-((7-methyl-6-(pyridin-3-yl) imidazo[1,2-a]pyridin-3-yl)methylene) benzenesulfonohydrazide;
3-Chloro-N-methyl-N'-((7-methyl-6-(pyridin-3-yl)imidazo[1,2-a]pyridin-3-yl)methylene)benzenesulfonohydrazide;
N-methyl-N'-((7-methyl-6-(pyridin-3-yl) imidazo[1,2-a]pyridin-3-yl)methylene)-3-(trifluoromethyl)benzenesulfonohydrazide;
3-Bromo-N-methyl-N'((7-methyl-6-(pyridin-3-yl) imidazo[1,2-a]pyridin-3-yl) methylene)benzenesulfonohydrazide;
5-Fluoro-N, 2-dimethyl-N'-((7-methyl-6-(pyridin-3-yl)imidazo[1,2-a]pyridin-3-yl) methylene)benzenesulfonohydrazide;
N'-((6-(2,4-dimethoxypyrimidin-5-yl) imidazo[1,2-a]pyridin-3-yl)methylene)-5-fluoro-N, 2-dimethylbenzenesulfonohydrazide;
(E)-5-Fluoro-N,2-dimethyl-N'-((5-methyl-6-(pyridin-3-yl) imidazo[1,2-a]pyridin-3-yl)methylene)benzenesulfonohydrazide;
(E)-N,3-dimethyl-N'-((5-methyl-6-(pyridin-3-yl)imidazo[1,2-a]pyridin-3-yl)methylene)benzenesulfonohydrazide;
(E)-5-fluoro-N,2-dimethyl-N'-((6-(6-methylpyridin-3-yl)imidazo[1,2-a]pyridin-3-yl)methylene)benzenesulfonohydrazide;
(E)-N-methyl-N'-((6-(6-methylpyridin-3-yl)imidazo[1,2-a]pyridin-3-yl)methylene)-2-(trifluoromethoxy)benzenesulfonohydrazide;
(E)-5-Fluoro-2-methoxy-N-methyl-N'-((6-(6-methylpyridin-3-yl)imidazo[1,2-a]pyridin-3-yl)methylene)benzenesulfonohydrazide;
(E)-N,2-dimethyl-N'-((6-(6-methylpyridin-3-yl)imidazo[1,2-a]pyridin-3-yl)methylene)benzenesulfonohydrazide;
(E)-5-fluoro-N'-((6-(5-fluoropyridin-3-yl) imidazo[1,2-a]pyridin-3-yl)methylene)-N, 2-dimethylbenzenesulfonohydrazide;
(E)-5-Fluoro-N'-((6-(5-fluoropyridin-3-yl) imidazo[1,2-a]pyridin-3-yl)methylene)-2-methoxy-N-methylbenzenesulfonohydrazide;

(E)-5-Fluoro-N'-((6-(6-fluoro-5-methylpyridin-3-yl)imidazo[1,2-a]pyridin-3-yl)methylene)-N,2-dimethylbenzenesulfonohydrazide;
(E)-N'-((6-(6-Chloropyridins-3-yl)imidazo[1,2-a]pyridin-3-yl)methylene)-5-fluoro-N,2-dimethylbenzenesulfonohydrazide;
(E)-N'-((6-(1H-Pyrrol-2-yl)imidazo[1,2-a]pyridin-3-yl)methylene)-5-fluoro-N,2-dimethylbenzenesulfonohydrazide;
(E)-5-fluoro-N'-((6-(6-methoxypyridin-3-yl)imidazo[1,2-a]pyridin-3-yl)methylene)-N,2-dimethylbenzenesulfonohydrazide;
(E)-5-Fluoro-N-((6-(2-methoxypyrimidin-5-yl) imidazo[1,2-a]pyridine-3-yl)methylene)-N, 2-dimethylbenzenesulfonohydrazide;
(E)-5-fluoro-N, 2-dimethyl-N'-((6-(5-(trifluoromethyl)pyridin-3-yl) imidazo[1,2-a]pyridin-3-yl)methylene) benzenesulfonohydrazide;
(E)-5-Fluoro-N, 2-dimethyl-N'-((6-(pyrimidin-5-yl)imidazo[1,2-a]pyridin-3-yl)methylene)benzenesulfonohydrazide;
(E)-N-benzyl-1-methyl-2-((6-(pyridin-3-yl)imidazo[1,2-a]pyridin-3-yl)methylene)hydrazinecarboxamide;
(E)-1-methyl-2-((6-(pyridin-3-yl)imidazo[1,2-a]pyridin-3-yl)methylene)-N-p-tolylhydrazinecarboxamide;
(E)-N-(2-fluoro-5-methylphenyl)-1-methyl-2-((6-(pyridin-3-yl)imidazo[1,2-a]pyridin-3-yl)methylene)hydrazinecarboxamide;
(E)-N-(5-fluoro-2-methylphenyl)-1-methyl-2-((6-(pyridin-3-yl) imidazo[1,2-a]pyridin-3-yl)methylene)hydrazinecarboxamide;
N-benzyl-2-((6-bromoimidazo[1,2-a]pyridin-3-yl)methylene)-1-methylhydrazinecarboxamide;
(6-bromoimidazo[1,2-a]pyridin-3-yl)methylene)-N-(2-fluoro-5-methylphenyl)-1-methylhydrazinecarboxamide;
(6-bromoimidazo[1,2-a]pyridin-3-yl)methylene)-N-(5-fluoro-2-methylphenyl)-1-methylhydrazinecarboxamide;
(E)-1-methyl-N-(2-morpholinoethyl)-2-((6-(pyridin-3-yl) imidazo[1,2-a]pyridin-3-yl)methylene)hydrazinecarbothioamide;
(E)-N-(4-cyanophenyl)-1-methyl-2-((6-(pyridin-3-yl)imidazo[1,2-a]pyridin-3-yl)methylene)hydrazinecarbothioamide;
(E)-N-(4-methoxyphenyl)-1-methyl-2-((6-(pyridin-3-yl) imidazo[1,2-a]pyridin-3-yl)methylene)hydrazinecarbothioamide;
2-((6-bromoimidazo[1,2-a]pyridin-3-yl)methylene)-1-methyl-N-(2-morpholinoethyl) hydrazinecarbothioamide;
2-((6-bromoimidazo[1,2-a]pyridin-3-yl)methylene)-1-methyl-N-(4-(trifluoromethyl)phenyl) hydrazinecarbothioamide; or their pharmaceutically acceptable salts and solvates.

According to a further aspect of the present invention, there is provided a process for the preparation of a compound of formula (I)

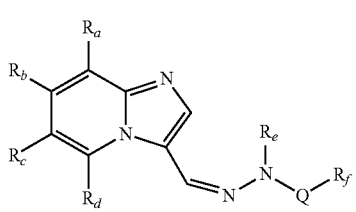

(I)

wherein, Q is $SO_2$; $R_a$, $R_b$ and $R_d$ are hydrogen or methyl; $R_c$, $R_e$ and $R_f$ are as defined for formula (I), which comprises, refluxing a compound of formula (3)

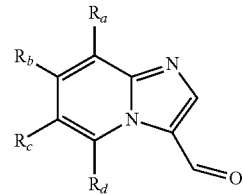

(3)

with a compound of formula $H_2N-NH-R_e$ in presence of alcoholic solvent followed by reacting with a compound of formula $R_fSO_2X$, wherein Q is $SO_2$; X is halogen, $R_a$, $R_b$ and $R_d$ are hydrogen or methyl, $R_c$, $R_e$ and $R_f$ are as defined above for formula (I) in presence of a base, such as pyridine; and optionally converting the resulting compound into a pharmaceutically acceptable salt.

According to a further aspect of the present invention, there is provided a process for the preparation of a compound of formula (I)

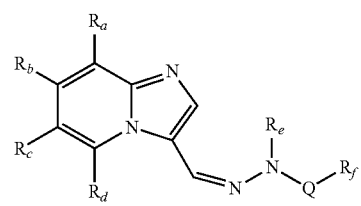

(I)

wherein, Q is $-C(O)NH$ or $-C(S)NH$; $R_a$, $R_b$ and $R_d$ are hydrogen or methyl, $R_c$, $R_e$ and $R_f$ are as defined for formula (I), which comprises, refluxing a compound of formula (3)

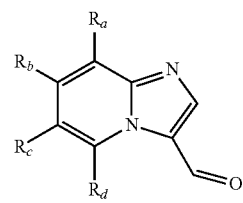

(3)

with a compound of formula $H_2N-NH-R_e$ in presence of an alcoholic solvent followed by reacting with a compound of formula $O=C=N-R_f$ or $S=C=N-R_f$, wherein $R_a$, $R_b$ and $R_d$ are hydrogen or methyl, $R_c$, $R_e$ and $R_f$ are as defined above for formula (I); and optionally converting the resulting compound into a pharmaceutically acceptable salt.

A convenient method for the synthesis of a compound of the present invention typically involves the series of steps described herein below:

The compounds of formula (I) are prepared using techniques known to one skilled in the art through the reaction sequences shown in the Schemes 1-2. Those with skill in the art will appreciate that the specific starting compounds and reagents, such as acids, bases, solvents, etc., identified in the schemes can be altered to prepare compounds encompassed by the present invention.

Schemes

The compounds of the present invention also include all stereoisomeric forms and mixtures thereof in all ratios and their pharmaceutically acceptable salts, solvates and polymorphs. Furthermore, all the compounds of the present invention are a subject of the present invention in the form of their prodrugs and other derivatives.

According to another aspect of present invention, the imidazo[1,2-a]pyridine derivatives of formula (I) can be prepared in a number of ways using methods well known to the person skilled in the art. Examples of methods to prepare the present compounds are described below and illustrated in Schemes 1 and 2 but are not limited thereto. It will be appreciated by persons skilled in the art that within certain of the processes described herein, the order of the synthetic steps employed may be varied and will depend inter alia on factors such as the nature of functional groups present in a particular substrate and the protecting group strategy (if any) to be adopted clearly, such factors will also influence the choice of reagent to be used in the synthetic steps. Although specific starting materials, reagents and reaction conditions are revealed in the schemes and the description below, other starting materials, reagents and reaction conditions can be used to obtain the compounds of formula (I).

The reagents, reactants and intermediates used in the following processes are either commercially available or can be prepared according to standard literature procedures known in the art. The starting compounds and the intermediates used for the synthesis of compounds of the present invention, are referred to with general symbols namely (1), (2), (3) and (4). The process used in schemes 1 and 2 of the present invention, is referred to with general symbols namely 1a, 1b, 1c, 1d, 1e, 1f and 1 g.

Processes for the preparation of compounds of the present invention are set forth in the following schemes:

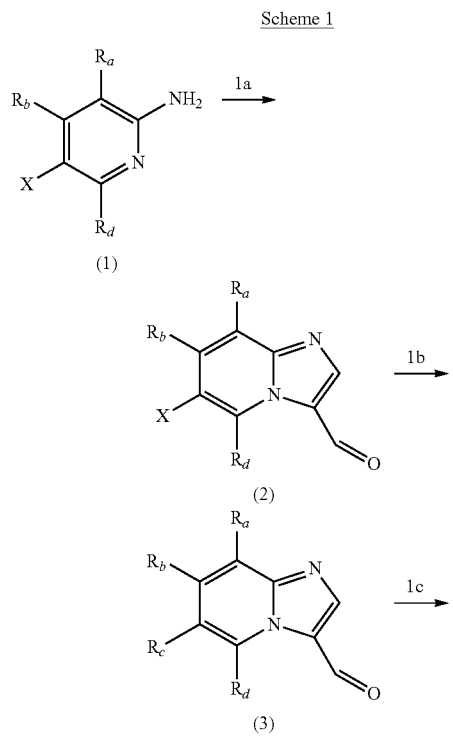

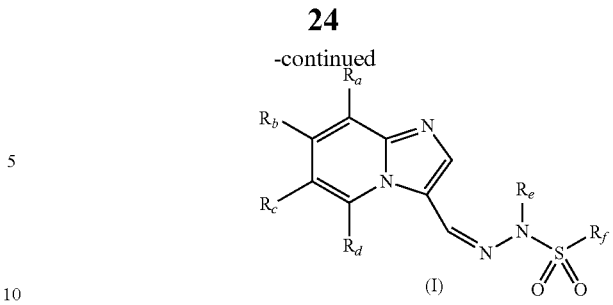

wherein X is halogen, $R_a$, $R_b$ and $R_d$ are hydrogen; $R_c$, $R_e$ and $R_f$ are as defined for formula (I).

Reaction Conditions

1a: HC(O)—CH(X)—CH(O), reflux, 1 to 2 hours;

1b: $R_c$—B(OH)$_2$, 100-120° C., 3 to 4 hours;

1c: a) H$_2$N—NH—$R_e$, reflux, 85° C., 2 to 3 hours;

b) $R_f$SO$_2$X, room temperature, 1 to 2 hours;

The compound of formula (2) can be prepared by refluxing compound of formula (I) with a compound of formula HC(O)—CH(X)—CH(O) in an appropriate solvent such as acetonitrile, dimethylformamide, dimethylsulfoxide or a mixture thereof. The compound of formula (2) can be refluxed with a boronic acid derivative of formula $R_c$—B(OH)$_2$ in presence of a base such as sodium carbonate, potassium carbonate, cesium carbonate, sodium bicarbonate, potassium bicarbonate or a mixture thereof and a catalyst such as dichlorobis(triphenylphosphine) palladium (II) in an appropriate solvent such as dimethylformamide, dimethylsulfoxide, tetrahydrofuran or a mixture thereof to form a compound of formula (3). The compound of formula (3) can be refluxed with a compound of formula H$_2$N—NH—$R_e$ in a polar solvent such as ethanol, methanol, isopropanol or mixture thereof to form the corresponding hydrazide. The hydrazide so formed can be treated with compound of formula $R_f$SO$_2$X in presence of a base, such as pyridine, triethylamine, ammonia or mixture thereof to form a compound of formula (I).

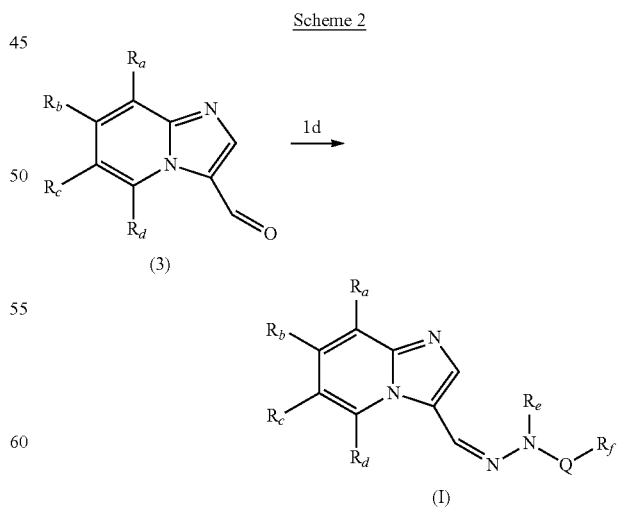

wherein, $R_a$, $R_b$ and $R_d$ are hydrogen or methyl; $R_c$ is halogen or heteroaryl; Q is —C(O)NH or —C(S)NH; $R_e$ and $R_f$ are as defined earlier for formula (I).

Reaction Conditions
1d: a) NH$_2$NH-Me, 85° C., 1.5 hours,
b) O=C=N—R$_f$ or S=C=N—R$_f$ reflux, 2 hours The compound of formula (3) can be reacted with methyl hydrazine in an appropriate solvent such as ethanol to obtain a hydrazine intermediate. The hydrazine so formed can be refluxed for about 2 hours with compound of formula O=C=N—R$_f$ or S=C=N—R$_f$ to obtain a compound of formula (I), wherein, R$_a$, R$_b$ and R$_d$ are hydrogen or methyl; R$_c$ is halogen or heteroaryl; Q is —C(O)NH or —C(S)NH and R$_e$ and R$_f$ are as defined earlier.

It will be appreciated by those skilled in the art that the compounds of the present invention may also be utilized in the form of their pharmaceutically acceptable salts or solvates. The pharmaceutically acceptable salts of the compounds of the present invention are non-toxic and can be used physiologically.

The pharmaceutically acceptable salts of the present invention can be synthesized from the subject compound, which contains a basic or an acidic moiety, by conventional chemical methods. Generally the salts are prepared by contacting the free base or acid with required amount of the desired salt-forming inorganic or organic acid or base in a suitable solvent or dispersant or from another salt by cation or anion exchange. Suitable solvents are, for example, ethyl acetate, ether, alcohols, acetone, tetrahydrofuran (THF), dioxane or mixtures of these solvents.

When the compounds of the present invention represented by the formula (I) contain one or more basic groups, i.e. groups which can be protonated, they can form an addition salt with an inorganic or organic acid. Examples of suitable inorganic acid salts include, but are not limited to, hydrochloride, hydrobromide, hydrofluoride, sulfate, sulfamate, phosphate, nitrate and bisulfate. Examples of suitable organic acid salts include, but are not limited to acetate, cinnamate, citrate, benzoate, benzenesulfonate, fumarate, maleate, malonate, methanesulfonate, oxalate, p-toluenesulfonate, succinate, tartrate, trifluoromethanesulfonate and valproate.

Thus, when the compounds of the present invention represented by the formula (I) contain an acidic group they can form an addition salt with a suitable base. For example, such salts of the compounds of the present invention may include their alkali metal salts such as Li, Na, and K salts, or alkaline earth metal salts like Ca, Mg salts, or aluminium salts, or salts with ammonia or salts of organic bases such as lysine, and arginine.

The pharmaceutically acceptable salts of the present invention can be synthesized from the subject compound, which contains a basic or an acidic moiety, by conventional chemical methods. Generally the salts are prepared by contacting the free base or acid with desired salt-forming inorganic or organic acid or base in a suitable solvent or dispersant or from another salt by cation or anion exchange. Suitable solvents are, for example, ethyl acetate, ether, alcohols, acetone, tetrahydrofuran (THF), dioxane or mixtures of these solvents.

The present invention furthermore includes all solvates of the compounds of the formula (I), for example hydrates, and the solvates formed with other solvents of crystallization, such as alcohols, ethers, ethyl acetate, dioxane, dimethylformamide (DMF), or a lower alkyl ketone, such as acetone, or mixtures thereof.

Methods of Treatment

The compounds of formula (I) are inhibitors of PI3K and/or mTOR and/or STAT3 and/or TNFα and/or IL-6 and find use in the treatment of benign or malignant tumors and/or inflammation.

The present invention further provides a method of inhibiting the tumor cell growth, tumor cell proliferation or tumorigenesis in a mammal comprising administering to a mammal in need of such treatment an effective amount of a compound of formula (I) or a pharmaceutically acceptable salt thereof.

Compounds of the present invention can be used to reduce, inhibit, or diminish the proliferation of tumor cells, and thereby assist in reducing the size of a tumor. Benign or malignant tumors that can be treated by compounds of formula (I) include, but are not limited to brain stem glioma, cerebellar astrocytoma, cerebral astrocytoma, brain tumors, glioblastoma, ependymoma, extracranial cancer, medulloblastoma, head & neck cancer, oral cancer, thyroid cancer, esophageal cancer, hypopharyngeal cancer, breast cancer, lung cancer including non-small-cell lung cancer and small-cell lung cancer, pancreatic cancer, lymphoma, melanoma, endometrial cancer, cervical cancer, liver cancer, intrahepatic bile duct, gastric cancer, bladder cancer, uterine cancer, colon cancer, colorectal cancer, ovarian cancer, prostate cancer, testicular cancer, leukemia, Ewing's sarcoma family of tumors, germ cell tumor, Hodgkin's disease, acute lymphoblastic leukemia, acute myeloid leukemia, adult acute myeloid leukemia, chronic myeloid leukemia, acute lymphocytic leukemia, chronic lymphocytic leukemia, hairy cell leukemia, human melanoma, neuroblastoma, non-Hodgkin's lymphoma, osteosarcoma, malignant fibrous histiocytoma of bone, retinoblastoma, rhabdomyosarcoma, soft tissue sarcomas, supratentorial primitive neuroectodermal and pineal tumors, visual pathway and hypothalamic glioma, Wilms' tumor, adult non-Hodgkin's lymphoma, kidney cancer, multiple myeloma, primary central nervous system lymphoma and skin cancer. Compounds of the formula (I) are also of use in the treatment of inflammatory diseases, for example psoriasis, contact dermatitis, atopic dermatitis, alopecia greata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, and other inflammatory or allergic conditions of the skin.

Compounds of the present invention may also be used for the treatment of other diseases or conditions, such as inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, septic shock, endotoxic shock, atherosclerosis, ischemia-reperfusion injury, coronary heart disease, vasculitis, amyloidosis, multiple sclerosis, sepsis, chronic recurrent uveitis, hepatitis C virus infection, malaria, ulcerative colitis, cachexia, psoriasis, plasmocytoma, endometriosis, Behcet's disease, Wegenrer's granulomatosis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, meningitis, ankylosing spondylitis, skin delayed type hypersensitivity disorders, Alzheimer's disease, systemic lupus erythematosus and allergic asthma.

According to another aspect of the present invention, there is provided a method for the treatment of diseases mediated by PI3K and/or mTOR and/or STAT3, comprising administering to a mammal in need thereof a therapeutically effective amount of a compound of formula (I) or a pharmaceutically acceptable salt or a pharmaceutically acceptable solvate thereof.

According to another aspect of the present invention, the disease mediated by PI3K and/or mTOR and/or STAT3 is cancer.

According to another aspect of the present invention, there is provided a method for the treatment of cancer, wherein the cancer is selected from the group comprising of brain stem glioma, cerebellar astrocytoma, cerebral astrocytoma, brain tumors, glioblastoma, ependymoma, extracranial cancer, medulloblastoma, head & neck cancer, oral cancer, thyroid cancer, hypopharyngeal cancer, breast cancer, endometrial cancer, leukemia, lung cancer including non-small-cell lung cancer and small-cell lung cancer, pancreatic cancer, lymphoma, melanoma, cervical cancer, liver cancer, gastric cancer, bladder cancer, uterine cancer colon cancer, colorectal cancer, ovarian cancer, prostate cancer, testicular cancer, Ewing's sarcoma family of tumors, germ cell tumor, Hodgkin's disease, acute lymphoblastic leukemia, acute myeloid leukemia, adult acute myeloid leukemia, chronic myeloid leukemia, acute lymphocytic leukemia, chronic lymphocytic leukemia, hairy cell leukemia, human melanoma, neuroblastoma, non-Hodgkin's lymphoma, osteosarcoma, malignant fibrous histiocytoma of bone, retinoblastoma, rhabdomyosarcoma, soft tissue sarcomas, supratentorial primitive neuroectodermal and pineal tumors, visual pathway and hypothalamic glioma, Wilms' tumor, adult non-Hodgkin's lymphoma, esophageal cancer, kidney cancer, multiple myeloma, primary central nervous system lymphoma and skin cancer comprising administering to a mammal in need thereof a therapeutically effective amount of a compound of formula (I) or a pharmaceutically acceptable salt or a pharmaceutically acceptable solvate thereof.

According to another aspect of the present invention, there is provided a method for the treatment of cancer, wherein the cancer is selected from the group comprising of glioblastoma, hypopharyngeal cancer, lung cancer, including non-small-cell lung cancer and small-cell lung cancer, breast cancer, pancreatic cancer, colon cancer, cervical cancer, prostate cancer, ovarian cancer, multiple myeloma and human melanoma comprising administering to a mammal in need thereof a therapeutically effective amount of a compound of formula (I) or a pharmaceutically acceptable salt or a pharmaceutically acceptable solvate thereof.

According to further aspect of the present invention, there is provided a method for the treatment of diseases mediated by TNF-α and/or IL-6, comprising administering to a mammal in need thereof a therapeutically effective amount of a compound of formula (I) or a pharmaceutically acceptable salt or a pharmaceutically acceptable solvate thereof.

According to another aspect of the present invention, there is provided a method for the treatment of diseases mediated by TNF-α and/or IL-6 selected from the group comprising of psoriasis, contact dermatitis, atopic dermatitis, alopecia greata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, inflammatory bowel disease, inflammation, rheumatoid arthritis, chronic non-rheumatoid arthritis, osteoporosis/bone resorption, Crohn's disease, septic shock, endotoxic shock, atherosclerosis, ischaemia-reperfusion injury, coronary heart disease, vasculitis, amyloidosis, multiple sclerosis, sepsis, chronic recurrent uveitis, hepatitis C virus infection, malaria, ulcerative colitis, cachexia, plasmocytoma, endometriosis, Behcet's disease, Wegenrer's granulomatosis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, meningitis, ankylosing spondylitis, skin delayed type hypersensitivity disorders, Alzheimer's disease, systemic lupus erythematosus and allergic asthma, comprising administering to a mammal in need thereof a therapeutically effective amount of a compound of formula (I) or a pharmaceutically acceptable salt or a pharmaceutically acceptable solvate thereof.

According to another aspect of the present invention, there is provided a method for the treatment of diseases mediated by TNF-α and/or IL-6 selected from the group comprising of rheumatoid arthritis, Crohn's disease, ulcerative colitis, septic shock, psoriasis and atherosclerosis, comprising administering to a mammal in need thereof a therapeutically effective amount of a compound of formula (I) or a pharmaceutically acceptable salt or a pharmaceutically acceptable solvate thereof.

According to another aspect of the present invention, there is provided a method for the treatment of inflammatory diseases such as rheumatoid arthritis, Crohn's disease, ulcerative colitis, septic shock syndrome, psoriasis and atherosclerosis comprising administering to a mammal in need thereof a therapeutically effective amount of a compound of formula (I) or a pharmaceutically acceptable salt or a pharmaceutically acceptable solvate thereof.

According to another aspect of the present invention, there is provided the use of a compound of formula (I) or a pharmaceutically acceptable salt thereof containing either entity for the manufacture of a medicament for the treatment of diseases mediated by PI3K and/or mTOR.

According to another aspect of the present invention, there is provided the use of a compound of formula (I) or a pharmaceutically acceptable salt thereof containing either entity for the manufacture of a medicament for the treatment of cancers wherein the cancer is selected from the group comprising of brain stem glioma, cerebellar astrocytoma, cerebral astrocytoma, brain tumors, glioblastoma, ependymoma, extracranial cancer, medulloblastoma, head & neck cancer, oral cancer, thyroid cancer, hypopharyngeal cancer, breast cancer, endometrial cancer, leukemia, lung cancer including non-small-cell lung cancer and small-cell lung cancer, pancreatic cancer, lymphoma, melanoma, cervical cancer, liver cancer, gastric cancer, bladder cancer, uterine cancer colon cancer, colorectal cancer, ovarian cancer, prostate cancer, testicular cancer, Ewing's sarcoma family of tumors, germ cell tumor, Hodgkin's disease, acute lymphoblastic leukemia, acute myeloid leukemia, adult acute myeloid leukemia, chronic myeloid leukemia, acute lymphocytic leukemia, chronic lymphocytic leukemia, hairy cell leukemia, human melanoma, neuroblastoma, non-Hodgkin's lymphoma, osteosarcoma, malignant fibrous histiocytoma of bone, retinoblastoma, rhabdomyosarcoma, soft tissue sarcomas, supratentorial primitive neuroectodermal and pineal tumors, visual pathway and hypothalamic glioma, Wilms' tumor, adult non-Hodgkin's lymphoma, esophageal cancer, kidney cancer, multiple myeloma, primary central nervous system lymphoma and skin cancer.

According to another aspect of the present invention, there is provided the use of a compound of formula (I) or a pharmaceutically acceptable salt thereof for the manufacture of a medicament containing either entity for the treatment of cancers such as glioblastoma, hypopharyngeal cancer, lung cancer, including non-small-cell lung cancer and small-cell lung cancer, breast cancer, pancreatic cancer, colon cancer, cervical cancer, prostate cancer, ovarian cancer, multiple myeloma and human melanoma.

According to another aspect of the present invention there is provided the use of compound of formula (I) or a pharmaceutically acceptable salt thereof for the manufacture of a medicament containing either entity for the treatment of diseases mediated by TNF-α and/or IL-6.

According to another aspect of the present invention there is provided the use of compound of formula (I) or a pharmaceutically acceptable salt thereof for the manufacture of a medicament containing either entity for the treatment of diseases selected from the group comprising of psoriasis, contact dermatitis, atopic dermatitis, alopecia greata, erythema multiforme, dermatitis herpetiformis, scleroderma, vitiligo, hypersensitivity angiitis, urticaria, bullous pemphigoid, lupus erythematosus, pemphigus, epidermolysis bullosa acquisita, inflammatory bowel disease, inflammation, rheumatoid arthritis, chronic non-rheumatoid arthritis, osteoporosis/bone resorption, Crohn's disease, septic shock, endotoxic shock, atherosclerosis, ischaemia-reperfusion injury, coronary heart disease, vasculitis, amyloidosis, multiple sclerosis, sepsis, chronic recurrent uveitis, hepatitis C virus infection, malaria, ulcerative colitis, cachexia, plasmocytoma, endometriosis, Behcet's disease, Wegenrer's granulomatosis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, meningitis, ankylosing spondylitis, skin delayed type hypersensitivity disorders, Alzheimer's disease, systemic lupus erythematosus and allergic asthma.

According to another aspect of the present invention, there is provided the use of a compound of formula (I) or a pharmaceutically acceptable salt thereof for the manufacture of a medicament for the treatment of cancer mediated by STAT3.

According to another aspect of the present invention, there is provided the use of a compound of formula (I) or a pharmaceutically acceptable salt thereof for the manufacture of a medicament containing either entity for the treatment of inflammatory diseases such as rheumatoid arthritis, Crohn's disease, ulcerative colitis, septic shock syndrome, psoriasis and atherosclerosis.

According to another aspect of the present invention there are provided methods for the manufacture of medicaments comprising compounds of formula (I), which are useful for the treatment of cancers such as glioblastoma, hypopharyngeal cancer, lung cancer, including non-small-cell lung cancer and small-cell lung cancer, breast cancer, pancreatic cancer, colon cancer, cervical cancer, prostate cancer, ovarian cancer, multiple myeloma and human melanoma According to another aspect of the present invention there are provided methods for manufacture of medicaments comprising compounds of formula (I), which are useful for the treatment of inflammation, including diseases such as rheumatoid arthritis, Crohn's disease, ulcerative colitis, septic shock syndrome, psoriasis and atherosclerosis.

Pharmaceutical Compositions and Methods

According to another aspect of the present invention there are provided pharmaceutical compositions comprising the compound of formula (I) as active ingredients, useful in the treatment of cancer and inflammation.

The pharmaceutical preparations according to the invention are prepared in a manner known per se and familiar to one skilled in the art. Pharmaceutically acceptable inert inorganic and/or organic carriers and/or additives can be used in addition to the compounds of formula (I), and/or their physiologically tolerable salts. For the production of pills, tablets, coated tablets and hard gelatin capsules it is possible to use, for example, lactose, corn starch or derivatives thereof, gum arabica, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

The pharmaceutical preparations normally contain about 1 to 99%, for example, about 5 to 70%, or from about 5 to about 30% by weight of the compound of the formula (I) and/or its physiologically tolerable salt. The amount of the active ingredient of the formula (I) and/or its physiologically tolerable salt in the pharmaceutical preparations normally is from about 1 to 1000 mg.

The dose of the compounds of this invention, which is to be administered, can cover a wide range. The dose to be administered daily is to be selected to suit the desired effect. A suitable dosage is about 0.001 to 100 mg/kg/day of the compound of formula (I) and/or their physiologically tolerable salt, for example, about 0.01 to 50 mg/kg/day of a compound of formula (I) or a pharmaceutically acceptable salt of the compound. If required, higher or lower daily doses can also be administered. Actual dosage levels of the active ingredients in the pharmaceutical compositions of this invention may be varied so as to obtain an amount of the active ingredient, which is effective to achieve the desired therapeutic response for a particular patient, composition, and mode of administration without being toxic or resulting in unacceptable side effects to the patient.

The pharmaceuticals can be administered orally, for example in the form of pills, tablets, coated tablets, lozenges, capsules, dispersible powders or granules, suspensions, emulsions, syrups or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions, ointments, gels, lotions or transdermally, for example, in the form of transdermal patches, or in other ways, for example in the form of aerosols or nasal sprays.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

In addition to the active ingredient of the formula (I) and/or its physiologically acceptable salt and carrier substances, the pharmaceutical preparations can contain additives such as, for example, fillers, antioxidants, dispersants, emulsifiers, defoamers, flavors, preservatives, solubilizers or colorants. They can also contain two or more compounds of the formula (I) and/or their physiologically tolerable salts. Furthermore, in addition to at least one compound of the formula (I) and/or its physiologically tolerable salt, the pharmaceutical preparations can also contain one or more other therapeutically or prophylactically active ingredients.

By "pharmaceutically acceptable" it is meant the carrier, diluent, excipients, and/or salt must be compatible with the other ingredients of the formulation, and not deleterious to the recipient thereof.

It is understood that modifications that do not substantially affect the activity of the various embodiments of this invention are included within the invention disclosed herein. Accordingly, the following examples are intended to illustrate but not to limit the present invention.

EXPERIMENTAL

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims. Unless otherwise stated all temperatures are in degree Celsius. Also, in these examples and elsewhere, abbreviations have the following meanings:

| List of abbreviations | |
| --- | --- |
| $CO_2$ | Carbon dioxide |
| $CHCl_3$ | Chloroform |
| $DCM/CH_2Cl_2$ | Dichloromethane |
| DMEM | Dulbecco's Modified Eagle Medium |
| DMF | Dimethyl formamide |
| DMSO | Dimethyl sulfoxide |
| EtOAc | Ethyl acetate |
| FCS | Fetal calf serum |
| FBS | Fetal Bovine Serum |
| g | Gram |
| HCl | Hydrochloric acid |
| Hepes | N-2-Hydroxyethylpiperazine-N'-2-ethanesulfonic acid |
| $H_2$ | Hydrogen |
| $H_2SO_4$ | Sulphuric acid |
| MeOH | Methanol |
| mL | Milliliter |
| $MgCl_2$ | Magnesium chloride |
| mmol | Millimoles |
| MTS | (3-(4,5-Dimethylthiazol-2-yl)-5-(3-carboxymethoxyphenyl)-2-(4-sulfonyl)-2H-tetrazolium) |
| $Na_2CO_3$ | Sodium carbonate |
| $NaHCO_3$ | Sodium bicarbonate |
| NaOH | Sodium hydroxide |
| NaH | Sodium hydride |
| $Na_2SO_4$ | Sodium sulphate |
| PBS | Phosphate buffer saline |
| Pet ether | Petroleum ether |
| $POCl_3$ | Phosphorus oxychloride |
| RPMI | Roswell Park Memorial Institute |
| RT | Room Temperature (20-30° C.) |
| THF | Tetrahydrofuran |

Intermediate 1

6-(pyridin-3-yl)imidazo[1,2-a]pyridine-3-carbaldehyde

Step 1: 6-bromoimidazo[1,2-a]pyridine-3-carbaldehyde Bromomalonaldehyde (5230 mg, 34.68 mmol) was added to a solution of 5-bromopyridin-2-amine in acetonitrile (5000 mg, 28.90 mmol). The reaction mixture was refluxed for 2 hours. After completion of the reaction, the reaction mixture was quenched with sodium bicarbonate solution and extracted with EtOAc. The organic layer was washed with brine and dried over sodium sulfate. The organic layer was concentrated in vacuo and the product was purified by column chromatography using EtOAc-petroleum ether gradient to obtain the title compound. Yield: 53%; $^1$H NMR (DMSO-$d_6$; 300 MHz): δ 9.94 (s, 1H), 9.50 (s, 1H), 8.54 (s, 1H), 7.86-7.85 (m, 2H); MS (m/z): 226 (M+1)$^+$.

Step 2: 6-(pyridin-3-yl)imidazo[1,2-a]pyridine-3-carbaldehyde 6-bromoimidazo[1,2-a]pyridine-3-carbaldehyde (Compound of step 1, 4000 mg, 17.77 mmol), Pyridine-3-boronic acid (3280 mg, 26.66 mmol), dichlorobis(triphenylphosphine) palladium (II) (800 mg, 20% mmol) and 2M aqueous $Na_2CO_3$ (14 mL) were added to DMF (50 mL) and refluxed for 2 hours. The reaction mixture was diluted with EtOAc and washed with $H_2O$ and brine. The solvent was evaporated to obtain oil, which was purified by column chromatography (silica gel, 1% MeOH in $CHCl_3$) to obtain the title compound. Yield: 62%; $^1$HNMR (DMSO-$d_6$; 300 MHz): δ 9.96 (s, 1H), 9.59 (s, 1H), 8.92 (s, 1H), 8.63-8.61 (d, 1H), 8.55 (s, 1H), 8.15-8.11 (d, 1H), 8.06-7.96 (m, 2H), 7.56-7.51 (M, 1H); MS: m/z 224 (M+1)$^+$.

6-(pyridin-4-yl)imidazo[1,2-a]pyridine-3-carbaldehyde was prepared by following the procedure as described for Intermediate 1, except that Pyridine-4-boronic acid was used in place of Pyridine-3-boronic acid.

Intermediate 2

6-(6-fluoropyridin-3-yl)imidazo[1,2-a]pyridine-3-carbaldehyde

The title compound was prepared by following the process as described for Intermediate 1. 6-fluoropyridin-3-ylboronic acid (68.88 mg, 0.488 mmol) was used instead of pyridine-3-boronic acid. Yield: 50%; $^1$H NMR (DMSO-$d_6$; 300 MHz): δ 9.99 (s, 1H), 9.60 (s, 1H), 8.61-8.62 (d, 1H, J=1.8 Hz), 8.58 (s, 1H), 8.34-8.37 (dd, 1H, J=3 Hz, 6 Hz), 7.99-8.04 (m, 2H), 7.35-7.38 (dd, 1H, J=3 Hz); MS: m/z 242 (M+1)$^+$.

Intermediate 3

6-(2-fluoropyridin-3-yl)imidazo[1,2-a]pyridine-3-carbaldehyde

The title compound was prepared by following the process as described for Intermediate 1. 2-fluoropyridin-3-ylboronic acid (71 mg, 0.462 mmol) was used instead of pyridine-3-boronic acid. Yield: 45%; $^1$H NMR (DMSO-$d_6$; 300 MHz): 9.99 (s, 1H), 9.66 (s, 1H), 8.62 (s, 1H), 8.28-8.33 (m, 2H), 7.99-8.02 (m, 2H), 7.56 (s, 1H); MS: m/z 242 (M+1)$^+$.

Intermediate 4

6-(Quinolin-3-yl)imidazo[1,2-a]pyridine-3-carbaldehyde

The title compound was prepared by following the process as described for Intermediate 1. Quinolin-3-ylboronic acid (84.6 mg, 0.488 mmol) was used instead of pyridine-3-boronic acid. Yield: 66%; $^1$H NMR (DMSO-$d_6$; 300 MHz): 10.01 (s, 1H), 9.88 (s, 1H), 9.19-9.20 (d, 1H, J=2.4 Hz), 8.39 (s, 2H), 8.16-8.19 (d, 1H, J=8.4 Hz), 7.94-7.95 (m, 2H), 7.76-7.82 (m, 1H), 7.62-7.67 (t, 1H, J=7.8 Hz, 7.2 Hz), 7.50-7.52 (m, 1H); MS: m/z 274(M+1)$^+$.

Intermediate 5

8-methyl-6-(pyridin-3-yl)imidazo[1,2-a]pyridine-3-carbaldehyde

Step 1: 6-bromo-8-methylimidazo[1,2-a]pyridine-3-carbaldehyde

The title compound was prepared by following the procedure as described for step 1 of Intermediate 1. 5-bromo-3-methylpyridin-2-amine (500 mg, 2.673 mmol) was used instead of 5-bromopyridin-2-amine in acetonitrile to obtain the title compound.

Yield: 52%; $^1$H NMR (CDCl$_3$; 300 MHz): δ 9.961 (s, 1H), 9.557 (s, 1H), 8.298 (s, 1H), 7.484 (s, 1H), 2.711 (s, 3H); MS: m/z 239 (M+1)$^+$ Step 2: 8-methyl-6-(pyridin-3-yl) imidazo[1,2-a]pyridine-3-carbaldehyde The title compound was prepared by following the process as described for step 2 of Intermediate 1. 6-Bromo-8-methylimidazo[1,2-a]pyridine-3-carbaldehyde (150 mg, 0.630 mmol) was used instead of 6-bromoimidazo[1,2-a]pyridine-3-carbaldehyde.

Yield: 60%; $^1$H NMR (CDCl$_3$; 300 MHz): δ 10.00 (s, 1H), 9.63 (s, 1H), 8.91 (s, 1H), 8.70 (s, 1H), 8.37 (s, 1H), 7.95 (d, 1H, J=5.7 Hz), 7.62 (s, 1H), 7.46 (s, 1H), 2.79 (s, 3H); MS: m/z 236 (M+1)$^+$.

Intermediate 6

Tert-butyl 2-(3-formylimidazo[1,2-a]pyridin-6-yl)-1H-indole-1-carboxylate 6-bromoimidazo[1,2-a]pyridine-3-carbaldehyde (step 1 of Intermediate 1, 150 mg, 0.6729 mmol), 1-(tert-butoxycarbonyl)-1H-indol-2-ylboronic acid (228 mg, 0.8742 mmol), dichlorobis(triphenylphosphine) palladium (II) (30 mg, 20% mmol) and 2M aqueous Na$_2$CO$_3$ (1 mL) were added to DMF (5 mL) and refluxed for 2 h. The reaction mixture was diluted with EtOAc and washed with water and brine. The solvent was evaporated to obtain solid residue, which was purified by column chromatography (silica gel, 1% methanol in chloroform) to obtain the title compound. Yield: 51%; $^1$H NMR (DMSO-d$_6$; 300 MHz): δ 11.91 (s, 1H), 9.99 (s, 1H), 9.81 (s, 1H), 8.55 (s, 1H), 8.17 (dd, 1H, J=9.3, 1.8 Hz), 7.95 (d, 1H, J=9.3 Hz), 7.56 (d, 1H, J=7.8 Hz), 7.43 (d, 1H, J=8.4 Hz), 7.142 (t, 1H, J=7.2 Hz), 7.03 (m, 2H); MS: m/z 260 (M−1)$^+$.

Intermediate 7

7-methyl-6-(pyridin-3-yl) imidazo[1,2-a]pyridine-3-carbaldehyde

Step 1: 6-bromo-7-methylimidazo[1,2-a]pyridine-3-carbaldehyde 1402-67

Bromomalonaldehyde (5000 mg, 26.74 mmol) was added to a solution of 5-bromo-4-methylpyridin-2-amine in acetonitrile (5250 mg, 34.76 mmol). The reaction mixture was refluxed for 2 hours. After completion of the reaction, the reaction mixture was quenched with sodium bicarbonate solution and extracted with ethyl acetate. The organic layer was washed with brine and dried over sodium sulfate. The organic layer was concentrated in vacuum and the product was purified by column chromatography using ethyl acetate-petroleum ether gradient to obtain the title compound. Yield: 79.81%; $^1$H NMR (DMSO-d$_6$; 300 MHz): δ 9.90 (s, 1H), 9.52 (s, 1H), 8.51 (s, 1H), 7.94 (s, 1H), 2.50 (s, 3H); MS (m/z): 239 (M+1)$^+$.

Step 2: 7-methyl-6-(pyridin-3-yl) imidazo[1,2-a]pyridine-3-carbaldehyde 6-bromo-7-methylimidazo[1,2-a]pyridine-3-carbaldehyde (Compound of step 1, 2000 mg, 7.90 mmol), Pyridine-3-boronic acid (1170 mg, 9.49 mmol), dichlorobis (triphenylphosphine) palladium (II) (200 mg, 10% mmol) and 2M aqueous Na$_2$CO$_3$ (7 mL) were added to DMF (25 mL) and refluxed for 2 hours. The reaction mixture was diluted with ethyl acetate and washed with H$_2$O and brine. The solvent was evaporated to obtain crude product, which was purified by column chromatography (silica gel, 1% methanol in chloroform) to obtain the title compound. Yield: 62%; $^1$H NMR (DMSO-d$_6$; 300 MHz): δ 9.92 (s, 1H), 9.20 (s, 1H), 8.69-8.70 (m, 2H), 8.54 (s, 1H), 7.95-7.99 (m, 1H), 7.90 (s, 1H), 7.53-7.58 (m, 1H), 2.34 (s, 3H); MS: m/z 238 (M+1)+

Intermediate 8

6-(2,4-dimethoxypyrimidin-5-yl) imidazo[1,2-a]pyridine-3-carbaldehyde 1402-159

6-bromoimidazo[1,2-a]pyridine-3-carbaldehyde (Compound of step 1 of Intermediate 1, 200 mg, 0.89 mmol), 2,4-dimethoxypyrimidin-5-ylboronic acid (212.57 mg, 1.15 mmol), dichlorobis(triphenylphosphine) palladium (II) (20 mg, 10% mmol) and 2M aqueous Na$_2$CO$_3$ (1 mL) were added to DMF (8 mL) and refluxed for 3 hours. The reaction mixture was diluted with ethyl acetate and washed with H$_2$O and brine. The solvent was evaporated to obtain crude product, which was purified by column chromatography (silica gel, 1% methanol in chloroform) to obtain the title compound. Yield: 47.43%; $^1$H NMR (DMSO-d$_6$; 300 MHz): δ 9.97 (s, 1H), 9.59 (s, 1H), 8.56-8.58 (d, 2H, J=4.5 Hz), 7.88-7.98 (m, 2H), 3.96 (s, 3H), 3.98 (s, 3H); MS: m/z 285.1 (M+1)+

Intermediate 9

5-Methyl-6-(pyridin-3-yl) imidazo[1,2-a]pyridine-3-carbaldehyde

Step 1: 6-bromo-5-methylimidazo[1,2-a]pyridine-3-carbaldehyde

Bromomalonaldehyde (464 mg, 3.07 mmol) was added to a solution of 5-bromo-6-methylpyridin-2-amine (500 mg, 2.67 mmol) in acetonitrile. The reaction mixture was refluxed for 1 hour. After completion of the reaction, the reaction mixture was quenched with sodium bicarbonate solution and extracted with ethyl acetate. The organic layer was washed with brine and dried over sodium sulfate. The organic layer was concentrated and the product was purified by column chromatography using up to 0.5% methanol in chloroform gradient to obtain the title compound. Yield: 28%; $^1$H NMR (DMSO-d$_6$; 300 MHz): δ 10.06 (s, 1H), 8.51 (s, 1H), 7.86-7.83 (d, 1H, J=9.3 Hz), 7.68 (d, 1H, J=9.3 Hz), 3.03 (s, 3H); MS: m/z 240.1 (M+1)$^+$.

Step 2: 5-Methyl-6-(pyridin-3-yl) imidazo[1,2-a]pyridine-3-carbaldehyde 6-bromo-5-methylimidazo[1,2-a]pyridine-3-carbaldehyde (125 mg, 0.523 mmol), Pyridine-3-boronic acid (77.5 mg, 0.603 mmol), dichlorobis(triphenylphosphine) palladium (II) (36.7 mg, 0.05 mmol) and 2M aqueous Na$_2$CO$_3$ (2 ml) were dissolved in DMF (3 ml) and refluxed for 2 hours. The reaction mixture was diluted with ethyl acetate and washed with water and brine. The solvent was evaporated to obtain crude product, which was purified by column chromatography (silica gel, 0.5% methanol in chloroform) to obtain the title compound. Yield: 40%; $^1$H NMR (DMSO-$d_6$; 300 MHz): 69.90(s, 1H), 8.39 (s, 1H), 7.73 (d, 1H, J=9.6 Hz), 7.56 (d, 1H, J=9.3 Hz), 3.11 (s, 3H); MS: m/z 238 (M+1)$^+$.

Intermediate 10

6-(6-methylpyridin-3-yl) imidazo[1,2-a]pyridine-3-carbaldehyde

The title compound was prepared by following the procedure as described for Intermediate 1 using 6-bromoimidazo[1,2-a]pyridine-3-carbaldehyde and 6-methylpyridin-3-ylboronic acid. Yield: 40%; $^1$H NMR (DMSO-$d_6$; 300 MHz): δ 10.0 (s, 1H), 9.74 (s, 1H), 8.79 (d, 1H, J=1.8 Hz), 8.38 (s, 1H), 7.93-7.78 (m, 4H), 7.33 (d, 1H, J=8.1 Hz), 2.66 (s, 3H); MS: m/z 238(M+1)$^+$.

Intermediate 11

6-(5-fluoropyridin-3-yl) imidazo[1,2-a]pyridine-3-carbaldehyde

The title compound was prepared by following the procedure as described for Intermediate 1 using 6-bromoimidazo[1,2-a]pyridine-3-carbaldehyde and 5-fluoropyridin-3-ylboronic acid. Yield: 52%; $^1$H NMR (DMSO-$d_6$; 300 MHz): δ 10.01 (s, 1H), 9.66 (s, 1H), 8.84 (s, 1H), 8.66-8.67 (d, 1H, J=2.1 Hz), 8.59 (s, 1H), 8.18-8.21 (d, 1H, J=9 Hz), 8.08-8.11 (d, 1H, J=9.6 Hz), 8.03 (s, 1H); MS: m/z 241.6 (M+1)$^+$.

Intermediate 12

6-(6-fluoro-5-methylpyridin-3-yl) imidazo[1,2-a]pyridine-3-carbaldehyde

The title compound was prepared by following the procedure as described for Intermediate 1 using 6-bromoimidazo[1,2-a]pyridine-3-carbaldehyde and 6-fluoro-5-methylpyridin-3-ylboronic acid. Yield: 44%; $^1$H NMR (DMSO-$d_6$; 300 MHz): δ10.0 (s, 1H), 9.59 (s, 1H), 8.58-8.00 (m, 5H), 2.24 (s, 3H), MS: m/z 256(M+1)$^+$.

Intermediate 13

6-(6-chloropyridin-3-yl) imidazo[1,2-a]pyridine-3-carbaldehyde

The title compound was prepared by following the procedure as described for Intermediate 1 using 6-bromoimidazo[1,2-a]pyridine-3-carbaldehyde and 6-chloropyridin-3-ylboronic acid. Yield: 44%; $^1$H NMR (DMSO-$d_6$; 300 MHz): δ 10.02 (s, 1H), 9.76 (s, 1H), 8.68 (s, 1H), 8.40 (s, 1H), 7.93 (bs, 2H), 7.79 (d, 1H, J=9 Hz), 7.52 (d, 1H, J=8.1 Hz); MS: m/z 258(M+1)$^+$.

Intermediate 14

6-(1H-pyrrol-2-yl)imidazo[1,2-a]pyridine-3-carbaldehyde

The title compound was prepared by following the procedure as described for Intermediate 1 using 6-bromoimidazo[1,2-a]pyridine-3-carbaldehyde and 1H-pyrrol-2-ylboronic acid.

Yield: 21%; $^1$H NMR (DMSO-$d_6$; 300 MHz): δ 11.69 (s, 1H), 9.94 (s, 1H), 9.58 (s, 1H), 8.48 (s, 1H), 8.00-7.86 (m, 2H), 6.94 (s, 1H), 6.61 (s, 1H), 6.18 (s, 1H); MS: m/z 212 (M+1).

Intermediate 15

6-(2-methoxypyrimidin-5-yl) imidazo[1,2-a]pyridine-3-carbaldehyde

The title compound was prepared by following the procedure as described for Intermediate 1 using 6-bromoimidazo[1,2-a]pyridine-3-carbaldehyde and 2-methoxypyrimidin-5-ylboronic acid. Yield: 55.55%; $^1$H NMR (DMSO-$d_6$; 300 MHz): δ 10.01 (s, 1H), 9.62 (s, 1H), 9.00 (s, 2H), 8.59 (s, 1H), 8.04-8.05 (m, 2H), 3.99 (s, 3H); MS: m/z 254 (M+1)$^+$.

Intermediate 16

6-(5-(trifluoromethyl)pyridin-3-yl) imidazo[1,2-a]pyridine-3-carbaldehyde

The title compound was prepared by following the procedure as described for Intermediate 1 using 6-bromoimidazo[1,2-a]pyridine-3-carbaldehyde and 5-(trifluoromethyl)pyridin-3-ylboronic acid. Yield: 48%; $^1$H NMR (DMSO-$d_6$; 300 MHz): δ 10.04 (s, 1H), 9.71 (s, 1H), 9.27 (s, 1H), 9.07 (s, 1H), 8.62 (s, 2H), 8.16-8.19 (dd, 1H, J=1.8&9.3 Hz), 8.03-8.04 (d, 1H, J=9.3 Hz); MS: m/z 292 (M+1)$^+$.

Intermediate 17

6-(pyrimidin-5-yl) imidazo[1,2-a]pyridine-3-carbaldehyde

The title compound was prepared by following the procedure as described for Intermediate 1 using 6-bromoimidazo[1,2-a]pyridine-3-carbaldehyde and pyrimidin-5-ylboronic acid.

Yield: 50%; $^1$H NMR (DMSO-$d_6$; 300 MHz): δ 10.01 (s, 1H), 9.77-9.79 (m, 1H), 9.29-9.32 (m, 1H), 9.04 (s, 2H), 8.39-8.40 (m, 1H), 7.94-7.99 (m, 1H), 7.78-7.82 (dd, 1H, J=1.8 &9.3 Hz); MS: m/z 224 (M+1)$^+$.

Intermediate 18

6-Bromoimidazo[1,2-a]pyrimidine-3-carbaldehyde 1402-113

Bromomalonaldehyde (500 mg, 2.90 mmol) was added to a solution of 5-bromopyrimidin-2-amine (526 mg, 3.49 mmol) in acetonitrile. The reaction mixture was refluxed for 2 hours. After completion of the reaction, the reaction mixture was quenched with sodium bicarbonate solution and extracted with ethyl acetate. The organic layer was washed with brine and dried over sodium sulfate. The organic layer was concentrated and the product was purified by column chromatography using up to 2% methanol in chloroform gradient to obtain the title compound. Yield: 40%; $^1$H NMR (DMSO-$d_6$; 300 MHz): δ 9.98(s, 1H), 9.75-9.76 (d, 1H, J=2.4 Hz), 8.97-8.98 (d, 1H, 2.4 Hz), 8.70 (s, 1H); MS (m/z): 226 (M+1)$^+$.

EXAMPLES

Example 1

N-methyl-N'-((6-(pyridin-3-yl)imidazo[1,2-a]pyridin-3-yl)methylene)benzenesulfonohydrazide

To a solution of 6-(pyridin-3-yl)imidazo[1,2-a]pyridine-3-carbaldehyde (Intermediate 1, 70 mg, 0.31 mmol) in ethanol (3 mL) was added methyl hydrazine (17 mg, 0.47 mmol) at RT. The reaction was heated at 85° C. for 3 h. Ethanol was evaporated. Pyridine (2 mL) was added to this residue, followed by addition of benzene sulfonylchloride (83 mg, 0.47 mmol). The reaction mixture was stirred at RT overnight. Pyridine was evaporated. Water was added to this residue and extracted with dichloromethane. Organic layer was dried over sodium sulfate and evaporated. The crude product was purified by column chromatography (silica gel, 1.5% methanol in chloroform) to obtain the title compound.

Yield: 68%; $^1$H NMR (DMSO-$d_6$; 300 MHz): δ 9.69 (s, 1H), 8.96 (s, 1H), 8.64-8.65 (d, 1H, J=4.5 Hz), 8.27 (s, 1H), 8.12-8.15 (d, 1H, J=8.1 Hz), 7.99 (s, 1H), 7.86 (s, 2H), 7.78-7.75 (d, 2H, J=8.1 Hz), 7.57-7.62 (t, 2H, J=6.3 Hz), 7.42-7.47 (t, 2H, J=7.8 Hz), 3.22 (s, 3H); MS: m/z 392 (M+1)$^+$.

The compounds of Examples 2-82 were prepared by following the procedure as described for Example 1, using Intermediate 1, methyl hydrazine and an appropriate sulfonylchloride derivative.

Example 2

N,3-dimethyl-N'-((6-pyridin-3-yl) imidazo[1,2-a]pyridine-3-yl)methylene) benzenesulfonohydrazide

Yield: 47%; $^1$H NMR (DMSO-$d_6$; 300 MHz,): δ 9.74 (s, 1H), 9.00-9.01 (d, 1H, J=3 Hz), 8.67-8.69 (dd, 1H, J=1.2, 4.8 Hz,), 8.29 (s, 1H), 8.16-8.20 (m, 1H), 8.02 (s, 1H), 7.86 (s, 2H), 7.57-7.64 (m, 3H), 7.34-7.41 (m, 2H), 3.27 (s, 3H), 2.07 (s, 3H); MS m/z 406 (M+1)$^+$.

Example 3

N,4-dimethyl-N'-((6-(pyridine-3-yl) imidazo[1,2-a]pyridine-3-yl)methylene) benzenesulfonohydrazide

Yield: 55%; $^1$H NMR (DMSO-$d_6$; 300 MHz): δ 9.73 (s, 1H), 8.98-8.99 (d, 1H, J=3 Hz), 8.67-8.69 (dd, 1H, J=3, 6 Hz), 8.24 (s, 1H), 8.15-8.18 (dt, 1H, J=3.6Hz), 8.02 (s, 1H), 7.88 (s, 2H); 7.66-7.68 (d, 2H, J=6 Hz), 7.59-7.63 (m, 1H), 7.25-7.28 (d, 2H, J=9 Hz), 3.22 (s, 3H), 2.27 (s, 3H); MS m/z 407 (M+1)$^+$.

Example 4

2-Fluoro-N-methyl-N'-((6-(pyridine-3-yl) imidazo[1,2-a]pyridine-3-yl) methylene)benzenesulfonohydrazide

Yield: 62.5%; $^1$H NMR (DMSO-$d_6$; 300 MHz): δ 9.56 (s, 1H), 8.91-8.92 (d, 1H, J=1.8 Hz), 8.68-8.67 (dd, 1H, J=1.5, 4.8 Hz), 8.34 (s, 1H), 8.08-8.12 (m, 1H), 8.03 (s, 1H), 7.81-7.86 (m, 3H), 7.60-7.64 (m, 2H), 7.37-7.44 (t, 1H, J=8.7 Hz), 7.11-7.16 (t, 1H, J=7.2 Hz), 3.39 (s, 3H); MS: m/z 410 (M+1)$^+$.

Example 5

3-Fluoro-N-methyl-N'-((6-(pyridine-3-yl) imidazo[1,2-a]pyridine-3-yl)methylene)benzenesulfonohydrazide

Yield: 51%; $^1$H NMR (DMSO-$d_6$; 300 MHz): δ 9.69 (s, 1H), 8.97-8.96 (d, 1H, J=2.1 Hz), 8.66-8.64 (d, 1H, J=4.8 Hz), 8.32 (s, 1H), 8.12-8.15 (d, 1H, J=8.1 Hz), 8.03 (s, 1H), 7.88 (s, 2H), 7.57-7.64 (m, 3H), 7.50-7.54 (m, 2H), 3.28 (s, 3H); MS: m/z 410 (M+1)$^+$.

Example 6

4-Fluoro-N-methyl-N'-((6-(pyridine-3-yl) imidazo[1,2-a]pyridine-3-yl) methylene)benzenesulfonohydrazide

Yield: 55%; $^1$H NMR (DMSO-$d_6$; 300 MHz): δ 9.72 (s, 1H), 8.97-8.78 (d, 1H, J=2.1 Hz), 8.64-8.66 (dd, 1H, J=4.5, 9Hz), 8.31 (s, 1H), 8.13-8.16 (m, 1H), 8.03 (s, 1H), 7.88 (s, 2H), 7.83-7.86 (m, 2H), 7.56-7.61 (m, 1H), 7.30-7.36 (t, 2H, J=9 Hz), 3.22 (s, 3H); MS: m/z 410 (M+1)$^+$.

Example 7

3-Bromo-N-methyl-N'-((6-(pyridine-3-yl) imidazo[1,2-a]pyridine-3-yl)methylene) benzenesulfonohydrazide

Yield: 16%; $^1$H NMR (DMSO-$d_6$; 300 MHz): δ 9.74 (s, 1H), 9.00-9.01 (d, 1H, J=3 Hz), 8.66-8.67 (d, 1H, J=3 Hz), 8.33 (s, 1H), 8.15-8.19 (m, 1H), 8.05 (s, 1H), 7.91-7.92 (m, 2H), 7.88-7.89 (m, 1H), 7.79-7.84 (m, 2H), 7.59-7.63 (dd, 1H, J=3.6Hz), 7.43-7.49 (t, 1H, J=8.1, 7.8 Hz), 3.29 (s, 3H); MS: m/z 470 (M+1)$^+$.

Example 8

4-Bromo-N-methyl-N'-((6-(pyridine-3-yl) imidazo[1,2-a]pyridine-3-yl) methylene)benzenesulfonohydrazide

Yield: 54.4%; $^1$H NMR (DMSO-$d_6$; 300 MHz): δ 9.70 (s, 1H), 8.98-8.99 (d, 1H, J=2.1 Hz), 8.66-8.68 (dd, 1H, J=1.2, 4.8 Hz), 8.32 (s, 1H), 8.13-8.17 (m, 1H), 8.04 (s, 1H), 7.89 (s, 2H), 7.72 (s, 4H), 7.58-7.62 (m, 1H), 3.24 (s, 3H); MS: m/z 470 (M+1)$^+$.

Example 9

2-Cyano-N-methyl-N'-((6-(pyridine-3-yl) imidazo[1,2-a]pyridine-3-yl) methylene)benzenesulfonohydrazide

Yield: 61.5%; $^1$H NMR (DMSO-$d_6$; 300 MHz): δ 9.44 (s, 1H), 8.87-8.88 (d, 1H, J=2.1 Hz), 8.67-8.68 (d, 1H, J=4.8 Hz), 8.40 (s, 1H), 8.10 (s, 1H), 8.05-8.08 (m, 3H), 7.85 (s, 2H), 7.78-7.81 (d, 1H, J=7.5 Hz), 7.65-7.70 (m, 1H), 7.58-7.62 (m, 1H), 3.42 (S, 3H); MS: m/z 417 (M+1)⁺.

Example 10

(E)-3-cyano-N-methyl-N'-((6-(pyridin-3-yl)imidazo[1,2-a]pyridin-3-yl)methylene)benzenesulfonohydrazide Yield: 63%; ¹H NMR (DMSO-$d_6$; 300 MHz): δ 9.67 (s, 1H), 8.96-8.97 (d, 1H, J=3 Hz), 8.46-8.66 (d, 1H, J=6 Hz), 8.33 (s, 1H), 8.23 (s, 1H), 8.13-8.15 (d, 1H J=8.1 Hz), 8.08-8.11 (m, 2H), 8.04-8.05 (m, 1H), 7.85-7.93 (m, 2H), 7.65-7.70 (t, 1H, J=6, 9 Hz), 7.57-7.61 (m, 1H), 3.29 (s, 3H); MS: m/z 417 (M+1)⁺.

Example 11

4-Cyano-N-methyl-N'-((6-(pyridine-3-yl) imidazo[1,2-a]pyridine-3-yl) methylene)benzenesulfonohydrazide Yield: 58%; ¹H NMR (DMSO-$d_6$; 300 MHz): δ 9.68 (s, 1H), 8.96-8.97 (d, 1H, J=2.1 Hz), 8.66-8.68 (d, 1H, J=4.8 Hz), 8.35 (s, 1H), 8.14-8.17 (m, 1H), 8.05 (s, 1H), 7.95-8.01 (m, 4H), 7.90 (s, 2H), 7.58-7.62 (m, 1H), 3.27 (s, 3H); MS: m/z 417 (M+1)⁺.

Example 12

4-Methoxy-N-methyl-N'-((6-(pyridine-3-yl) imidazo[1,2-a]pyridine-3-yl) methylene)benzenesulfonohydrazide Yield: 53%; ¹H NMR (DMSO-$d_6$; 300 MHz): δ 9.80 (s, 1H), 8.95 (s, 1H), 8.69-8.70 (d, 1H, J=3 Hz), 8.09-8.11 (d, 1H, J=6 Hz), 8.00 (s, 1H), 7.91 (s, 1H), 7.82-7.85 (d, 1H, J=9 Hz), 7.67-7.70 (d, 1H, J=9 Hz), 7.44-7.52 (m, 1H), 7.36-7.39 (d, 1H, J=9 Hz), 7.23-7.28 (m, 2H), 7.01-7.04 (d, 1H, J=3 Hz), 3.54 (s, 3H), 3.30 (s, 3H); MS: m/z 422 (M+1)⁺.

Example 13

2,4-Difluoro-N-methyl-N'-((6-(pyridine-3-yl) imidazo[1,2-a]pyridine-3-yl)methylene) benzenesulfonohydrazide Yield: 52%; ¹H NMR (DMSO-$d_6$; 300 MHz): δ 9.61 (s, 1H), 8.92-8.93 (d, 1H, J=2.1 Hz), 8.66-8.68 (dd, 1H, J=1.5, 4.8 Hz), 8.35 (s, 1H), 8.09-8.13 (m, 1H), 8.04 (s, 1H), 7.87-7.94 (m, 3H), 7.58-7.63 (m, 1H), 7.49-7.56 (m, 1H), 7.08-7.11 (m, 1H), 3.25 (s, 3H); MS: m/z 428 (M+1)⁺.

Example 14

2,6-Difluoro-N-methyl-N'-((6-(pyridine-3-yl) imidazo[1,2-a]pyridine-3-yl)methylene) benzenesulfonohydrazide Yield: 49%; ¹H NMR (DMSO-$d_6$; 300 MHz): δ 9.61 (s, 1H), 8.90 (s, 1H), 8.64-8.66 (d, 1H, J=4.5 Hz), 8.38 (s, 1H), 8.08 (s, 1H), 8.05 (s, 1H), 7.87 (s, 2H), 7.67-7.71 (m, 1H), 7.54-7.58 (m, 1H), 7.19-7.25 (t, 2H, J=9.18 Hz), 3.14 (s, 3H); MS: m/z 428 (M+1)⁺.

Example 15

3,4-difluoro-N-methyl-N'-((6-(pyridine-3-yl) imidazo[1,2-a]pyridine-3-yl)methylene) benzenesulfonohydrazide Yield: 42.85%; ¹H NMR (DMSO-$d_6$; 300 MHz): δ 9.72 (s, 1H), 9.00-9.00 (d, 1H, J=2.1 Hz), 8.68-8.70 (dd, 1H, J=1.5, 4.8 Hz), 8.37 (s, 1H), 8.16-8.20 (m, 1H), 8.08 (s, 1H), 7.87-7.93 (m, 3H), 7.68-7.71 (m, 1H), 7.59-7.65 (m, 2H), 3.30 (s, 3H); MS: m/z 428 (M+1)⁺.

Example 16

3,5-Difluoro-N-methyl-N'-((6-(pyridine-3-yl) imidazo[1,2-a]pyridine-3-yl)methylene) benzenesulfonohydrazide Yield: 37%; ¹H NMR (DMSO-$d_6$; 300 MHz): δ 9.66 (s, 1H), 8.97-8.98 (d, 1H, J=2.1 Hz), 8.65-8.67 (d, 1H, J=4.8 Hz), 8.36 (s, 1H), 8.12-8.15 (d, 1H, J=8.1 Hz), 8.06 (s, 1H), 7.90 (s, 2H), 7.57-7.61 (m, 2H), 7.48-7.50 (d, 2H, J=4.5 Hz), 3.25 (s, 3H); MS: m/z 428 (M+1)⁺.

Example 17

3-Chloro-2-fluoro-N-methyl-N'-((6-(pyridine-3-yl) imidazo[1,2-a]pyridine-3-yl)methylene) benzenesulfonohydrazide Yield: 46%; ¹H NMR (DMSO-$d_6$; 300 MHz): δ 9.56 (s, 1H), 8.93-8.94 (d, 1H, J=1.8 Hz), 8.70-8.72 (dd, 1H, J=4.8, 1.5 Hz), 8.40 (s, 1H), 8.10-8.14 (m, 1H), 8.08 (s, 1H), 7.91-7.92 (d, 1H, J=1.5 Hz), 7.89-7.90 (d, 2H, J=1.2 Hz), 7.78-7.82 (m, 1H), 7.62-7.66 (m, 1H), 7.19-7.24 (dt, 1H, J=8.1, 0.6 Hz), 3.44 (s, 3H); MS m/z 444 (M+1)⁺.

Example 18

3-Chloro-4-fluoro-N-methyl-N'-((6-(pyridine-3-yl) imidazo[1,2-a]pyridine-3-yl)methylene) benzenesulfonohydrazide Yield: 57%; ¹H NMR (DMSO-$d_6$; 300 MHz): δ 9.00 (s, 1H), 8.67-8.69 (d, 1H, J=4.5 Hz), 8.35 (s, 1H), 8.18-8.20 (d, 1H, J=8.1 Hz), 8.09 (s, 1H), 7.85-7.98 (m, 3H), 7.80-7.84 (m, 1H), 7.53-7.65 (m, 1H), 7.35-7.38 (d, 2H, J=9.3 Hz), 3.29 (s, 3H); MS: m/z 444 (M+1)⁺.

Example 19

2-Fluoro-N, 5-dimethyl-N'-((6-(pyridine-3-yl) imidazo[1,2-a]pyridine-3-yl)methylene) benzenesulfonohydrazide Yield: 60.06%; ¹H NMR (DMSO-$d_6$; 300 MHz): δ 9.67 (s, 1H), 8.97-8.98 (d, 1H, J=2.1 Hz), 8.67-8.69 (dd, 1H, J=1.2, 4.8 Hz), 8.32 (s, 1H), 8.14-8.17 (m, 1H), 8.02 (s, 1H), 7.87 (s, 2H), 7.60-7.65 (m, 1H), 7.55-7.56 (d, 1H, J=1.5 Hz), 7.39-7.42 (m, 1H), 7.24-7.27 (t, 1H, J=1.8 Hz), 3.39 (s, 3H), 1.90 (s, 3H); MS: m/z 424 (M+1)⁺.

Example 20

3-Fluoro-N, 4-dimethyl-N'-((6-(pyridine-3-yl) imidazo[1,2-a]pyridine-3-yl)methylene) benzenesulfonohydrazide Yield: 48%; $^1$H NMR (DMSO-d$_6$; 300 MHz): δ 9.74 (s, 1H), 9.00-9.01 (d, 1H, J=1.8 Hz), 8.68-8.70 (dd, 1H, J=4.8, 1.2 Hz), 8.34 (s, 1H), 8.16-8.20 (m, 1H), 8.06 (s, 1H), 7.91 (s, 2H), 7.62-7.64 (m, 1H), 7.56-7.60 (m, 2H), 7.45-7.52 (m, 1H), 3.28 (s, 3H), 2.21 (s, 3H); MS m/z 424 (M+1)$^+$.

Example 21

5-Fluoro-N, 2-dimethyl-N'-((6-(pyridine-3-yl) imidazo[1,2-a]pyridine-3-yl)methylene) benzenesulfonohydrazide Yield: 61%; $^1$H NMR (DMSO-d$_6$; 300 MHz): δ 9.53 (s, 1H), 8.89-8.90 (d, 1H, J=2.1 Hz), 8.65-8.67 (dd, 1H, J=1.2, 4.5 Hz), 8.31 (s, 1H), 8.02-8.07 (m, 2H), 7.85 (s, 2H), 7.55-7.60 (m, 2H), 7.34-7.44 (m, 2H), 3.39 (s, 3H), 3.31 (s, 3H); MS: m/z 424 (M+1)$^+$.

Example 21a 3-(3-((2-(5-fluoro-2-methylphenylsulfonyl)-2-methylhydrazono) methyl)imidazo[1,2-a]pyridin-6-yl) pyridine 1-oxide To an ice-cooled solution of 5-fluoro-N, 2-dimethyl-N'-((6-(pyridin-3-yl)imidazo[1,2-a]pyridin-3-yl)methylene) benzenesulfonohydrazide (step 1, 18 mg, 0.043 mmol) in CH$_2$Cl$_2$ was added 3-chloroperoxybenzoic acid (14.46 mg, 0.065 mmol). The reaction mixture was stirred for 3 h at RT. The reaction mixture was then poured on to water. Organic layer was separated, washed with saturated solution of NaHCO$_3$ and dried over Na$_2$SO$_4$. Crude compound was purified by column chromatography (silica gel, 5% EtOAc in petroleum ether) to obtain the title compound. Yield: 64%; $^1$H NMR (DMSO-d$_6$; 300 MHz,): δ 9.45 (s, 1H), 8.57 (s, 1H), 8.32-8.31 (m, 2H), 8.03 (s, 1H), 7.83-7.79 (m, 2H), 7.67-7.64 (dd, 1H, J=8.4 Hz, 2.4 Hz), 7.56 (m, 1H), 7.43-7.36 (m, 3H), 3.40 (s, 3H), 2.54 (s, 3H); MS: m/z 440 (M+1)$^+$.

Example 22

4-Bromo-N, 3-dimethyl-N'-((6-(pyridine-3-yl) imidazo[1,2-a]pyridine-3-yl)methylene) benzenesulfonohydrazide Yield: 39.7%; $^1$H NMR (DMSO-d$_6$; 300 MHz): δ 9.78 (s, 1H), 9.03-9.04 (d, 1H, J=2.1 Hz), 8.71-8.73 (dd, 1H, J=1.2, 4.8 Hz), 8.32 (s, 1H), 8.23-8.26 (m, 1H), 8.15 (s, 1H), 8.02-8.06 (dd, 1H, J=1.5, 9.3 Hz), 7.94-7.97 (d, 1H, J=9.3 Hz), 7.73-7.74 (d, 1H, J=2.1 Hz), 7.68-7.72 (m, 2H), 7.50-7.54 (dd, 1H, J=2.1, 8.4 Hz), 3.29 (s, 3H), 2.17 (s, 3H); MS: m/z 484 (M+1)$^+$.

Example 23

N-methyl-N'-((6-(pyridine-3-yl) imidazo[1,2-a]pyridine-3-yl) methylene)-3,5-bis(trifluoromethyl)benzenesulfonohydrazide Yield: 47%; $^1$H NMR (DMSO-d$_6$; 300 MHz): δ 9.79 (s, 1H), 9.01-9.02 (d, 1H, J=2.1 Hz), 8.64-8.66 (dd, 1H, J=1.2, 4.8 Hz), 8.44 (s, 1H), 8.35 (s, 1H), 8.28 (s, 2H), 8.17-8.21 (m, 1H), 8.05 (S, 1H), 7.89-7.94 (m, 2H), 7.57-7.61 (m, 1H), 3.36 (s, 3H); MS: m/z 528 (M+1)$^+$.

Example 24

3-Cyano-4-fluoro-N-methyl-N'-((6-(pyridine-3-yl) imidazo[1,2-a]pyridine-3-yl)methylene) benzenesulfonohydrazide Yield: 37%; $^1$H NMR (DMSO-d$_6$; 300 MHz): δ 9.71 (s, 1H), 8.99-9.00 (d, 1H, J=1.5 Hz), 8.67-8.69 (dd, 1H, J=9, 4.8 Hz), 8.40-8.42 (dd, 1H, J=8.4, 2.4 Hz), 8.38 (s, 1H), 8.16-8.19 (m, 2H), 8.10 (s, 1H), 7.92-7.93 (m, 2H), 7.66-7.69 (d, 1H, J=9 Hz), 7.60-7.63 (m, 1H), 3.31 (s, 3H); MS: m/z 435 (M+1)$^+$.

Example 25

N, 2-dimethyl-5 nitro-N'-((6-pyridin-3-yl) imidazo[1,2-a]pyridine-3-yl)methylene)benzenesulfonohydrazide Yield: 35%; $^1$H NMR (DMSO-d$_6$; 300 MHz): δ 9.58 (s, 1H), 8.86-8.87 (d, 1H, J=3 Hz), 8.61-8.63 (dd, 1H, J=1.2, 4.8 Hz), 8.53-8.54 (d, 1H, J=3 Hz), 8.35 (s, 1H), 8.28-8.32 (m, 1H), 8.06-8.10 (m, 1H), 8.03 (s, 1H), 7.86 (s, 2H), 7.68-7.71 (d, 1H, J=8.4 Hz), 7.58-7.56 (m, 1H), 3.41 (s, 3H), 2.66 (s, 3H); MS: m/z 451 (M+1).

Example 26

2-Bromo-4,6-difluoro-N-methyl-N'-((6-(pyridine-3-yl) imidazo[1,2-a]pyridine-3-yl)methylene) benzenesulfonohydrazide Yield: 17.85%; $^1$H NMR (DMSO-d$_6$; 300 MHz): δ 9.51 (s, 1H), 8.86 (s, 1H), 8.68 (s, 1H), 8.39 (s, 1H), 8.08 (s, 1H), 8.03-8.05 (d, 1H, J=6.6 Hz), 7.88 (s, 2H), 7.72-7.73 (d, 1H, J=1.2 Hz), 7.59 (S, 1H), 7.47-7.49 (m, 1H), 3.52 (s, 3H); MS: m/z 506 (M+1)$^+$.

Example 27

N, 2,4,6-tetramethyl-N'-((6-(pyridine-3-yl) imidazo[1,2-a]pyridine-3-yl) methylene)benzenesulfonohydrazide Yield: 37%; $^1$H NMR (DMSO-d$_6$; 300 MHz): δ 9.06 (s, 1H), 8.70-7.71 (d, 2H, J=2.7 Hz), 8.25 (s, 1H), 7.98 (s, 1H), 7.93-7.97 (m, 1H), 7.80-7.83 (d, 1H, J=9.3 Hz), 7.65-7.69 (dd, 1H, J=1.8, 9.3 Hz), 7.56-7.60 (m, 1H), 6.87 (s, 2H), 3.36 (s, 3H), 2.43 (s, 6H), 2.16 (s, 3H); MS: m/z 434 (M+1)$^+$.

Example 28

N-methyl-1-phenyl-N'-((6-(pyridine-3-yl) imidazo[1,2-a]pyridine-3-yl) methylene)benzenesulfonohydrazide Yield: 50%; $^1$H NMR (DMSO-d$_6$; 300 MHz): δ 9.60 (s, 1H), 8.97-8.98 (d, 1H, J=2.1 Hz), 8.61-8.63 (dd, 1H, J=1.2, 4.5 Hz), 8.21 (s, 1H), 8.11-8.14 (m, 1H), 8.01 (s, 1H), 7.81-

7.89 (m, 2H), 7.48-7.54 (m, 1H), 7.23-7.26 (m, 2H), 7.07-7.13 (m, 3H), 4.66 (s, 2H), 3.20 (s, 3H); MS: m/z 406 (M+1)$^+$.

Example 29

N-methyl-N'-((6-(pyridine-3-yl) imidazo[1,2-a]pyridine-3-yl)methylene) thiophene-2-sulfonohydrazide Yield: 64%; $^1$H NMR (DMSO-d$_6$; 300 MHz): δ 9.90 (s, 1H), 9.03 (s, 1H), 8.62-8.63 (d, 1H, J=4.2 Hz), 8.35 (s, 1H), 8.18-8.20 (d, 1H, J=7.8 Hz), 8.05 (s, 1H), 7.87-7.96 (m, 3H), 7.69-7.70 (d, 1H, J=3.3 Hz), 7.54-7.59 (m, 1H), 7.15-7.18 (t, 1H, J=3.9, 8.4 Hz), 3.19 (s, 3H); MS: m/z 398 (M+1)$^+$.

Example 30

N-methyl-N'-((6-(pyridine-3-yl) imidazo[1,2-a]pyridine-3-yl)methylene) quinoline-8-sulfonohydrazide Yield: 64%; $^1$H NMR (DMSO-d$_6$; 300 MHz): δ 9.34 (s, 1H), 8.98-8.99 (d, 1H, J=3 Hz), 8.85 (s, 1H), 8.75-8.76 (d, 1H, J=4.8 Hz), 8.41-8.43 (d, 1H, J=7.2 Hz), 8.16-8.19 (d, 3H, J=7.8 Hz), 8.03-8.06 (d, 1H, J=8.1 Hz), 7.90 (s, 1H), 7.77 (s, 2H), 7.60-7.73 (m, 2H), 7.27-7.32 (t, 1H, J=7.8 Hz), 3.68 (s, 3H); MS: m/z 443 (M+1)$^+$.

Example 31

N-methyl-N'-((6-(pyridine-3-yl) imidazo[1,2-a]pyridine-3-yl)methylene) cyclohexanesulfonohydrazide Yield: 20%; $^1$H NMR (DMSO-d$_6$; 300 MHz): δ 9.84 (s, 1H), 8.97-8.98 (d, 1H, J=1.8 Hz), 8.61-8.63 (dd, 1H, J=1.2, 4.5 Hz), 8.26 (s, 1H), 8.14-8.17 (m, 1H), 8.05 (s, 1H), 7.88 (s, 2H), 7.52-7.56 (m, 1H), 3.38 (s, 3H), 1.98-2.02 (d, 2H, J=11.4 Hz), 1.70-1.74 (m, 2H), 1.44-1.53 (m, 3H), 1.20-1.24 (m, 3H); MS: m/z 398 (M+1)$^+$.

Example 32

3-Fluoro-N, 4-dimethyl-N'-((6-(pyridine-3-yl) imidazo[1,2-a]pyridine-3-yl)methylene) benzenesulfonohydrazide Yield: 48%; $^1$H NMR (300 MHz, DMSO-d$_6$): δ 9.74 (s, 1H), 9.00-9.01 (d, 1H, J=1.8 Hz), 8.68-8.70 (dd, 1H, J=4.8, 1.2 Hz), 8.34 (s, 1H), 8.16-8.20 (m, 1H), 8.06 (s, 1H), 7.91 (s, 2H), 7.62-7.64 (m, 1H), 7.56-7.60 (m, 2H), 7.45-7.52 (m, 1H), 3.28 (s, 3H), 2.21 (s, 3H); MS: m/z 424 (M+1)$^+$.

Example 33

3-Cyano-4-fluoro-N-methyl-N'-((6-(pyridine-3-yl) imidazo[1,2-a]pyridine-3-yl)methylene) benzenesulfonohydrazide Yield: 37%; $^1$H NMR (300 MHz, DMSO-d$_6$): δ 9.71 (s, 1H), 8.99-9.00 (d, 1H, J=1.5 Hz), 8.67-8.69 (dd, 1H, J=9, 4.8 Hz), 8.40-8.42 (dd, 1H, J=8.4, 2.4 Hz), 8.38 (s, 1H), 8.16-8.19 (m, 2H), 8.10 (s, 1H), 7.92-7.93 (m, 2H), 7.66-7.69 (d, 1H, J=9 Hz), 7.60-7.63 (m, 1H), 3.31 (s, 3H); MS: m/z 435 (M+1)$^+$.

Example 34

(E)-2,3,4-Trifluoro-N-methyl-N'-((6-(pyridin-3-yl) imidazo[1,2-a]pyridin-3-yl)methylene)benzenesulfonohydrazide Yield: 50%; $^1$H NMR (300 MHz, DMSO-d$_6$): δ 9.64 (s, 1H), 8.94-8.95 (d, 1H, J=1.8 Hz), 8.68-8.69 (dd, 1H, J=1.2, 4.5 Hz), 8.40 (s, 1H), 8.12-8.15 (m, 1H), 8.08 (s, 1H), 7.90 (s, 2H), 7.63-7.74 (m, 1H), 7.59-7.62 (m, 1H), 7.33-7.41 (m, 1H), 3.39 (s, 3H); MS: m/z 446 (M+1)$^+$.

Example 35

(E)-4-bromo-2,5-difluoro-N-methyl-N'-((6-(pyridin-3-yl)imidazo[1,2-a]pyridin-3-yl)methylene)benzenesulfonohydrazide Yield: 16%; $^1$H NMR (300 MHz, DMSO-d$_6$): δ 9.69 (s, 1H), 8.98 (s, 1H), 8.67-8.68 (d, 1H, J=4.5 Hz), 8.39 (s, 1H), 8.08-8.15 (m, 1H), 8.05 (s, 1H), 8.00-8.03 (m, 1H), 7.88 (s, 2H), 7.71-7.75 (t, 1H, J=6, 7.2 Hz), 7.60-7.63 (m, 1H), 3.40 (s, 3H); MS: m/z 506 (M+1)$^+$.

Example 36

(E)-2-bromo-4-fluoro-N-methyl-N'-((6-(pyridin-3-yl)imidazo[1,2-a]pyridin-3-yl)methylene)benzenesulfonohydrazide Yield: 23%; $^1$H NMR (300 MHz, DMSO-d$_6$): δ 9.28 (s, 1H), 8.82-8.83 (d, 1H, J=2.1 Hz), 8.72-8.74 (dd, 1H, J=1.5, 4.8 Hz), 8.35 (s, 1H), 8.08-8.13 (m, 1H), 8.05 (s, 1H), 8.02-8.03 (m, 1H), 7.78-7.88 (m, 3H), 7.63-7.67 (m, 1H), 6.95-6.98 (t, 1H, J=2.7, 6.3 Hz), 3.55 (s, 3H); MS: m/z 488 (M+1)$^+$.

Example 37

(E)-N-methyl-N'-((6-(pyridin-3-yl) imidazo[1,2-a]pyridin-3-yl)methylene)-3-(trifluoromethyl)benzenesulfonohydrazide Yield: 29%; $^1$H NMR (300 MHz, DMSO-d$_6$): δ 9.79 (s, 1H), 9.02 (s, 1H), 8.67-8.68 (d, 1H, J=3 Hz), 8.34 (s, 1H), 8.12-8.21 (m, 2H), 8.00-8.05 (m, 3H), 7.89-7.94 (m, 2H), 7.77-7.82 (t, 1H, J=7.8 Hz), 7.59-7.63 (m, 1H), 3.31 (s, 3H); MS: m/z 460 (M+1)$^+$.

Example 38

(E)-4-bromo-2,6-dichloro-N-methyl-N'-((6-(pyridin-3-yl) imidazo[1,2-a]pyridin-3-yl)methylene)benzenesulfonohydrazide Yield: 8%; $^1$H NMR (300 MHz, DMSO-d$_6$): δ 9.29 (s, 1H), 8.78 (s, 1H), 8.69-8.70 (d, 1H, J=4.5 Hz), 8.35 (s, 1H), 8.06 (s, 1H), 7.97-7.99 (d, 1H, J=8.1 Hz), 7.85-7.88 (m, 3H), 7.77-7.80 (m, 1H), 7.57-7.61 (m, 1H), 3.54 (s, 3H); MS: m/z 537 (M+1)$^+$.

Example 39

(E)-3-chloro-N-methyl-N'-((6-(pyridin-3-yl)imidazo[1,2-a]pyridin-3-yl)methylene)benzenesulfonohydrazide Yield: 48%; $^1$H NMR (300 MHz, DMSO-d$_6$): δ 9.73 (s, 1H), 9.04 (s, 1H), 8.68-8.69 (d, 1H, J=4.8 Hz), 8.35 (s, 1H), 8.01-8.19 (m, 1H), 8.11 (s, 1H), 7.89-7.95 (m, 2H), 7.73-7.83 (m, 3H), 7.63-7.65 (m, 2H), 3.35 (s, 3H); MS: m/z 426 (M+1)+.

Example 40

(E)-2-chloro-N-methyl-N'-((6-(pyridin-3-yl) imidazo[1,2-a]pyridin-3-yl)methylene)-4-(trifluoromethyl) benzenesulfonohydrazide Yield: 32%; $^1$H NMR (300 MHz, DMSO-$d_6$): δ 9.28 (s, 1H), 8.81-8.82 (d, 1H, J=2.1 Hz), 8.72-8.74 (dd, 1H, J=1.2, 4.5 Hz), 8.38 (s, 1H), 8.22-8.25 (d, 1H, J=8.1 Hz), 8.12 (s, 1H), 8.02-8.06 (m, 2H), 7.82-7.88 (m, 2H), 7.62-7.67 (dd, 1H, J=4.8, 7.8 Hz), 7.47-7.50 (d, 1H, J=8.4 Hz), 3.56 (s, 3H); MS: m/z 494 (M+1)+.

Example 41

(E)-2-chloro-4-fluoro-N-methyl-N'-((6-(pyridin-3-yl)imidazo[1,2-a]pyridin-3-yl)methylene) benzenesulfonohydrazide Yield: 36%; $^1$H NMR (300 MHz, DMSO-$d_6$): δ 9.35 (s, 1H), 8.84-8.85 (d, 1H, J=2.1 Hz), 8.71-8.73 (dd, 1H, J=1.5, 4.8 Hz), 8.34 (s, 1H), 8.08-8.11 (m, 1H), 8.04-8.07 (m, 2H), 7.80-7.88 (m, 2H), 7.69-7.73 (dd, 1H, J=2.4, 8.7 Hz), 7.63-7.67 (m, 1H), 6.97-7.04 (m, 1H), 3.52 (s, 3H); MS: m/z 444 (M+1)+.

Example 42

(E)-N,1,2-trimethyl-N'-((6-(pyridin-3-yl) imidazo[1,2-a]pyridin-3-yl)methylene)-1H-imidazole-4-sulfonohydrazide Yield: 44%; $^1$H NMR (300 MHz, DMSO-$d_6$): δ 8.99 (s, 1H), 9.09 (s, 1H), 8.64-8.66 (d, 1H, J=4.5 Hz), 8.29 (s, 2H), 8.01 (s, 1H), 7.85-7.94 (m, 2H), 7.71 (s, 1H), 7.56-7.60 (dd, 1H, J=4.8, 7.8 Hz), 3.47 (s, 3H), 3.29 (s, 3H), 2.10 (s, 3H); MS m/z 410 (M+1)+.

Example 43

(E)-4-chloro-N,2,5-trimethyl-N'-((6-(pyridin-3-yl) imidazo[1,2-a]pyridin-3-yl)methylene) benzenesulfonohydrazide Yield: 35%; $^1$H NMR (300 MHz, DMSO-$d_6$): δ 9.64 (s, 1H), 8.96-8.73 (d, 1H, J=2.1 Hz), 8.68-8.70 (dd, 1H, J=1.5, 4.8 Hz), 8.31 (s, 1H), 8.12-8.16 (m, 1H), 8.04 (s, 1H), 7.87-7.88 (d, 2H, J=1.2 Hz), 7.77 (s, 1H), 7.60-7.64 (m, 1H), 7.48 (s, 1H), 3.39 (s, 3H), 2.52 (s, 3H), 1.95 (s, 3H); MS: m/z 454 (M+1)+.

Example 44

(E)-2,5-difluoro-N-methyl-N'-((6-(pyridin-3-yl) imidazo[1,2-a]pyridin-3-yl)methylene) benzenesulfonohydrazide Yield: 57%; $^1$H NMR (300 MHz, CDCl$_3$): δ 9.65 (s, 1H), 8.93-8.94 (d, 1H, J=1.8 Hz), 8.72-8.74 (dd, 1H, J=1.2, 4.8 Hz), 8.02-8.03 (m, 1H), 7.99-8.00 (m, 1H), 7.95 (s, 1H), 7.82-7.85 (m, 1H), 7.64-7.68 (dd, 1H, J=1.8, 9.3 Hz), 7.58-7.63 (m, 1H), 7.50-7.55 (m, 1H), 7.11-7.19 (m, 2H), 3.51 (s, 3H); MS: m/z 428 (M+1)+.

Example 45

(E)-5-fluoro-2-methoxy-N-methyl-N'-((6-(pyridin-3-yl)imidazo[1,2-a]pyridin-3-yl)methylene)benzenesulfonohydrazide Yield: 51%; $^1$H NMR (300 MHz, CDCl$_3$): δ 9.57 (s, 1H), 8.91 (s, 1H), 8.74-8.75 (d, 1H, J=3.6 Hz), 7.97-8.00 (d, 1H, J=7.5 Hz), 7.92 (s, 2H), 7.81-7.84 (d, 1H, J=9 Hz), 7.54-7.70 (m, 3H), 7.10-7.16 (m, 1H), 6.87-6.91 (m, 1H), 3.86 (s, 3H), 3.56 (s, 3H); MS: m/z 440 (M+1)+.

Example 46

(E)-4-Iodo-N-methyl-N'-((6-(pyridin-3-yl)imidazo[1,2-a]pyridin-3-yl)methylene)benzenesulfonohydrazide Yield: 25%; $^1$H NMR (300 MHz, DMSO-$d_6$): 9.70 (s, 1H), 8.99 (s, 1H), 8.68 (s, 1H), 8.33 (s, 1H), 8.15 (m, 2H), 7.90 (m, 3H), 7.61 (m, 3H), 3.25 (s, 3H); MS: m/z 518 (M+1)+

Example 47

(E)-2'-Fluoro-N-methyl-N'-((6-(pyridin-3-yl)imidazo[1,2-a]pyridin-3-yl)methylene)-5'-(trifluoromethyl)biphenyl-4-sulfonohydrazide Yield: 53%; $^1$H NMR (300 MHz, DMSO-$d_6$): 9.78 (s, 1H), 9.01 (s, 1H), 8.65 (s, 1H), 8.37 (s, 1H), 8.20 (m, 11H), 3.32 (s, 3H); MS: m/z 554 (M+1)+.

Example 48

4-Methyl-3-(1-methyl-2-((6-(pyridin-3-yl) imidazo[1,2-a]pyridin-3-yl)methylene) hydrazinylsulfonyl)benzoic acid Yield: 13%; $^1$H NMR (DMSO-$d_6$; 300 MHz): δ 12.6-13.8 (bs, 1H), 9.64 (s, 1H), 8.90 (s, 1H), 8.61-8.62 (d, 1H, J=7.5 Hz), 8.38 (s, 1H), 8.31 (s, 1H), 8.04-8.07 (d, 1H, J=4.8 Hz), 7.97-8.01 (m, 2H), 7.85 (s, 2H), 7.50-7.55 (m, 2H), 3.34 (s, 3H), 2.61 (s, 3H); MS: m/z 450 (M+1)+.

Example 49

4-Methoxy-3-(1-methyl-2-((6-(pyridin-3-yl)imidazo[1,2-a]pyridin-3-yl)methylene)hydrazinylsulfonyl)benzamide Yield: 14.56%; $^1$H NMR (DMSO-$d_6$; 300 MHz): δ 9.60 (s, 1H), 8.94 (s, 1H), 8.62-8.63 (d, 1H, J=4.2 Hz), 8.44-8.45 (d, 1H, J=1.8 Hz), 8.23 (s, 1H), 8.04-8.07 (dd, 1H, J=5.7 Hz, 1.8 Hz), 7.98 (bs, 3H), 7.80-7.87 (m, 2H), 7.61-7.65 (m, 1H), 7.35 (s, 1H), 7.23-7.26 (d, 1H, J=8.7 Hz), 3.84 (s, 3H), 3.42 (s, 3H); MS: m/z 434(M+1)+.

Example 50

(E)-N,2,5-trimethyl-N'-((6-(pyridin-3-yl) imidazo[1,2-a]pyridin-3-yl) methylene)benzenesulfonohydrazide Yield: 40%; $^1$H NMR (300 MHz, DMSO-$d_6$): δ 9.75 (s, 1H), 8.94 (s, 1H), 8.72-8.73 (d, 1H, J=3.9 Hz), 8.05-8.09 (m, 1H), 7.91-7.96 (m, 2H), 7.82-7.86 (d, 1H, J=9.3 Hz), 7.73 (s, 1H), 764-7.67 (dd, 1H, J=1.8 & 9.3 Hz), 7.52-7.55 (m, 1H), 7.13-7.15 (m, 2H), 3.46 (s, 3H), 2.52 (s, 3H), 1.95 (s, 3H); MS: m/z 420 (M+1)+.

Example 51

(E)-2,5-dibromo-N-methyl-N'-((6-(pyridin-3-yl) imidazo[1,2-a]pyridin-3-yl)methylene) benzenesulfonohydrazide Yield: 25%; $^1$H NMR (300 MHz, DMSO-d$_6$): δ 9.60 (s, 1H), 8.95 (s, 1H), 8.73-8.74 (d, 1H, J=3.9 Hz), 8.20-8.21 (d, 1H, J=2.4 Hz), 8.05-8.08 (m, 1H), 7.97 (s, 1H), 7.93 (s, 1H), 7.81-7.84 (d, 1H, J=9.3 Hz), 7.64-7.68 (dd, 1H, J=1.8 & 9.3 Hz), 7.55-7.70 (m, 1H), 7.51-7.54 (d, 1H, J=8.4 Hz), 7.36-7.40 (dd, 1H, J=2.4 & 8.4 Hz), 3.65 (s, 3H); MS: m/z 549.9 (M+1)+.

Example 52

(E)-2,5-dimethoxy-N-methyl-N'-((6-(pyridin-3-yl) imidazo[1,2-a]pyridin-3-yl)methylene) benzenesulfonohydrazide Yield: 40%; $^1$H NMR (300 MHz, DMSO-d$_6$): δ 9.73 (s, 1H), 8.93-8.94 (d, 1H, J=1.8 Hz), 8.69-8.71 (dd, 1H, J=1.5 & 4.8 Hz), 8.04-8.08 (m, 1H), 7.88-7.92 (m, 2H), 7.77-7.80 (d, 1H, J=9.6 Hz), 7.60-7.64 (dd, 1H, J=1.8 & 9.3 Hz), 7.53-7.57 (m, 1H), 7.43-7.44 (d, 1H, J=3 Hz), 6.93-6.97 (dd, 1H, J=3 & 9 Hz), 6.85-6.88 (d, 1H, J=9 Hz), 3.83 (s, 3H), 3.55 (s, 3H), 3.37 (s, 3H); MS: m/z 452.1 (M+1)+.

Example 53

(E)-N, 2-dimethyl-N'-((6-(pyridin-3-yl) imidazo[1,2-a]pyridin-3-yl) methylene)benzenesulfonohydrazide Yield: 42%; $^1$H NMR (300 MHz, DMSO-d$_6$): δ 9.46 (s, 1H), 8.84-8.85 (d, 1H, J=1.8 Hz), 8.74-8.76 (dd, 1H, J=1.5 & 4.8 Hz), 7.90-8.00 (m, 4H), 7.77-7.80 (m, 1H), 7.50-7.59 (m, 2H), 7.31-7.37 (m, 1H), 7.22-7.26 (m, 1H), 6.87-6.92 (m, 1H), 3.49 (s, 3H), 1.65 (s, 3H); MS: m/z 406 (M+1)+.

Example 54

(E)-N-methyl-N'-((6-(pyridin-3-yl) imidazo[1,2-a]pyridin-3-yl)methylene)-2-(trifluoromethoxy)benzenesulfonohydrazide Yield: 42%; $^1$H NMR (300 MHz, DMSO-d$_6$): δ 9.38 (s, 1H), 8.84-8.85 (d, 1H, J=1.8 Hz), 8.76-8.78 (m, 1H), 8.06-8.09 (dd, 1H, J=1.5 & 8.1 Hz), 7.97-8.00 (m, 1H), 7.95 (s, 1H), 7.92 (s, 1H), 7.78-7.81 (d, 1H, J=9.3 Hz), 7.47-7.58 (m, 3H), 7.32-7.35 (m, 1H), 6.98-7.03 (m, 1H), 3.57 (s, 3H); MS: m/z 476 (M+1)+.

Example 55

(E)-5-chloro-2-methoxy-N-methyl-N'-((6-(pyridin-3-yl) imidazo[1,2-a]pyridin-3-yl)methylene) benzenesulfonohydrazide Yield: 19.90%; $^1$H NMR (300 MHz, DMSO-d$_6$): δ 9.65 (s, 1H), 8.95-8.96 (d, 1H, J=2.1 Hz), 8.72-8.74 (m, 1H), 8.04-8.08 (m, 1H, J=9.3 Hz), 7.89-7.91 (m, 3H), 7.87-7.88 (m, 1H), 7.78-7.81 (d, 1H, J=9.3 Hz), 7.63-7.66 (dd, 1H, J=1.8 & 9.3 Hz), 7.56-7.60 (m, 1H), 7.34-7.37 (dd, 1H, J=2.7 & 9 Hz), 3.87 (s, 3H), 3.55 (s, 3H); MS: m/z 456 (M+1)+.

Example 56

(E)-4-bromo-N-methyl-N'-((6-(pyridin-3-yl) imidazo[1,2-a]pyridin-3-yl)methylene)-2-(trifluoromethoxy) benzenesulfonohydrazide Yield: 36%; $^1$H NMR (300 MHz, DMSO-d$_6$): δ 9.39 (s, 1H), 8.87-8.88 (d, 1H, J=2.1 Hz), 8.78-8.80 (dd, 1H, J=1.2 & 4.5 Hz), 7.92-7.99 (m, 4H), 7.80-7.83 (d, 1H, J=9 Hz), 7.53-7.61 (m, 2H), 7.47 (s, 1H), 7.14-7.17 (dd, 1H, J=1.5 & 8.4 Hz), 3.56 (s, 3H); MS: m/z 554 (M+1)+.

Example 57

(E)-2-bromo-N-methyl-N'-((6-(pyridin-3-yl) imidazo[1,2-a]pyridin-3-yl)methylene)-5-(trifluoromethyl) benzenesulfonohydrazide Yield: 25%; $^1$H NMR (300 MHz, DMSO-d$_6$): δ 9.62 (s, 1H), 8.92-8.93 (d, 1H, J=2.1 Hz), 8.72-8.74 (dd, 1H, J=1.5 & 4.8 Hz), 8.32-8.33 (d, 1H, J=1.8 Hz), 8.02-8.06 (m, 1H), 8.00 (s, 1H), 7.93 (s, 1H), 7.80-7.85 (m, 2H), 7.64-7.68 (dd, 1H, J=1.8 & 9.3 Hz), 7.50-7.55 (m, 2H), 3.66 (s, 3H); MS: m/z 538 (M+1)+.

Example 58

(E)-N-methyl-2-nitro-N'-((6-(pyridin-3-yl) imidazo[1,2-a]pyridin-3-yl) methylene)benzenesulfonohydrazide Yield: 50%; $^1$H NMR (300 MHz, DMSO-d$_6$): δ 9.52 (s, 1H), 8.88-8.89 (d, 1H, J=2.1 Hz), 8.77-8.79 (dd, 1H, J=1.5 & 4.8 Hz), 8.12-8.15 (m, 1H), 8.02-8.06 (m, 1H), 8.01 (s, 1H), 7.97 (s, 1H), 7.83-7.86 (d, 1H, J=9.3 Hz), 7.63-7.68 (m, 2H), 7.60-7.61 (d, 1H, J=1.8 Hz), 7.54-7.58 (dd, 1H, J=5.1 & 8.1 Hz), 7.30-7.33 (m, 1H), 3.55 (s, 3H); MS: m/z 437 (M+1)+.

Example 59

(E)-N-methyl-2-(methylsulfonyl)-N'-((6-(pyridin-3-yl) imidazo[1,2-a]pyridin-3-yl)methylene) benzenesulfonohydrazide Yield: 43%; $^1$H NMR (300 MHz, DMSO-d$_6$): δ 9.42 (s, 1H), 8.91-8.92 (d, 1H, J=1.8 Hz), 8.80-8.81 (m, 1H), 8.29-8.33 (m, 2H), 8.02-8.05 (m, 1H), 7.92 (s, 2H), 7.80-7.83 (d, 1H, J=9 Hz), 7.55-7.67 (m, 3H), 7.13-7.16 (m, 1H), 3.58 (s, 3H), 3.42 (s, 3H); MS: m/z 470 (M+1)+.

Example 60

(E)-N-methyl-2-phenoxy-N'-((6-(pyridin-3-yl) imidazo[1,2-a]pyridin-3-yl)methylene)benzenesulfonohydrazide Yield: 46.94%; $^1$H NMR (300 MHz, DMSO-d$_6$): δ 9.56 (s, 1H), 8.86 (s, 1H), 8.85 (s, 1H), 7.58-7.89 (m, 2H), 7.89 (s, 2H), 7.76-7.79 (d, 1H, J=9.3 Hz), 7.55-7.59 (m, 2H), 7.24-

7.28 (m, 3H), 7.12 (s, 1H), 6.87-6.89 (d, 2H, J=7.8 Hz), 6.76-6.83 (m, 2H), 3.50 (s, 3H); MS: m/z 484 (M+1)$^+$.

Example 61

(E)-N-methyl-N'-((6-(pyridin-3-yl) imidazo[1,2-a]pyridin-3-yl)methylene) hexane-1-sulfonohydrazide Yield: 51%; $^1$H NMR (300 MHz, DMSO-d$_6$): δ 9.89 (s, 1H), 8.96-8.97 (d, 1H, J=2.4 Hz), 8.67-8.69 (dd, 1H, J=1.2&4.5 Hz), 8.03-8.07 (m, 2H), 7.97 (s, 1H), 7.85-7.88 (d, 1H, J=9.3 Hz), 7.69-7.73 (dd, 1H, J=1.8&9.3 Hz), 7.44-7.49 (dd, 1H, J=4.8&8.1 Hz), 3.44 (s, 3H), 3.19-3.24 (m, 2H), 1.77-1.87 (m, 2H), 1.32-1.39 (m, 2H), 1.18-1.27 (m, 4H), 0.80-0.84 (m, 2H); MS: m/z 400 (M+1)$^+$.

Example 62

(E)-N-methyl-2-morpholino-N'-((6-(pyridin-3-yl) imidazo[1,2-a]pyridin-3-yl)methylene)-5-(trifluoromethyl)benzenesulfonohydrazide Yield: 33%; $^1$H NMR (300 MHz, DMSO-d$_6$): δ 9.69 (s, 1H), 9.01-9.02 (d, 1H, J=2.1 Hz), 8.65-8.68 (dd, 1H, J=3.3&4.8 Hz), 8.11-8.22 (m, 2H), 7.92-8.02 (m, 2H), 7.85-7.91 (m, 3H), 7.57-7.67 (m, 2H), 3.79 (s, 4H), 3.56 (s, 3H), 3.02 (s, 4H); MS: m/z 545 (M+1)$^+$.

Example 63

(E)-N,2-dimethyl-5-(methylsulfonyl)-N'-((6-(pyridin-3-yl) imidazo[1,2-a]pyridin-3-yl)methylene) benzenesulfonohydrazide Yield: 52.58%; $^1$H NMR (300 MHz, DMSO-d$_6$): δ 9.74 (s, 1H), 8.98-8.99 (d, 1H, J=2.1 Hz), 8.66-8.67 (m, 1H), 8.31-8.36 (m, 2H), 8.15-8.17 (dd, 1H, J=1.5 &5.7 Hz), 8.07 (s, 2H), 7.88-7.97 (m, 2H), 7.69-7.72 (d, 1H, J=8.1 Hz), 7.58-7.63 (dd, 1H, J=4.8 &7.8 Hz), 3.13 (s, 3H), 2.67 (s, 3H), 2.50 (s, 3H); MS: m/z 484 (M+1)$^+$.

Example 64

(E)-2-bromo-N-methyl-N'-((6-(pyridin-3-yl) imidazo[1,2-a]pyridin-3-yl)methylene) benzenesulfonohydrazide Yield: 47%; $^1$H NMR (300 MHz, DMSO-d$_6$): δ 9.31 (s, 1H), 8.76-8.86 (m, 2H), 8.16-8.19 (dd, 1H, J=1.5 &7.8 Hz), 7.91-7.97 (m, 3H), 7.78-7.81 (d, 1H, J=9.3 Hz), 7.61-7.65 (dd, 1H, J=7.5& 8.1 Hz), 7.52-7.56 (m, 2H), 7.30 (s, 1H), 6.93-6.98 (m, 1H), 3.64 (s, 3H); MS: m/z 471 (M+1)$^+$.

Example 65

(E)-2-chloro-N-methyl-N'-((6-(pyridin-3-yl) imidazo [1,2-a]pyridin-3-yl)methylene)-5-(trifluoromethyl) benzenesulfonohydrazide Yield: 39%; $^1$H NMR (300 MHz, DMSO-d$_6$): δ 9.62 (s, 1H), 8.96 (s, 1H), 8.67 (s, 1H), 8.36 (s, 1H), 8.14 (m, 2H), 8.03 (s, 1H), 7.88-7.95 (m, 4H), 7.59 (s, 1H), 3.56 (s, 3H); MS: m/z 494 (M+1)$^+$.

Example 66

(E)-N-methyl-6-morpholino-N'-((6-(pyridin-3-yl) imidazo[1,2-a]pyridin-3-yl)methylene) pyridine-3-sulfonohydrazide Yield: 45%; $^1$H NMR (300 MHz, DMSO-d$_6$): δ 9.86 (s, 1H), 8.96 (s, 1H), 8.70 (s, 1H), 8.57 (s, 1H), 8.07-8.10 (m, 2H), 7.94 (s, 1H), 7.68-7.87 (m, 3H), 7.51 (s, 1H), 6.46-6.49 (d, 1H, J=8.4 Hz), 3.75 (s, 4H), 3.59 (s, 4H), 3.28 (s, 3H); MS: m/z 478 (M+1)$^+$.

Example 67

(E)-Methyl 1-methyl-5-(1-methyl-2-((6-(pyridin-3-yl) imidazo[1,2-a]pyridin-3-yl)methylene) hydrazinylsulfonyl)-1H-pyrrole-2-carboxylate Yield: 39%; $^1$H NMR (300 MHz, DMSO-d$_6$): δ 9.91 (s, 1H), 8.96 (s, 1H), 8.68-8.69 (d, 1H, J=3 Hz), 8.09-8.10 (d, 1H, J=4.5 Hz), 8.06 (s, 1H), 7.93 (s, 1H), 7.83-7.85 (d, 1H, J=5.7 Hz), 7.68-7.70 (d, 1H, J=5.7 Hz), 7.48-7.50 (dd, 1H, J=2.7&4.2 Hz), 7.15 (s, 1H), 7.05 (s, 1H), 3.76 (s, 3H), 3.71 (s, 3H), 3.28 (s, 3H); MS: m/z 453 (M+1)$^+$.

Example 68

(E)-N,4-dimethyl-N'-((6-(pyridin-3-yl) imidazo[1,2-a]pyridin-3-yl) methylene)-3,4-dihydro-2H-pyrido[3,2-b][1,4]oxazine-7-sulfonohydrazide Yield: 44%; $^1$H NMR (300 MHz, DMSO-d$_6$): δ 9.84 (s, 1H), 9.03 (s, 1H), 8.67 (d, 1H), 8.30 (d, 1H), 8.19-8.21 (d, 1H, J=6.9 Hz), 8.05 (s, 2H), 7.92 (s, 2H), 7.61 (s, 1H), 7.08 (s, 1H), 4.10 (s, 2H), 3.47 (s, 3H), 3.22 (s, 3H), 3.02 (s, 2H); MS: m/z 464 (M+1)$^+$.

Example 69

(E)-N-methyl-N'-((6-(pyridin-3-yl) imidazo[1,2-a]pyridin-3-yl)methylene) pyridine-3-sulfonohydrazide Yield: 44%; $^1$H NMR (300 MHz, DMSO-d$_6$): δ 9.78 (s, 1H), 9.05 (s, 1H), 8.96 (s, 1H), 8.73-8.77 (m, 2H), 8.06-8.10 (m, 3H), 7.97 (s, 1H), 7.69-7.88 (m, 2H), 7.36-7.52 (m, 2H), 3.34 (s, 3H); MS: m/z 393 (M+1)$^+$.

Example 70

(E)-N-methyl-4-phenoxy-N'-((6-(pyridin-3-yl) imidazo[1,2-a]pyridin-3-yl) methylene)benzenesulfonohydrazide Yield: 40%; $^1$H NMR (300 MHz, DMSO-d$_6$): δ 9.87 (s, 1H), 8.96 (s, 1H), 8.67 (s, 1H), 8.03-8.08 (m, 2H), 7.93 (s, 1H), 7.83-7.86 (d, 1H, J=9 Hz), 7.67-7.67-7.76 (m, 3H), 7.36-7.45 (m, 3H), 7.28 (m, 1H), 6.99-7.01 (d, 2H, J=7.2 Hz), 6.85-6.88 (d, 2H, J=8.1 Hz), 3.31 (s, 3H); MS: m/z 484 (M+1)$^+$.

Example 71

(E)-Methyl 3-(1-methyl-2-((6-(pyridin-3-yl)imidazo [1,2-a]pyridin-3-yl)methylene) hydrazinylsulfonyl) thiophene-2-carboxylate Yield: 48%; $^1$H NMR (300 MHz, DMSO-d$_6$): δ 9.53 (s, 1H), 8.89 (s, 1H), 8.68 (s, 1H), 8.34 (s, 1H), 8.06 (s, 2H), 7.87

(s, 2H), 7.75-7.77 (d, 1H, J=4.5 Hz), 7.61 (s, 1H), 7.40-7.42 (d, 1H, J=4.5 Hz), 3.80 (s, 3H), 3.49 (s, 3H); MS: m/z 456 (M+1)$^+$.

Example 72

(E)-N-methyl-N'-((6-(pyridin-3-yl) imidazo[1,2-a]pyridin-3-yl) methylene)biphenyl-4-sulfonohydrazide Yield: 46%; $^1$H NMR (300 MHz, DMSO-d$_6$): δ 9.77 (s, 1H), 9.01-9.02 (d, 1H, J=2.1 Hz), 8.65-8.67 (dd, 1H, J=1.5 &4.8 Hz), 8.33 (s, 1H), 8.17 (s, 1H), 8.04 (s, 2H), 7.89 (s, 2H), 7.86 (s, 1H), 7.76-7.78 (d, 1H, J=8.4 Hz), 7.72 (s, 1H), 7.59-7.64 (m, 3H), 7.41-7.45 (m, 3H), 3.29 (s, 3H); MS: m/z 468 (M+1)$^+$.

Example 73

(E)-Methyl 5-(1-methyl-2-((6-(pyridin-3-yl) imidazo[1,2-a]pyridin-3-yl)methylene) hydrazinylsulfonyl)furan-2-carboxylate Yield: 32%; $^1$H NMR (300 MHz, DMSO-d$_6$): δ 9.82 (s, 1H), 8.96 (s, 1H), 8.68-8.69 (d, 1H, J=3.9 Hz), 8.08-8.11 (m, 2H), 7.95 (s, 1H), 7.82-7.85 (d, 1H, J=9.3 Hz), 7.68-7.72 (dd, 1H, J=1.8 &9.3 Hz), 7.45-7.49 (dd, 1H, J=5.1& 7.8 Hz), 7.07-7.12 (m, 2H), 3.72 (s, 3H), 3.48 (s, 3H); MS m/z 440 (M+1)$^+$.

Example 74

(E)-4-chloro-N-methyl-3-nitro-N'-((6-(pyridin-3-yl) imidazo[1,2-a]pyridin-3-yl)methylene) benzenesulfonohydrazide Yield: 34%; $^1$H NMR (300 MHz, DMSO-d$_6$): δ 9.72 (s, 1H), 8.98-8.99 (d, 1H, J=2.1 Hz), 8.64-8.66 (dd, 1H, J=1.5 &4.8 Hz), 8.42-8.43 (d, 1H, J=2.1 Hz), 8.37 (s, 1H), 8.14-8.17 (m, 1H), 8.03-8.07 (m, 2H), 7.90-7.94 (m, 3H), 7.55-7.60 (dd, 1H, J=4.8 &7.8 Hz), 3.29 (s, 3H); MS: m/z 471 (M+1)$^+$.

Example 75

(E)-5-bromo-2-methoxy-N-methyl-N'-((6-(pyridin-3-yl) imidazo[1,2-a]pyridin-3-yl)methylene) benzenesulfonohydrazide Yield: 47.5%; $^1$H NMR (300 MHz, DMSO-d$_6$): δ 9.68 (s, 1H), 8.95 (s, 1H), 8.72-8.95 (m, 1H), 8.06-8.10 (m, 1H), 7.97-7.98 (d, 1H, J=2.4 Hz), 7.88-7.89 (d, 2H, J=3.9 Hz), 7.78-7.81 (d, 1H, J=9.6 Hz), 7.63-7.67 (dd, 1H, J=1.8, 9.3 Hz), 7.56-7.60 (m, 1H), 7.46-7.49 (dd, 1H, J=2.4, 8.7 Hz), 6.79-6.82 (d, 1H, J=8.7 Hz), 3.85 (s, 3H), 3.53 (s, 3H); MS: m/z 500 (M+1)$^+$.

Example 76

(E)-3-chloro-N, 2-dimethyl-N'-((6-(pyridin-3-yl) imidazo[1,2-a]pyridin-3-yl)methylene) benzenesulfonohydrazide Yield: 45%; $^1$H NMR (300 MHz, DMSO-d$_6$): δ 9.38 (s, 1H), 8.84 (s, 1H), 8.5 (s, 1H), 7.91-7.95 (m, 4H), 7.78-7.81 (d, 1H, J=9.3 Hz), 7.42-7.58 (m, 3H), 6.77-6.82 (m, 3H), 3.49 (s, 3H), 2.59 (s, 3H); MS: m/z 439 (M+1)$^+$.

Example 77

(E)-5-chloro-2-fluoro-N-methyl-N'-((6-(pyridin-3-yl) imidazo[1,2-a]pyridin-3-yl)methylene) benzenesulfonohydrazide Yield: 38%; $^1$H NMR (300 MHz, DMSO-d$_6$): δ 9.68 (s, 1H), 8.95 (s, 1H), 8.72-8.95 (m, 1H), 8.06-8.10 (m, 1H), 7.97-7.98 (d, 1H, J=2.4 Hz), 7.88-7.89 (d, 2H, J=3.9 Hz), 7.78-7.81 (d, 1H, J=9.6 Hz), 7.63-7.67 (dd, 1H, J=1.8, 9.3 Hz), 7.56-7.60 (m, 1H), 7.46-7.49 (dd, 1H, J=2.4, 8.7 Hz), 6.79-6.82 (d, 1H, J=8.7 Hz), 3.53 (s, 3H); MS m/z 443 (M+1)$^+$.

Example 78

(E)-4-Fluoro-N, 2-dimethyl-N'-((6-(pyridin-3-yl) imidazo[1,2-a]pyridin-3-yl)methylene) benzenesulfonohydrazide Yield: 48%; $^1$H NMR (300 MHz, DMSO-d$_6$): δ 9.45 (s, 1H), 8.88 (s, 1H), 8.77 (s, 1H), 7.80-8.05 (m, 4H), 7.81-7.84 (d, 1H, J=9.3 Hz), 7.51-7.61 (m, 2H), 6.92-6.96 (dd, 1H, J=2.4& 9 Hz), 6.55-6.61 (m, 1H), 3.52 (s, 3H), 2.55 (s, 3H); MS: m/z 423 (M+1)$^+$.

Example 79

(E)-2-methoxy-N, 6-dimethyl-N'-((6-(pyridin-3-yl) imidazo[1,2-a]pyridin-3-yl)methylene)benzenesulfonohydrazide Yield: 51%; $^1$H NMR (300 MHz, DMSO-d$_6$): δ 9.72 (s, 1H), 8.96-8.97 (d, 1H, J=1.8 Hz), 8.72-8.74 (dd, 1H, J=1.2&4.5 Hz), 8.10-8.14 (m, 1H), 7.78-7.88 (m, 3H), 7.64-7.70 (dd, 2H, J=2.1&16.8 Hz), 7.55-7.61 (m, 1H), 7.16-7.19 (dd, 1H, J=1.8&8.4 Hz), 6.79-6.82 (d, 1H, J=8.4 Hz), 3.84 (s, 3H), 3.55 (s, 3H), 1.81 (s, 3H); MS: m/z 435 (M+1)$^+$.

Example 80

(E)-4-Bromo-2-chloro-N-methyl-N'-((6-(pyridin-3-yl) imidazo[1,2-a]pyridin-3-yl)methylene) benzenesulfonohydrazide Yield: 31%; $^1$H NMR (300 MHz, DMSO-d$_6$): δ 9.38 (s, 1H), 8.79-8.87 (m, 2H), 7.86-8.02 (m, 5H), 7.54-7.63 (m, 3H), 7.07-7.11 (dd, 1H, J=1.8 & 8.4 Hz), 3.61 (s, 3H); MS: m/z 506 (M+1)$^+$.

Example 81

(E)-2-chloro-N-methyl-N'-((6-(pyridin-3-yl) imidazo[1,2-a]pyridin-3-yl)methylene) benzenesulfonohydrazide Yield: 46%; $^1$H NMR (300 MHz, DMSO-d$_6$): δ 9.39 (s, 1H), 8.34 (s, 1H), 8.78-8.79 (d, 1H, J=3.9 Hz), 8.14-8.17 (dd, 1H, J=1.2&7.8 Hz), 7.97-8.01 (m, 1H), 7.94 (s, 2H), 7.83-7.86 (d, 1H, J=9.3 Hz), 7.54-7.61 (m, 2H), 7.43-7.46 (dd, 1H, J=1.2&8.1 Hz), 7.35-7.40 (m, 1H), 6.99 (s, 1H), 3.63 (s, 3H); MS: m/z 426 (M+1)$^+$.

Example 82

(E)-N-(4-(1-methyl-2-((6-(pyridin-3-yl) imidazo[1,2-a]pyridin-3-yl) methylene)hydrazinylsulfonyl)phenyl)acetamide Yield: 48%; $^1$H NMR (300 MHz, DMSO-d$_6$): δ 10.31 (s, 1H), 9.75 (s, 1H), 9.00-9.01 (d, 1H, J=2.1 Hz), 8.67-8.69 (dd, 1H, J=1.5&4.8 Hz), 8.28 (s, 1H), 8.15 (s, 1H), 8.03 (s, 1H), 7.88-7.90 (m, 2H), 7.74 (s, 1H), 7.71 (s, 1H), 7.60-7.65 (m, 3H), 3.24 (s, 3H), 2.02 (s, 3H); MS: m/z 447 (M+1)$^+$.

Example 83

N'-((6-(6-fluoropyridine-3-yl) imidazo[1,2-a]pyridine-3-yl)methylene)-n, 2-dimethyl-5-nitrobenzenesulfonohydrazide The title compound was prepared by following the procedure as described for example 1, using Intermediate 2, methyl hydrazine and 2-methyl-5-nitrobenzene-1-sulfonyl chloride.

Yield: 25%; $^1$H NMR (DMSO-d$_6$; 300 MHz): δ 9.47 (s, 1H), 8.51-8.54 (d, 2H, J=9 Hz), 8.25-8.34 (m, 3H), 7.99-8.03 (d, 1H, J=9 Hz), 7.68-7.88 (m, 3H), 7.36-7.40 (dd, 1H, J=2.1, 8.4 Hz), 3.43 (s, 3H), 2.65 (s, 3H); MS: m/z 469 (M+1)$^+$.

Example 84

(E)-N-ethyl-2-methyl-5-nitro-N'-((6-(pyridin-3-ypimidazo[1,2-a]pyridin-3-yl)methylene)benzenesulfonohydrazide To a solution of 6-(pyridin-3-yl)imidazo[1,2-a]pyridine-3-carbaldehyde (Intermediate 1, 100 mg, 0.444 mmol) in ethanol (10 mL) was added ethyl hydrazine oxalate (120 mg, 0.7998 mmol) at RT. The reaction was heated at 80° C. for 4 h. EtOH was evaporated. Pyridine (5 mL) was added to this residue, followed by addition of 2-methyl-5-nitro benzene sulfonylchloride (126 mg, 0.533 mmol). The reaction mixture was stirred at RT overnight. Pyridine was evaporated. Water was added to this residue and extracted with dichloromethane. Organic layer was dried over sodium sulphate and evaporated. The crude product was purified by column chromatography (silica gel, 1.5% methanol in chloroform) to obtain the title compound. Yield: 15 mg (7%); $^1$HNMR (CDCl$_3$; 300 MHz): δ 9.57 (s, 1H), 8.75 (s, 1H), 8.69 (m, 2H), 8.31 (s, 1H), 8.18 (dd, 1H, J=8.4, 2.1 Hz), 7.99 (s, 1H), 7.91 (d, 1H, J=8.1 Hz), 7.82 (d, 1H, J=9.3 Hz), 7.63 (dd, 1H, J=9, 1.5 Hz), 7.46 (t, 2H, J=8.1 Hz), 3.90 (q, 2H, J=7.2 Hz), 2.70 (s, 3H), 1.32 (t, 3H, J=6.9 Hz); MS: m/z 463 (M−1)$^+$.

The compounds of Examples 85 and 86 were prepared by following the procedure as described for Example 1, using 6-(pyridin-4-yl)imidazo[1,2-a]pyridine-3-carbaldehyde, methyl hydrazine and an appropriate sulfonylchloride derivative.

Example 85

N, 2-dimethyl-5-nitro-N'-((6-(pyridine-4-yl) imidazo[1,2-a]pyridin-3-yl)methylene) benzenesulfonohydrazide Yield: 21%; $^1$H NMR (DMSO-d$_6$; 300 MHz): δ 0.78 (s, 1H), 8.69-8.71 (d, 2H, J=5.7 Hz), 8.56-8.57 (d, 1H, J=2.1 Hz), 8.35 (s, 1H), 8.29-8.33 (dd, 1H, J=2.4, 8.7 Hz), 8.04 (s, 1H), 7.85-7.95 (m, 2H), 7.72-7.74 (d, 2H, J=6 Hz), 7.69 (s, 1H), 3.42 (s, 3H), 2.67 (s, 3H); MS: m/z 451 (M+1)$^+$.

Example 86

5-Fluoro-N, 2-dimethyl-N'-((6-(pyridine-4-yl) imidazo[1,2-a]pyridine-3-yl)methylene) benzenesulfonohydrazide Yield: 27%; $^1$H NMR (DMSO-d$_6$; 300 MHz): δ 9.67 (s, 1H), 8.70-8.72 (d, 2H, J=6 Hz), 8.32 (s, 1H), 8.04 (s, 1H), 7.85 (s, 2H), 7.65-7.68 (m, 2H), 7.62-7.63 (d, 1H, J=2.7 Hz), 7.37-7.46 (m, 2H), 3.43 (s, 3H), 2.48 (s, 3H); MS: m/z 424 (M+1)$^+$.

The compounds of Example 87-98 were prepared by following the procedure as described for Example 1, using Intermediate 3, methyl hydrazine and an appropriate sulfonylchloride derivative.

Example 87

(E)-5-Fluoro-N'-((6-(2-fluoropyridin-3-yl)imidazo[1,2-a]pyridin-3-yl)methylene)-N,2-dimethylbenzenesulfonohydrazide Yield: 48%; $^1$H NMR (DMSO-d$_6$; 300 MHz): δ 9.40 (s, 1H), 8.34-8.36 (d, 1H, J=4.8 Hz), 8.29 (s, 1H), 8.08-8.15 (m, 1H), 8.04 (s, 1H), 7.83-7.87 (d, 1H, J=9.6 Hz), 7.66-7.69 (d, 1H, J=9.3 Hz), 7.52-7.59 (m, 2H), 7.37-7.42 (m, 1H), 7.30-7.34 (m, 1H), 3.42 (s, 3H), 2.43 (s, 3H); MS: m/z 442 (M+1)$^+$.

Example 88

(E)-5-Fluoro-N'-((6-(2-fluoropyridin-3-yl)imidazo[1,2-a]pyridin-3-yl)methylene)-2-methoxy-N-methyl-benzenesulfonohydrazide Yield: 54%; $^1$H NMR (300 MHz, DMSO-d$_6$): δ 9.32 (s, 1H), 8.38 (s, 1H), 8.26 (s, 1H), 8.09-8.12 (m, 1H), 8.04 (s, 1H), 7.79-7.87 (m, 1H), 7.67-7.70 (d, 1H, 9 Hz), 7.61 (s, 1H), 7.41 (s, 2H), 7.20 (s, 1H), 3.82 (s, 3H), 3.47 (s, 3H); MS: m/z 458 (M+1)$^+$.

Example 89

(E)-3-fluoro-N'-((6-(2-fluoropyridin-3-yl) imidazo[1,2-a]pyridin-3-yl) methylene)-N-methylbenzenesulfonohydrazide Yield: 55%; $^1$H NMR (300 MHz, DMSO-d$_6$): δ 9.76 (s, 1H), 8.33-8.35 (d, 1H, J=4.8 Hz), 8.04-8.11 (m, 2H), 7.97 (s, 1H), 7.86-7.89 (d, 1H, J=9.3 Hz), 7.68-7.72 (d, 1H, J=9.3 Hz), 7.59-7.62 (d, 1H, J=7.8 Hz), 7.50-7.60 (m, 1H), 7.36-7.46 (m, 2H), 7.23-7.26 (m, 1H), 3.33 (s, 3H); MS: m/z 428 (M+1)$^+$.

Example 90

(E)-5-chloro-2-fluoro-N'-((6-(2-fluoropyridin-3-yl) imidazo[1,2-a]pyridin-3-yl)methylene)-N-methyl-benzenesulfonohydrazide Yield: 36.9%; $^1$H NMR (300 MHz, DMSO-d$_6$): δ 9.64 (s, 1H), 8.34-8.36 (d, 1H, J=7.5 Hz), 8.09 (s, 1H), 8.01 (s, 1H), 7.96 (s, 1H), 7.77-7.85 (m, 2H), 7.72 (s, 1H), 7.43-7.49 (m, 2H), 7.09-7.13 (d, 1H, J=9.3 Hz), 3.51 (s, 3H); MS: m/z 462 (M+1)$^+$.

Example 91

(E)-5-bromo-N'-((6-(2-fluoropyridin-3-yl) imidazo [1,2-a]pyridin-3-yl) methylene)-2-methoxy-N-methylbenzenesulfonohydrazide Yield: 53%; $^1$H NMR (300 MHz, DMSO-$d_6$): δ 9.60 (s, 1H), 8.34-8.36 (m, 1H), 8.09-8.13 (m, 1H), 7.90-7.92 (m, 2H), 7.77-7.80 (d, 1H, J=9.3 Hz), 7.70-7.72 (m, 1H), 7.49-7.56 (m, 3H), 6.81-6.84 (d, 1H, J=8.7 Hz), 3.88 (s, 3H), 3.55 (s, 3H); MS: m/z 518 (M+1)$^+$.

Example 92

(E)-N'-((6-(2-fluoropyridin-3-yl) imidazo[1,2-a]pyridin-3-yl)methylene)-2,5-dimethoxy-N-methylbenzenesulfonohydrazide Yield: 54.9%; $^1$H NMR (300 MHz, DMSO-$d_6$): δ 9.60 (s, 1H), 8.32-8.33 (d, 1H, J=1.5 Hz), 8.04-8.10 (m, 1H), 7.89 (s, 2H), 7.76-7.79 (m, 1H), 7.59-7.72 (m, 1H), 7.48-7.52 (m, 1H), 7.35-7.36 (d, 1H, J=3 Hz), 6.93-6.97 (dd, 1H, 3&9 Hz), 6.88-6.90 (d, 1H, J=6.9 Hz), 3.83 (s, 3H), 3.58 (s, 3H), 3.55 (s, 3H); MS: m/z 470 (M+1)$^+$.

Example 93

(E)-N'-((6-(2-fluoropyridin-3-yl) imidazo[1,2-a]pyridin-3-yl)methylene)-N, 2-dimethyl-5-(methylsulfonyl)benzenesulfonohydrazide Yield: 47%; $^1$H NMR (300 MHz, DMSO-$d_6$): δ 9.56 (s, 1H), 8.34 (s, 2H), 8.27-8.28 (d, 1H, J=1.8 Hz), 8.14-8.21 (m, 1H), 8.05 (s, 1H), 8.02-8.03 (d, 1H, J=2.1 Hz), 7.86-7.89 (d, 1H, J=9.3 Hz), 7.66-7.76 (m, 2H), 7.54-7.59 (m, 1H), 3.37 (s, 3H), 3.13 (s, 3H), 2.64 (s, 3H); MS: m/z 502 (M+1)$^+$.

Example 94

(E)-N'-((6-(2-fluoropyridin-3-yl) imidazo[1,2-a]pyridin-3-yl)methylene)-N-methylhexane-1-sulfonohydrazide Yield: 61%; $^1$H NMR (300 MHz, DMSO-$d_6$): δ 9.85 (s, 1H), 8.28-8.29 (dd, 1H, J=1.5&3.6 Hz), 8.07-8.08 (d, 1H, J=1.8 Hz), 8.04 (s, 1H), 7.98 (s, 1H), 7.84-7.87 (d, 1H, J=9.3 Hz), 7.66-7.70 (m, 1H), 7.37-7.41 (m, 1H), 3.43 (s, 3H), 3.22-3.27 (m, 2H), 1.78-1.86 (m, 2H), 1.30-1.45 (m, 2H), 1.22-1.27 (m, 4H), 0.82-0.86 (m, 2H); MS: m/z 418 (M+1)$^+$.

Example 95

(E)-N'-((6-(2-fluoropyridin-3-yl) imidazo[1,2-a]pyridin-3-yl)methylene)-2-methoxy-N, 4-dimethylbenzenesulfonohydrazide Yield: 52%; $^1$H NMR (300 MHz, DMSO-$d_6$): δ 9.40 (s, 1H), 8.39-8.41 (d, 1H, J=3.6 Hz), 8.02-8.07 (m, 1H), 7.89 (s, 1H), 7.86 (s, 1H), 7.70-7.80 (d, 1H, J=9 Hz), 7.66-7.69 (d, 1H, J=8.1 Hz), 7.48-7.52 (m, 2H), 6.69 (s, 1H), 6.24-6.26 (d, 1H, J=7.8 Hz), 3.84 (s, 3H), 3.54 (s, 3H), 2.31 (s, 3H); MS: m/z 454 (M+1)$^+$.

Example 96

(E)-2-bromo-N'-((6-(2-fluoropyridin-3-yl) imidazo [1,2-a]pyridin-3-yl) methylene)-N-methylbenzenesulfonohydrazide Yield: 44.77%; $^1$H NMR (300 MHz, DMSO-$d_6$): δ 9.26 (s, 1H), 8.40-8.42 (d, 1H, J=4.2 Hz), 8.08-8.10 (d, 1H, J=7.8 Hz), 7.97-8.02 (m, 1H), 7.93 (s, 2H), 7.78-7.81 (d, 1H, J=9.3 Hz), 7.64-7.67 (d, 1H, J=7.8 Hz), 7.48-7.57 (m, 2H), 7.23-7.28 (m, 1H), 6.81-6.86 (m, 1H), 3.64 (s, 3H); MS: m/z 490 (M+1)$^+$.

Example 97

(E)-2-cyano-N'-((6-(2-fluoropyridin-3-yl) imidazo[1, 2-a]pyridin-3-yl) methylene)-N-methylbenzenesulfonohydrazide Yield: 41%; $^1$H NMR (300 MHz, DMSO-$d_6$): δ 9.39 (s, 1H), 8.37-8.38 (d, 1H, J=3.6 Hz), 8.09-8.12 (d, 1H, J=8.1 Hz), 8.06 (s, 1H), 7.97-8.03 (m, 2H), 7.80-7.83 (d, 2H, J=8.1 Hz), 7.56-7.64 (m, 2H), 7.39-7.49 (m, 2H), 3.60 (s, 3H); MS: m/z 435 (M+1)$^+$.

Example 98

(E)-N'-((6-(2-fluoropyridin-3-yl) imidazo[1,2-a]pyridin-3-yl)methylene)-2-methoxy-N,5-dimethylbenzenesulfonohydrazide Yield: 50%; $^1$H NMR (300 MHz, DMSO-$d_6$): δ 9.67 (s, 1H), 8.34-8.36 (m, 1H), 8.12-8.18 (m, 1H), 7.88 (s, 2H), 7.75-7.83 (m, 1H), 7.58-7.67 (m, 2H), 7.49-7.53 (m, 1H), 7.18-7.21 (dd, 1H, J=2.1&8.4 Hz), 6.79-6.82 (d, 1H, J=8.7 Hz), 3.86 (s, 3H), 3.54 (s, 3H), 1.87 (s, 3H); MS: m/z 454 (M+1)$^+$.

Example 99

N, 2-Dimethyl-5-nitro-N'-((6-(quinolin-3-yl) imidazo[1,2-a]pyridine-3-yl) methylene)benzenesulfonohydrazide The title compound was prepared by following the procedure as described for example 1, using Intermediate 4, methyl hydrazine and 2-methyl-5-nitrobenzene-1-sulfonyl chloride.

Yield: 60%; $^1$H NMR (DMSO-$d_6$; 300 MHz): δ 9.83 (s, 1H), 9.20-9.21 (d, 1H, J=3 Hz), 8.72-8.73 (d, 1H, J=3 Hz), 8.55-8.56 (d, 1H, J=3 Hz), 8.37 (s, 1H), 8.23-8.27 (dd, 1H, J=3, 3 Hz), 8.03-8.10 (m, 4H), 7.90-7.93 (d, 1H, J=9 Hz), 7.81 (m, 1H), 7.66-7.71 (m, 2H), 3.41 (s, 3H), 2.67 (s, 3H); MS: m/z 501 (M+1)$^+$.

Example 100

(E)-5-Fluoro-N,2-dimethyl-N'-((8-methyl-6-(pyridin-3-yl) imidazo[1,2-a]pyridin-3-yl)methylene) benzenesulfonohydrazide To a solution of 8-methyl-6-(pyridin-3-yl)imidazo[1,2-a] pyridine-3-carbaldehyde (Intermediate 5, 80 mg, 0.337 mmol) in ethanol (10 mL) was added methyl hydrazine (0.035 mL, 0.675 mmol) at RT. The reaction mixture was heated at 80° C. for 4 hours. Ethanol was evaporated. Pyridine (5 mL) was added to this residue, followed by addition 2-methyl-5-fluoro benzene sulfonylchloride (105 mg, 0.506 mmol). The reaction mixture was stirred at RT overnight.

Pyridine was evaporated. Water was added to this residue and extracted with dichloromethane. Organic layer was dried over sodium sulfate and evaporated. The crude product was purified by column chromatography (silica gel, 1.5% methanol in chloroform) to obtain the title compound. Yield: 50 mg (27%); $^1$H NMR (CDCl$_3$; 300 MHz): δ 9.41(s, 1H), 8.59 (s, 1H), 8.71 (d, 1H, J=3.9 Hz), 7.99 (s, 1H), 7.97 (m, 1H), 7.94 (s, 1H), 7.66 (dd, 1H, J=8.4, 2.7 Hz), 7.47 (m, 1H), 7.43 (s, 1H), 7.21 (m, 1H), 7.07 (m, 1H), 3.47 (s, 3H), 2.73 (s, 3H), 2.53 (s, 3H); MS: m/z 438 (M+1)$^+$.

The compounds of Examples 101-114 were prepared by following the procedure as described for Example 100, using Intermediate 5, methyl hydrazine and an appropriate sulfonylchloride derivative.

Example 101

(E)-3,5-Difluoro-N-methyl-N'-((8-methyl-6-(pyridin-3-ypimidazo[1,2-a]pyridin-3-yl)methylene)benzenesulfonohydrazide Yield: 28%; $^1$H NMR (CDCl$_3$, 300M Hz): 9.59 (s, 1H), 8.91 (s, 1H) 8.68 (s, 1H), 8.09 (s, 1H,), 7.99 (d, 1H, J=7.5 Hz), 7.93 (s, 1H), 7.49-7.45 (m, 2H), 7.32 (s, 2H), 7.04 (t, 1H, J=10 Hz), 3.33 (s, 3H), 2.74 (s, 3H); MS: m/z 442(M+1)$^+$.

Example 102

(E)-4-Bromo-2,6-difluoro-N-methyl-N'-((8-methyl-6-(pyridin-3-yl)imidazo[1,2-a]pyridin-3-yl)methylene)benzenesulfonohydrazide Yield: 22% $^1$H NMR (CDCl$_3$, 500M Hz): −9.37 (s, 1H), 8.89 (s, 1H) 8.09 (s, 1H), 8.15 (s, 1H), 7.97 (m, 2H), 7.46 (t, 1H, J=6.5 Hz), 7.39 (s, 1H), 7.24 (d, 1H, J=7.5 Hz), 6.72 (t, 1H, J=8.5 Hz), 3.56 (s, 3H), 2.71 (s, 3H); MS: m/z 520(M+1)$^+$.

Example 103

(E)-N,3-dimethyl-N'-((8-methyl-6-(pyridin-3-yl)imidazo[1,2-a]pyridin-3-yl)methylene)benzenesulfonohydrazide Yield: 30%; $^1$H NMR (CDCl$_3$, 300M Hz): 9.72 (s, 1H), 8.96 (s, 1H) 8.71 (d, 1H, J=4.2 Hz), 8.11 (d, 1H, J=7.8 Hz), 8.02 (s, 1H), 7.90 (s, 1H), 7.61 (m, 4H), 7.32 (m, 2H), 3.32 (s, 3H), 2.75 (s, 3H), 2.15 (s, 3H); MS: m/z 420(M+1)$^+$.

Example 104

(E)-2-cyano-N-methyl-N'-((8-methyl-6-(pyridin-3-yl)imidazo[1,2-a]pyridin-3-yl)methylene)benzenesulfonohydrazide Yield: 40 mg (28%); $^1$H NMR (CDCl$_3$, 300M Hz): 9.19 (s, 1H), 8.76 (m, 2H), 8.17 (d, 1H, J=7.8 Hz), 8.06 (s, 1H), 7.96 (m, 2H), 7.81 (d, 1H, J=7.8 Hz), 7.62 (t, 1H, J=7.5 Hz), 7.54 (m, 3H), 3.62 (s, 3H), 2.72 (s, 3H); MS: m/z 431(M+1)$^+$.

Example 105

(E)-3-cyano-4-fluoro-N-methyl-N'-((8-methyl-6-(pyridin-3-yl)imidazo[1,2-a]pyridin-3-yl)methylene)benzenesulfonohydrazide Yield: 23%; $^1$H NMR (CDCl$_3$; 300M Hz): 9.56 (s, 1H), 8.92 (d, 1H, J=1.5 Hz), 8.73 (d, 1H, J=4.5 Hz), 8.13 (s, 1H), 8.08 (m, 3H), 7.97 (s, 1H), 7.51 (m, 2H), 7.28 (m, 1H), 3.335 (s, 3H), 2.770 (s, 3H); MS: m/z 449(M+1)$^+$.

Example 106

(E)-3-cyano-N-methyl-N'-((8-methyl-6-(pyridin-3-yl)imidazo[1,2-a]pyridin-3-yl)methylene)benzenesulfonohydrazide Yield: 27.58%; $^1$H NMR (CDCl$_3$; 300M Hz): 9.57 (s, 1H), 8.91 (d, 2H, J=2.1 Hz), 8.73 (dd, 1H, J=4.8 Hz, 1.5 Hz), 8.11 (s, 1H), 8.07 (m, 3H), 7.95 (s, 1H), 7.81 (d, 1H, J=7.8 Hz), 7.53 (m, 3H), 3.33 (s, 3H), 2.76 (s, 3H); MS: m/z 431(M+1)$^+$.

Example 107

(E)-4-Bromo-N,3-dimethyl-N'-((8-methyl-6-(pyridin-3-yl)imidazo[1,2-a]pyridin-3-yl)methylene)benzenesulfonohydrazide Yield: 38%; $^1$H NMR (CDCl$_3$; 300M Hz): 9.69 (s, 1H), 8.98 (d, 1H, J=2.1 Hz), 8.72 (d, 1H, J=4.8 Hz), 8.08 (m, 2H), 7.92 (s, 1H), 7.61 (s, 1H), 7.53 (m, 4H), 3.31 (s, 3H), 2.76 (s, 3H), 2.17 (s, 3H); MS: m/z 498 (M+1)$^+$.

Example 108

(E)-3-Methoxy-N-methyl-N'-((8-methyl-6-(pyridin-3-yl)imidazo[1,2-a]pyridin-3-yl)methylene)benzenesulfonohydrazide Yield: 31%; $^1$H NMR (CDCl$_3$; 300M Hz): 9.77 (s, 1H), 8.95 (d, 1H, J=2.1 Hz), 8.70 (dd, 1H, J=2.1 Hz, 1.5 Hz), 8.121 (m, 1H), 7.91 (s, 1H), 7.52 (m, 2H), 7.40 (d, 1H, J=7.8 Hz), 7.29 (m, 2H), 7.05 (dd, 1H, J=2.4 Hz, 8.4 Hz), 3.56 (s, 3H), 3.31 (s, 3H), 2.78 (s, 3H); MS: m/z 436 (M+1)$^+$.

Example 109

(E)-N-methyl-N'-((8-methyl-6-(pyridin-3-yl)imidazo[1,2-a]pyridin-3-yl)methylene)-3-nitrobenzenesulfonohydrazide Yield: 34%; $^1$H NMR (CDCl$_3$; 300M Hz): 9.60 (s, 1H), 8.92 (d, 1H, J=1.8 Hz), 8.72 (dd, 1H, J=4.8 Hz, 1.2 Hz), 8.63 (d, 1H, J=1.8 Hz), 8.39 (dd, 1H, J=8.4 Hz, 1.2 Hz), 8.16 (m, 3H), 7.951 (s, 1H), 7.62 (t, 1H, J=8.1 Hz), 7.51 (m, 2H), 3.55 (s, 3H), 2.76 (s, 3H); MS: m/z 451 (M+1)$^+$.

Example 110

(E)-3-Chloro-N-methyl-N'-((8-methyl-6-(pyridin-3-yl)imidazo[1,2-a]pyridin-3-yl)methylene)benzenesulfonohydrazide Yield: 31%; $^1$H NMR (CDCl$_3$; 300M Hz): 9.63 (s, 1H), 8.94 (d, 1H, J=1.8 Hz), 8.72 (d, 1H, J=4.8 Hz), 8.08 (m, 2H), 7.93 (s, 1H), 7.77 (s, 1H), 7.71 (d, 1H, J=7.8 Hz), 7.52 (t, 3H, J=6.3 Hz), 7.33 (m, 1H), 3.32 (s, 3H), 2.76 (s, 3H); MS: m/z 440 (M+1)$^+$.

Example 111

(E)-N-methyl-N'-((8-methyl-6-(pyridin-3-yl)imidazo[1,2-a]pyridin-3-yl)methylene)-3-(trifluoromethyl)benzenesulfonohydrazide Yield: 34%; $^1$H NMR (CDCl$_3$; 300M Hz): 9.64 (s, 1H), 8.93 (s, 1H), 8.70 (s, 1H), 8.08 (m, 5H), 7.79 (d, 1H, J=7.2 Hz), 7.51 (s, 3H), 3.33 (s, 3H), 2.76 (s, 3H); MS: m/z 474 (M+1)$^+$.

Example 112

(E)-2-Bromo-4,6-difluoro-N-methyl-N'-((8-methyl-6-(pyridin-3-ypimidazo[1,2-a]pyridin-3-yl)methylene)benzenesulfonohydrazide Yield: 53%; $^1$H NMR (CDCl$_3$; 300M Hz): 9.39 (s, 1H), 8.83 (d, 1H, J=1.8 Hz), 8.71 (dd, 1H, J=4.8 Hz, 1.5 Hz), 7.99 (s, 1H), 7.96 (t, 1H, J=1.8 Hz), 7.93 (s, 1H), 7.49 (m, 1H), 7.41 (s, 1H), 7.26 (m, 1H), 6.77 (m, 1H), 3.58 (s, 3H), 2.73 (s, 3H); MS: m/z 522(M+2)$^+$.

Example 113

(E)-4-Chloro-N-methyl-N'-((8-methyl-6-(pyridin-3-yl)imidazo[1,2-a]pyridin-3-yl)methylene)-3-nitrobenzenesulfonohydrazide Yield: 20.7%; $^1$H NMR (CDCl$_3$; 300M Hz): 9.57 (s, 1H), 8.94 (d, 1H, J=2.1 Hz), 8.72 (d, 1H, J=4.5 Hz), 8.28 (d, 1H, J=2.1 Hz), 8.13 (s, 1H), 8.03 (m, 3H), 7.58 (d, 1H, J=8.4 Hz), 7.52 (m, 2H), 3.34 (s, 3H), 2.76 (s, 3H; MS: m/z 485(M+1)$^+$.

Example 114

(E)-2-Bromo-4-fluoro-N-methyl-N'-((8-methyl-6-(pyridin-3-yl)imidazo[1,2-a]pyridin-3-yl)methylene)benzenesulfonohydrazide Yield: 45%; $^1$H NMR (CDCl$_3$, 300M Hz): 9.15 (s, 1H), 8.83 (d, 1H, J=1.8 Hz), 8.78 (d, 1H, J=3.9 Hz), 8.24 (m, 1H), 7.94 (d, 3H, J=9.9 Hz), 7.55 (m, 1H), 7.39 (d, 1H, J=2.4 Hz), 7.36 (s, 1H), 6.69 (m, 1H), 3.63 (s, 3H), 2.71 (s, 3H); MS: m/z 502(M+1)$^+$.

Example 115

(E)-N'-((6-(1H-indol-2-yl)imidazo[1,2-a]pyridin-3-yl)methylene)-5-fluoro-N,2-dimethylbenzenesulfonohydrazide To a solution of 6-(1H-indol-2-yl)imidazo[1,2-a]pyridine-3-carbaldehyde (Intermediate 6, 115 mg, 0.3691 mmol) in ethanol (10 mL) was added methyl hydrazine (0.04 mL, 0.7395 mmol) at RT. The reaction mixture was heated at 80° C. for 4 h. Ethanol was evaporated. Pyridine (5 mL) was added to this residue, followed by addition of 2-methyl-5-fluoro benzene sulfonylchloride (0.07 mL, 0.5535 mmol). The reaction mixture was stirred at RT overnight. Pyridine was evaporated. Water was added to this residue and extracted with dichloromethane. Organic layer was dried over sodium sulfate and evaporated. The crude product was purified by column chromatography (Silica gel, 1.5% methanol in chloroform) to obtain the title compound. Yield: 28 mg (17%); $^1$H NMR (DMSO-d$_6$; 500 MHz): δ 11.83 (s, 1H), 9.09 (s, 1H), 9.81 (s, 1H), 8.34 (s, 1H), 8.27 (d, 1H, J=9.5 Hz), 8.08 (d, 1H, J=9.5 Hz), 7.74 (d, 1H, J=6.5 Hz), 7.61 (d, 1H, J=8 Hz), 7.43 (m, 3H), 7.18 (t, 1H, J=8), 7.07 (t, 1H, J=7.5 Hz), 6.91 (s, 1H), 3.48 (s, 3H); MS: m/z 460 (M–1)$^+$.

Example 116

(E)-5-fluoro-N,2-dimethyl-N'-((6-(1-methyl-1H-indol-3-yl) imidazo[1,2-a]pyridin-3-yl)methylene)benzenesulfonohydrazide To a solution of N'-((6-(1H-indol-3-yl) imidazo[1,2-a]pyridin-3-yl)methylene)-5-fluoro-N,2-dimethylbenzenesulfonohydrazide (50 mg, 1084 mmoles) in DMF (3 ml) was added NaH (6.5 mg, 0.1626 mmoles). The solution was stirred for 15 minutes and then methyl iodide was added to it. The reaction was quenched with methanol. The reaction mixture was evaporated to dryness. The residue obtained was dissolved in EtOAc washed with water and brine. EtOAc layer was separated, dried over sodium sulfate and evaporated. Crude material was purified by column chromatography (100-200 mesh size silica gel, 1.0% MeOH in CHCl$_3$). Yield: 25 mg (49%) $^1$H NMR (CDCl$_3$, 500 MHz): δ 9.28 (s, 1H), 8.01 (s, 1H) 7.91 (s, 1H), 7.77 (d, 1H, J=9 Hz), 7.70 (d, 1H, J=7.5 Hz), 7.59 (d, 1H, J=8 Hz), 7.49 (d, 1H, J=9.5 Hz), 7.42 (d, 1H, J=8 Hz), 7.33 (t, 1H, J=7 Hz), 7.21 (t, 1H, J=6 Hz), 7.07 (m, 1H), 6.84 (m, 1H), 6.57 (s, 1H), 3.75 (s, 3H), 3.44 (s, 3H), 2.71 (s, 3H); MS: m/z 476(M+1)$^+$ The compounds of Examples 117-124 were prepared by following the procedure as described for Example 1, using Intermediate 7, methyl hydrazine and an appropriate sulfonylchloride derivative.

Example 117

2-Cyano-N-methyl-N'-((7-methyl-6-(pyridin-3-yl)imidazo[1,2-a]pyridin-3-yl)methylene) benzenesulfonohydrazide Yield: 24.62%; $^1$H NMR (DMSO-d$_6$; 300 MHz): δ 8.83 (s, 1H), 8.75-8.77 (dd, 1H, J=4.8 Hz, 1.5 Hz), 8.60 (s, 1H), 8.40 (s, 1H), 8.02 (s, 2H), 7.88-7.92 (m, 1H), 7.81-7.84 (d, 1H, J=8.1 Hz), 7.76-7.79 (dd, 1H, J=7.5 Hz, 0.6 Hz), 7.73 (s, 1H), 7.61-7.65 (dd, 1H, J=7.8 Hz, 5.1 Hz), 7.48-7.43 (m, 1H), 3.44 (s, 3H), 2.27 (s, 3H); MS: m/z 431.1 (M+1)

Example 118

5-Fluoro-N, 2-dimethyl-N'-((7-methyl-6-(pyridin-3-yl) imidazo[1,2-a]pyridin-3-yl)methylene) benzenesulfonohydrazide Yield: 38%; $^1$H NMR (DMSO-d$_6$; 300 MHz): δ 8.98 (s, 1H), 8.70-8.72 (dd, 1H, J=4.8 Hz, 1.5 Hz), 8.607-8.612 (d, 1H, J=10.5 Hz), 7.97 (s, 1H), 7.85-7.87 (m, 2H), 7.71 (s, 1H), 7.55-7.60 (dd, 1H, J=7.5 Hz, 4.8 Hz), 7.42-7.34 (m, 3H), 3.39 (s, 3H), 2.41 (s, 3H), 2.28 (s, 3H); MS: m/z 438.1(M+1)$^+$.

Example 119

N, 3-dimethyl-N'-((7-methyl-6-(pyridin-3-yl) imidazo[1,2-a]pyridin-3-yl)methylene)benzenesulfonohydrazide Yield: 34%; $^1$H NMR (DMSO-d$_6$; 300 MHz): δ 9.20 (s, 1H), 8.73-8.75 (m, 2H), 8.26 (s, 1H), 7.97-8.02 (m, 1H), 7.97 (s, 1H), 7.74 (s, 1H), 7.61-7.65 (dd, 1H, J=8.1 Hz, 5.1 Hz), 7.47 (s, 1H), 7.41-7.43 (m, 2H), 7.20-7.25 (t, 1H, J=7.5 Hz), 3.24 (s, 3H), 2.33 (s, 3H), 2.20 (s, 3H); MS: m/z 420.1(M+1)+.

Example 120

3-Fluoro-N-methyl-N'-((7-methyl-6-(pyridin-3-yl) imidazo[1,2-a]pyridin-3-yl)methylene) benzenesulfonohydrazide Yield: 51.48%; $^1$H NMR (DMSO-d$_6$; 300 MHz): δ 9.15 (s, 1H), 8.71-8.74 (m, 2H), 8.31 (s, 1H), 7.99 (s, 1H), 7.96-7.97 (m, 1H), 7.75 (s, 1H), 7.61-7.64 (dd, 1H, J=7.8 Hz, 2.4 Hz), 7.46-7.50 (m, 4H), 3.27 (s, 3H), 2.32 (s, 3H); MS: m/z 424.1 (M+1)+.

Example 121

3-Chloro-N-methyl-N'-((7-methyl-6-(pyridin-3-yl) imidazo[1,2-a]pyridin-3-yl)methylene)benzenesulfonohydrazide Yield: 40%; $^1$H NMR (DMSO-d$_6$; 300 MHz): δ 9.18 (s, 1H), 8.72-8.74 (m, 2H), 8.30 (s, 1H), 7.98-8.01 (m, 2H), 7.76 (s, 1H), 7.70-7.72 (d, 1H, J=8.1 Hz), 7.60-7.67 (m, 3H), 7.41-7.47 (m, 1H), 3.26 (s, 3H), 2.33 (s, 3H); MS: m/z 440.1 (M+1)+.

Example 122

N-methyl-N'-((7-methyl-6-(pyridin-3-yl) imidazo[1, 2-a]pyridin-3-yl)methylene)-3-(trifluoromethyl)benzenesulfonohydrazide Yield: 23%; $^1$H NMR (DMSO-d$_6$; 300 MHz): δ 9.21 (s, 1H), 8.71-8.73 (m, 2H), 8.30 (s, 1H), 8.02-8.05 (d, 1H, J=8.1 Hz), 7.99 (s, 1H), 7.97 (s, 1H), 7.92 (s, 1H), 7.47 (s, 1H), 7.76 (s, 1H), 7.66-7.72 (t, 1H, J=7.8 Hz, 7.5 Hz), 7.58-7.62 (dd, 1H, J=7.8 Hz, 4.8 Hz), 3.24 (s, 3H), 2.34 (s, 3H).

Example 123

3-Bromo-N-methyl-N'-((7-methyl-6-(pyridin-3-yl) imidazo[1,2-a]pyridin-3-yl)methylene)benzenesulfonohydrazide Yield: 26%; $^1$H NMR (DMSO-d$_6$; 300 MHz): δ 8.79-8.80 (dd, 1H, J=4.8 Hz, 1.2 Hz), 8.72 (s, 1H), 8.56-8.57 (d, 1H, J=2.1 Hz), 8.26 (s, 1H), 7.96 (s, 1H), 7.86-7.89 (m, 1H), 7.76-7.79 (d, 1H, J=8.1 Hz), 7.72-7.75 (dd, 1H, J=7.8 Hz, 1.2 Hz), 7.69 (s, 1H), 7.64-7.67 (m, 1H), 7.36-7.41 (m, 1H), 6.81-6.86 (t, 1H, J=7.8 Hz, 7.5 Hz), 3.52 (s, 3H), 2.25 (s, 3H); MS: m/z 483.6(M+1)+.

Example 124

5-Fluoro-N, 2-dimethyl-N'-((7-methyl-6-(pyridin-3-yl)imidazo[1,2-a]pyridin-3-yl)methylene)benzenesulfonohydrazide Yield: 42.57%; $^1$H NMR (DMSO-d$_6$; 300 MHz): δ 8.96 (s, 1H), 8.66-8.68 (dd, 1H, J=4.8 Hz, 1.5 Hz), 8.539-8.544 (d, 1H, J=1.5 Hz), 8.440-8.448 (d, 1H, J=2.4 Hz), 8.32 (s, 1H), 8.26-8.32 (dd, 1H, J=8.4 Hz, 2.4 Hz), 7.98 (s, 1H), 7.83-7.87 (m, 1H), 7.72 (s, 1H), 7.62-7.65 (d, 1H, J=9 Hz), 7.51-7.55 (dd, 1H, J=7.8 Hz, 4.8 Hz), 2.59 (s, 3H), 2.26 (s, 3H), 2.50 (s, 3H); MS: m/z 465.1(M+1)+.

Example 125

N'-((6-(2,4-dimethoxypyrimidin-5-yl) imidazo[1,2-a] pyridin-3-yl)methylene)-5-fluoro-N, 2-dimethylbenzenesulfonohydrazide The title compound was prepared by following the procedure as described for example 1, using Intermediate 8, methyl hydrazine and 2-methyl-5-fluorobenzene-1-sulfonyl chloride.

Yield: 7%; $^1$H NMR (DMSO-d$_6$; 300 MHz): δ 9.21-9.22 (d, 1H, J=0.6 Hz), 8.39 (s, 1H), 8.29 (s, 1H), 8.02 (s, 1H), 7.78-7.81 (m, 1H, J=9.6 Hz, 0.6 Hz), 7.58-7.61 (dd, 1H, J=9.3 Hz, 1.8 Hz), 7.49-7.53 (dd, 1H, J=8.7 Hz, 3 Hz), 7.41-7.43 (m, 1H), 7.34-7.39 (m, 1H), 4.00 (s, 3H), 3.99 (s, 3H), 3.42 (s, 3H), 2.44 (s, 3H); MS: m/z 485.2 (M+1)+.

The compounds of Examples 126 and 127 were prepared by following the procedure as described for Example 1, using Intermediate 9, methyl hydrazine and an appropriate sulfonylchloride derivative.

Example 126

(E)-5-Fluoro-N,2-dimethyl-N'-((5-methyl-6-(pyridin-3-yl)imidazo[1,2-a]pyridin-3-yl)methylene)benzenesulfonohydrazide Yield: 24%; $^1$H NMR (CDCl$_3$; 300M Hz): δ 8.71 (m, 1H), 8.62 (d, 1H, J=1.8 Hz), 8.34 (s, 1H), 8.01 (s, 1H), 7.75 (dd, 1H, J=8.4 Hz, 2.7 Hz), 7.68 (m, 2H), 7.47 (m, 1H), 7.33 (m, 3H), 3.37 (s, 3H), 2.64 (s, 3H), 2.63 (s, 3H); MS: m/z 438 (M+1)+.

Example 127

(E)-N,3-dimethyl-N'-((5-methyl-6-(pyridin-3-yl) imidazo[1,2-a]pyridin-3-yl)methylene)benzenesulfonohydrazide Yield: 17%; $^1$H NMR (CDCl$_3$; 300 MHz): δ 8.71 (m, 1H), 8.64 (d, 1H, J=1.5 Hz), 8.62 (s, 1H), 8.12 (s, 1H), 7.71 (m, 5H), 7.47 (m, 3H), 7.26 (d, 1H, J=9 Hz), 3.20 (s, 3H), 2.73 (s, 3H), 2.45 (s, 3H); MS: m/z 420(M+1)+.

The compounds of Examples 128-131 were prepared by following the procedure as described for Example 1, using Intermediate 10, methyl hydrazine and an appropriate sulfonylchloride derivative.

Example 128

(E)-5-fluoro-N,2-dimethyl-N'-((6-(6-methylpyridin-3-yl)imidazo[1,2-a]pyridin-3-yl)methylene)benzenesulfonohydrazide Yield: 38%; $^1$H NMR (CDCl$_3$; 300M Hz): δ 9.50 (s, 1H), 8.74 (s, 1H), 7.99 (s, 1H), 7.91 (s, 1H), 7.87 (dd, 1H, J=8.1 Hz, 2.4 Hz), 7.78 (d, 1H, J=9 Hz), 7.71 (dd, 1H, J=8.4 Hz, 2.7 Hz), 7.59 (dd, 1H, J=9.6 Hz, 1.8 Hz), 7.35 (d, 1H, J=8.1 Hz), 7.25 (m, 1H), 7.08 (m, 1H), 3.45 (s, 3H), 2.68 (s, 3H), 2.53 (s, 3H); MS: m/z 438 (M+1)+.

Example 129

(E)-N-methyl-N'-((6-(6-methylpyridin-3-yl)imidazo [1,2-a]pyridin-3-yl)methylene)-2-(trifluoromethoxy) benzenesulfonohydrazide Yield: 22%; $^1$H NMR (CDCl$_3$; 300M Hz): δ 9.36 (s, 1H), 8.72 (s, 1H), 8.10 (dd, 1H, J=7.8 Hz, 1.8 Hz), 7.94 (s, 1H), 7.90 (m, 2H), 7.79 (d, 1H, J=9 Hz), 7.57 (m, 2H), 7.41 (d, 1H, J=7.8 Hz), 7.34 (m, 1H), 7.04 (m, 1H), 3.57 (s, 3H), 2.72 (s, 3H); MS: m/z 490 (M+1)+.

Example 130

(E)-5-Fluoro-2-methoxy-N-methyl-N'-((6-(6-methylpyridin-3-yl)imidazo[1,2-a]pyridin-3-yl)methylene)benzenesulfonohydrazide Yield: 22%; $^1$H NMR (CDCl$_3$; 300 MHz): δ 9.50 (s, 1H), 8.773 (s, 1H), 7.91 (s, 1H), 7.88 (m, 2H), 7.79 (d, 1H, J=9 Hz), 7.71 (dd, 1H, J=7.8 Hz, 2.7 Hz), 7.61 (dd, 1H, J=9.3 Hz, 1.8 Hz), 7.42 (d, 1H, J=8.1 Hz), 7.13 (m, 1H), 6.90 (m, 1H), 3.85 (s, 3H), 3.55 (s, 3H), 2.69 (s, 3H); MS m/z 454(M+1)+.

Example 131

(E)-N,2-dimethyl-N'-((6-(6-methylpyridin-3-yl)imidazo[1,2-a]pyridin-3-yl)methylene)benzenesulfonohydrazide Yield: 24%; $^1$H NMR (CDCl$_3$; 300 MHz): δ 9.45 (s, 1H), 8.73 (s, 1H), 8.01 (d, 1H, J=7.5 Hz), 7.95 (s, 1H), 7.89 (m, 2H), 7.79 (d, 1H, J=9.3 Hz), 7.58 (dd, 1H, J=9.3 Hz, 1.8 Hz), 7.39 (m, 2H), 7.25 (m, 1H), 6.93 (m, 1H), 3.47 (s, 3H), 2.70 (s, 3H), 2.56 (s, 3H); MS m/z 420 (M+1)+.

The compounds of Examples 132 and 133 were prepared by following the procedure as described for Example 1, using Intermediate 11, methyl hydrazine and an appropriate sulfonylchloride derivative.

Example 132

(E)-5-fluoro-N'-((6-(5-fluoropyridin-3-yl) imidazo[1,2-a]pyridin-3-yl)methylene)-N, 2-dimethylbenzenesulfonohydrazide Yield: 37%; $^1$H NMR (DMSO-d$_6$; 300 MHz): δ 9.63 (s, 1H), 8.72 (s, 1H), 8.58-8.59 (d, 1H, J=2.4 Hz), 7.86-8.00 (m, 3H), 7.59-7.70 (m, 3H), 7.28 (s, 1H), 7.09-7.12 (m, 1H), 3.48 (s, 3H), 2.55 (s, 3H); MS: m/z 441 (M+1)+.

Example 133

(E)-5-Fluoro-N'-((6-(5-fluoropyridin-3-yl) imidazo[1,2-a]pyridin-3-yl) methylene)-2-methoxy-N-methylbenzenesulfonohydrazide Yield: 54%; $^1$H NMR (DMSO-d$_6$; 300 MHz): δ 9.62 (s, 1H), 8.75 (s, 1H), 8.60-8.61 (d, 1H, J=2.7 Hz), 7.91 (s, 2H), 7.68-7.83 (m, 3H), 7.58-7.61 (dd, 1H, J=1.8 & 9.3 Hz), 7.09-7.16 (m, 1H), 6.90-6.91 (m, 1H), 3.86 (s, 3H), 3.56 (s, 3H); MS m/z 457 (M+1)+.

Example 134

(E)-5-Fluoro-N'-((6-(6-fluoro-5-methylpyridin-3-yl) imidazo[1,2-a]pyridin-3-yl)methylene)-N,2-dimethylbenzenesulfonohydrazide The title compound was prepared by following the procedure as described for Example 1, using Intermediate 12 and 5-fluoro-2-methylbenzene-1-sulfonyl chloride.

Yield: 40 mg (26%); $^1$H NMR (CDCl$_3$; 300 MHz): δ 9.62 (s, 1H), 8.25 (s, 1H), 7.97 (m, 3H), 7.81 (d, 1H, J=9.6 Hz), 7.64 (m, 2H), 7.26 (m, 1H), 7.11 (m, 1H), 3.46 (s, 3H), 2.54 (s, 3H); MS: m/z 456(M+1)+.

Example 135

(E)-N'-((6-(6-Chloropyridins-3-yl)imidazo[1,2-a]pyridin-3-yl)methylene)-5-fluoro-N,2-dimethylbenzenesulfonohydrazide The title compound was prepared by following the procedure as described for Example 1, using Intermediate 13 and 5-fluoro-2-methylbenzene-1-sulfonyl chloride.

Yield: 26%; $^1$H NMR (CDCl$_3$; 300M Hz): δ 9.60 (s, 1H), 8.63 (s, 1H), 7.97 (m, 3H), 7.83 (d, 1H, J=9 Hz), 7.67 (m, 1H), 7.59 (t, 2H, J=10.5 Hz), 7.24 (m, 1H), 7.12 (m, 1H), 3.47 (s, 3H), 2.53 (s, 3H); MS m/z 457(M+1)+.

Example 136

(E)-V-((6-(1H-Pyrrol-2-yl)imidazo[1,2-a]pyridin-3-yl)methylene)-5-fluoro-N,2-dimethylbenzenesulfonohydrazide The title compound was prepared by following the procedure as described for Example 1, using Intermediate 14 and 5-fluoro-2-methylbenzene-1-sulfonyl chloride.

Yield: 20%; $^1$H NMR (CDCl$_3$, 300M Hz): δ 9.89 (s, 1H), 8.97 (s, 1H), 8.19 (m, 6H), 6.96 (s, 2H), 6.35 (s, 1H), 3.38 (s, 3H), 2.77 (s, 3H); MS m/z 412M+1)+.

Example 137

(E)-5-fluoro-N'-((6-(6-methoxypyridin-3-yl)imidazo[1,2-a]pyridin-3-yl)methylene)-N,2-dimethylbenzenesulfonohydrazide The title compound was prepared by following the procedure as described for Example 1, using 6-(6-methoxypyridin-3-yl)imidazo[1,2-a]pyridine-3-carbaldehyde, and 5-fluoro-2-methylbenzene-1-sulfonyl chloride.

Yield: 23%; $^1$H NMR (CDCl$_3$; 300M Hz): 9.48 (s, 1H), 8.389 (s, 1H), 7.98 (s, 1H), 7.91 (bs, 1H), 7.85 (m, 2H), 7.73 (m, 1H), 7.59 (m, 1H), 7.25 (m, 1H), 7.11 (m, 1H), 6.96 (d, 1H, J=8.4 Hz), 4.04 (s, 3H), 3.47 (s, 3H), 2.53 (s, 3H); MS m/z 454(M+1)+.

Example 138

(E)-5-Fluoro-N-((6-(2-methoxypyrimidin-5-yl) imidazo[1,2-a]pyridine-3-yl)methylene)-N, 2-dimethylbenzenesulfonohydrazide The title compound was prepared by following the procedure as described for Example 1, using Intermediate 15 and 5-fluoro-2-methylbenzene-1-sulfonyl chloride.

Yield: 47%; $^1$H NMR (300 MHz, DMSO-d$_6$): δ 9.49 (s, 1H), 8.75 (s, 2H), 7.99 (s, 1H), 7.94 (s, 1H), 7.83-7.86 (d, 1H, J=9.3 Hz), 7.67-7.70 (dd, 1H, J=2.7 &8.4 Hz), 7.51-7.55 (dd, 1H, J=1.8 &9.3 Hz), 7.23-7.26 (m, 1H), 7.08-7.14 (m, 1H), 4.15 (s, 3H), 3.48 (s, 3H), 2.54 (s, 3H); MS: m/z 455 (M+1)+.

Example 139

(E)-5-fluoro-N, 2-dimethyl-N'-((6-(5-(trifluoromethyl)pyridin-3-yl) imidazo[1,2-a]pyridin-3-yl)methylene) benzenesulfonohydrazide The title compound was prepared by following the procedure as described for Example 1, using Intermediate 16 and 5-fluoro-2-methylbenzene-1-sulfonyl chloride.
Yield: 40%; $^1$H NMR (300 MHz, DMSO-d$_6$): δ 9.72 (s, 1H), 9.09 (s, 1H), 8.99 (s, 1H), 8.24 (s, 1H), 7.96-7.99 (d, 2H, J=9.6 Hz), 7.85-7.88 (d, 1H, J=9 Hz), 7.59-7.65 (m, 2H), 7.21-7.23 (m, 1H), 7.06-7.09 (m, 1H), 3.48 (s, 3H), 2.54 (s, 3H); MS: m/z 513 (Na$^+$).

Example 140

(E)-5-Fluoro-N, 2-dimethyl-N'-((6-(pyrimidin-5-yl) imidazo[1,2-a]pyridin-3-yl)methylene)benzenesulfonohydrazide The title compound was prepared by following the procedure as described for Example 1, using Intermediate 17 and 5-fluoro-2-methylbenzene-1-sulfonyl chloride.
Yield: 47.87%; $^1$H NMR (300 MHz, DMSO-d$_6$): δ 9.62 (s, 1H), 9.34 (s, 1H), 9.01 (s, 2H), 8.00 (s, 1H), 7.96 (s, 1H), 7.85-7.88 (d, 1H, J=9.6 Hz), 7.64-7.67 (dd, 1H, J=2.7 & 8.4 Hz), 7.56-7.60 (dd, 1H, J=1.8 & 9.3 Hz), 7.23-7.25 (m, 1H), 7.09-7.10 (m, 1H), 3.48 (s, 3H), 2.55 (s, 3H); MS: m/z 425 (M+1)$^+$.

Example 141

(E)-N-benzyl-1-methyl-2-((6-(pyridin-3-yl)imidazo[1,2-a]pyridin-3-yl)methylene)hydrazinecarboxamide Methyl hydrazine (41.25 mg, 0.8968 mmoles) was added to ethanolic solution of 6-(pyridin-3-yl)imidazo[1,2-a]pyridine-3-carbaldehyde (100 mg, 0.4484 mmoles) at RT. The reaction mixture was heated at 85° C. for 1.5 hours. The solvent was then evaporated. The residue was dissolved in ethanol (5 ml), followed by addition of benzyl isocyanate (140.58 mg, 0.6726 mmoles). The reaction mixture was refluxed for 2 hours, then the solvent was evaporated. Water was poured into the residue and the aqueous solution was extracted with chloroform. Organic layer was separated, washed with water and brine and dried over sodium sulfate. The crude product was purified by column chromatography (100-200 mesh size silica gel, 1.5% methanol in chloroform). Yield: 41%; $^1$HNMR (DMSO-d$_6$; 300 MHz): δ 9.48 (s, 1H), 9.05 (s, 1H), 8.58 (s, 1H), 8.21 (m, 3H), 7.98 (s, 1H), 7.80 (s, 2H), 7.29 (m, 6H), 4.39 (d, 2H, J=4.2 Hz), 3.35 (s, 3H); MS: m/z 384 (M+1)$^+$.

Example 142

(E)-1-methyl-2-((6-(pyridin-3-yl)imidazo[1,2-a]pyridin-3-yl)methylene)-N-p-tolylhydrazinecarboxamide The title compound was prepared according to the procedure as set forth in example 141, except that 1-isocyanato-4-methylbenzene was used in place of benzyl isocyanate to yield 51% of the title compound. $^1$H NMR (DMSO-d$_6$; 300 MHz): δ 9.56 (s, 1H), 9.23 (s, 1H), 9.05 (s, 1H), 8.61 (s, 1H), 8.30 (m 3H), 7.84 (s, 1H), 7.49 (m, 3H), 7.11 (d, 1H, J=7.2 Hz), 3.41 (s, 3H), 2.28 (s, 3H); MS: m/z 385 (M+1)$^+$.

Example 143

(E)-N-(2-fluoro-5-methylphenyl)-1-methyl-2-((6-(pyridin-3-yl) imidazo[1,2-a]pyridin-3-yl)methylene) hydrazinecarboxamide The title compound was prepared according to the procedure as set forth in example 141, except that 1-fluoro-2-isocyanato-4-methylbenzene was used in place of benzyl isocyanate to yield 35% of the title compound. $^1$HNMR (DMSO-d$_6$; 300 MHz): δ 9.46 (s, 1H), 8.99 (d, 2H, J=6.3 Hz), 8.60 (s, 1H), 8.34 (s, 1H), 8.19 (s, 1H), 7.84 (m, 3H), 7.40 (s, 1H), 7.02 (m, 2H), 3.43 (s, 3H), 2.298 (s, 3H); MS: m/z 403(M+1)$^+$.

Example 144

(E)-N-(5-fluoro-2-methylphenyl)-1-methyl-2-((6-(pyridin-3-yl) imidazo[1,2-a]pyridin-3-yl)methylene) hydrazinecarboxamide The title compound was prepared according to the procedure as set forth in example 141, except that 4-fluoro-2-isocyanato-1-methylbenzene was used in place of benzyl isocyanate to yield 28% of the title compound. $^1$HNMR (DMSO-d$_6$; 300 MHz): δ 9.43 (s, 1H), 9.00 (d, 2H, J=19.5 Hz), 8.61 (s, 1H), 8.36 (s, 1H), 8.20 (m, 2H), 7.83 (m, 2H), 7.62 (d, 1H, J=10.5 Hz)), 7.42 (s, 1H), 7.17 (s, 1H), 6.85 (s, 1H), 3.45 (s, 3H), 2.03 (s, 3H); MS: m/z 403(M+1)$^+$.

Example 145

N-benzyl-2-((6-bromoimidazo[1,2-a]pyridin-3-yl) methylene)-1-methylhydrazinecarboxamide 6-bromoimidazo[1,2-a]pyridine-3-carbaldehyde (step 1 of Intermediate 1, 100 mg, 0.44 mmoles) was dissolved in ethanol followed by addition of methyl hydrazine (41.25 mg, 0.89 mmoles) at RT. The reaction mixture was heated at 85° C. for 1.5 hours. Solvent was evaporated. The residue so obtained was dissolved in ethanol (5 ml), followed by addition of benzyl isocyanate (140.58 mg, 0.67 mmoles). The reaction was refluxed for 2 hours and then the solvent was evaporated. Water was poured into the residue and the aqueous solution was extracted with chloroform. Organic layer was washed with water and brine, separated and dried over sodium sulfate. The crude product was purified by column chromatography (100-200 mesh size silica gel, 1.5% MeOH in CHCl$_3$). Yield: 70 mg (40.93%); $^1$HNMR (DMSO-d$_6$; 300 MHz): δ 9.36 (s, 1H), 8.14-8.15 (d, 2H, J=5.4 Hz), 7.93 (bs, 1H), 7.65-7.68 (d, 1H, J=9 Hz), 7.48-7.51 (d, 1H, J=9 Hz), 7.23-7.35 (m, 5H), 4.39-4.41 (d, 2H, J=5.1 Hz), 3.35 (s, 3H); MS: m/z 386.8(M+1)$^+$.

Example 146

(6-bromoimidazo[1,2-a]pyridin-3-yl)methylene)-N-(2-fluoro-5-methylphenyl)-1-methylhydrazinecarboxamide The title compound was prepared according to the procedure as set forth in example 145, except that 1-fluoro-2-isocyanato-4-methylbenzene was used in place of benzyl isocyanate to yield 19.55% of the title compound. $^1$HNMR (DMSO-d$_6$; 500 MHz): δ 9.35 (s, 1H), 8.95 (s, 1H), 8.28 (s, 1H), 8.16 (s, 1H), 7.78-7.79 (d, 1H, J=7 Hz), 7.71-7.73 (d, 1H, J=9.5 Hz), 7.55-7.58 (dd, 1H, J=9.5 Hz, 1.5 Hz), 7.14-7.18 (m, 1H), 6.93-6.94 (m, 1H), 3.42 (s, 3H), 2.30 (s, 3H); MS: m/z 404(M+1)$^+$.

Example 147

(6-bromoimidazo[1,2-a]pyridin-3-yl)methylene)-N-(5-fluoro-2-methylphenyl)-1-methylhydrazinecarboxamide The title compound was prepared according to the procedure as set forth in example 145, except that 4-fluoro-2-isocyanato-1-methylbenzene was used in place of benzyl isocyanate to yield 33.52% of the title compound. $^1$H NMR (DMSO-d$_6$; 500 MHz): δ 9.36 (s, 1H), 8.86 (s, 1H), 8.27 (s, 1H), 8.14 (s, 1H), 7.67-7.79 (m, 2H), 7.51-7.55 (dd, 1H, J=9.6 Hz, 1.8 Hz), 7.21-7.26 (t, 1H, J=7.8 Hz), 6.81-6.87 (m, 1H), 3.41 (s, 3H), 2.30 (s, 3H); MS: m/z 404 (M+1)$^+$.

Example 148

(E)-1-methyl-N-(2-morpholinoethyl)-2-((6-(pyridin-3-yl)imidazo[1,2-a]pyridin-3-yl)methylene)hydrazinecarbothioamide Methyl hydrazine (41.25 mg, 0.8968 mmoles) was added to ethanolic solution of 6-(pyridin-3-yl)imidazo[1,2-a]pyridine-3-carbaldehyde (100 mg, 0.4484 mmoles) at RT. The reaction mixture was heated at 85° C. for 1.5 hours. The solvent was then evaporated. The residue was dissolved in ethanol (5 ml), followed by addition of 4-(2-isothiocyanatoethyl) morpholine (114.83 mg, 0.6726 mmoles). The reaction mixture was refluxed for 2 hours, then the solvent was evaporated. Water was poured into the residue and the aqueous solution was extracted with chloroform. Organic layer was separated, washed with water and brine and dried over sodium sulfate. The crude product was purified by column chromatography (100-200 mesh size silica gel, 1.5% MeOH in CHCl$_3$). Yield: 21%; $^1$HNMR (CDCl$_3$; 300 MHz): δ 9.39 (s, 1H), 8.91 (s, 1H), 8.71 (s, 1H), 8.11 (m, 3H), 7.93 (m, 1H), 7.67 (d, 1H, J=9 Hz), 7.48 (s, 1H), 4.01 (s, 3H), 3.76 (s, 2H), 3.33 (s, 2H), 2.47 (s, 2H), 2.06 (s, 4H); MS: m/z 424(M+1)$^+$.

Example 149

(E)-N-(4-cyanophenyl)-1-methyl-2-((6-(pyridin-3-yl)imidazo[1,2-a]pyridin-3-yl)methylene)hydrazinecarbothioamide The title compound was prepared according to the procedure as set forth in example 148, except that 4-isothiocyanatobenzonitrile was used in place of 4-(2-isothiocyanatoethyl) morpholine to yield 25% of the title compound. $^1$HNMR (CDCl$_3$; 300 MHz): δ 9.77 (s, 1H), 9.29 (s, 1H), 8.87 (s, 1H), 8.17 (s, 1H), 8.20 (d, 2H, J=19.5 Hz), 7.96 (m, 2H), 7.83 (m, 5H), 4.07 (s, 3H); MS: m/z 412 (M+1)$^+$.

Example 150

(E)-N-(4-methoxyphenyl)-1-methyl-2-((6-(pyridin-3-yl)imidazo[1,2-a]pyridin-3-yl)methylene)hydrazinecarbothioamide The title compound was prepared according to the procedure as set forth in example 148, except that 1-isothiocyanato-4-methoxybenzene was used in place of 4-(2-isothiocyanatoethyl)morpholine to yield 25% of the title compound. $^1$HNMR (CDCl$_3$; 300 MHz): δ 9.38 (s, 1H), 8.87 (s, 1H), 8.62 (s, 1H), 8.16 (d, 2H, J=20.7 Hz), 7.92 (d, 1H, J=9.3 Hz), 7.76 (m, 2H), 7.37 (d, 2H, J=8.1 Hz), 7.11 (s, 1H), 6.92 (d, 2H, J=7.8 Hz), 4.07 (s, 3H), 3.86 (s, 3H); MS: m/z 417(M+1)$^+$.

Example 151

2-((6-bromoimidazo[1,2-a]pyridin-3-yl)methylene)-1-methyl-N-(2-morpholinoethyl) hydrazinecarbothioamide The title compound was prepared according to the procedure as set forth in example 148, except that 4-(2-isothiocyanatoethyl)morpholine was used in place of benzyl isocyanate and 6-bromoimidazo[1,2-a]pyridine-3-carbaldehyde was used in place of 6-(pyridin-3-yl)imidazo[1,2-a]pyridine-3-carbaldehyde to yield 27% of the title compound. $^1$HNMR (DMSO-d$_6$; 300 MHz): δ 9.36 (s, 1H), 8.74 (s, 1H), 8.36 (s, 1 Hz), 8.21 (s, 1H), 7.70-7.73 (d, 1H, J=9 Hz), 7.55-7.58 (d, 1H, J=9 Hz), 3.84 (s, 3H), 3.70-3.71 (m, 2H), 3.55 (s, 4H), 2.60 (s, 2H), 2.45 (s, 4H); MS: m/z 425(M+1)$^+$.

Example 152

2-((6-bromoimidazo[1,2-a]pyridin-3-yl)methylene)-1-methyl-N-(4-(trifluoromethyl)phenyl) hydrazinecarbothioamide The title compound was prepared according to the procedure as set forth in example 148, except that 1-isothiocyanato-4-(trifluoromethyl)benzene was used in place of benzyl isocyanate and 6-bromoimidazo[1,2-a]pyridine-3-carbaldehyde was used in place of 6-(pyridin-3-yl)imidazo[1,2-a]pyridine-3-carbaldehyde to yield 35% of the title compound.

Yield: 35%; $^1$H NMR (DMSO-d$_6$; 300 MHz): δ 10.58 (s, 1H), 9.48 (s, 1H), 8.51 (s, 1H), 8.33 (s, 1H), 7.93-7.96 (d, 2H, J=7.8 Hz), 7.73-7.76 (m, 3H), 7.58-7.61 (d, 1H, J=9 Hz), 3.94 (s, 3H); MS: m/z 457(M+2)$^+$.

Pharmacology

The efficacy of the present compounds can be determined by a number of pharmacological assays well known in the art, such as described below. The exemplified pharmacological assays, which follow herein below, have been carried out with the compounds of the present invention.

Example 153

Protocol for kinase assay (PI3Kα)

The assay was designed as in the reference, Cell, 2006, 125, 733-47 (Supplemental Data), the disclosure of which is incorporated by reference for the teaching of the assay.

The kinase reaction was carried out in a 25 μL volume in a 1.5 mL microcentrifuge tube. The reaction mixture consisted of kinase buffer (10 mM Hepes, pH 7.5, 50 mM MgCl$_2$), 20 ng PI3Kα kinase (Millipore, USA), 12.5 μg phosphotidylinositol (PI), 10 μM ATP and 1 μCi $^{32}$γ P dATP. Representative compounds of present invention were added at concentrations (stock solution was prepared in DMSO and subsequent dilutions were made in kinase buffer) as mentioned in the table 1. The reactions were incubated at 30° C. for 20 minutes and were terminated by adding 1:1 mixture of MeOH and CHCl$_3$. The tube contents were mixed on a vortex mixer and centrifuged at 10000 rpm for 2 minutes. 10 µL of the organic (lower) phase was spotted on to a TLC plate (silica, mobile phase: n-propanol and 2 M glacial acetic acid in 65:35 ratio). The plates were dried and exposed to an X-ray film. The bands appearing as a result of $^{32}\gamma$ P incorporation in PI were quantitated using the Quantityl)ne (BioRad, USA) densitometry program. PI-103 (Calbiochem, USA) was used as a standard.

Results: Table 1 depicts the $IC_{50}$ values (µM) of the representative compounds of present invention for PI3K inhibition.

TABLE 1

| Example No. | $IC_{50}$ (µM) | Example No. | $IC_{50}$ (µM) |
|---|---|---|---|
| 5 | + | 6 | + |
| 7 | ++ | 11 | ++ |
| 14 | ++ | 15 | + |
| 16 | + | 17 | ++ |
| 18 | ++ | 20 | ++ |
| 21 | ++ | 22 | ++ |
| 23 | ++ | 25 | ++ |
| 26 | ++ | 27 | ++ |
| 84 | ++ | 100 | ++ |
| 115 | ++ | Standard PI-103 | 80% inhibition at 100 nM |

$IC_{50}$ Ranges
+ $1 \geq IC_{50} > 0.5$
++ $0.5 \geq IC_{50} > 0.01$

Example 154 mTOR Activity Assay

The assay was designed as in the reference, Biochemical Journal, 2000, 350, 717-722, the disclosure of which is incorporated by reference for the teaching of the assay.

Seed cells (Ovarian cell line A2780, ATCC) were plated in a 96 well microtitre plate at a density of 50,000 cells/cm² in appropriate complete cell culture medium. The cells were allowed to adhere for 18-24 hours. The cells were allowed to starve for 24 hours. The cells were pretreated (in triplicates) with the representative compounds of the present invention (refer table 2a and 2b) (stock solution was prepared in DMSO and subsequent dilutions were made in kinase buffer) at a concentration of 10 µM for one hour. Then the cells were stimulated with 20% FCS for 30 minutes. A typical assay would consist of a set of unstimulated cells, a set of stimulated cells and a set of cells treated with compounds of present invention and a set of cells treated with the stimulator. The medium was discarded. The cells were fixed with 100 µL of 3.7% formaldehyde for 15 minutes. The formaldehyde was discarded by inverting the plate and tapping it on a thick tissue paper layer to remove traces. The cells were washed and permeabilized with 200 µL PBS+Triton-X 100 solution (hereafter referred to as PBS-Triton, containing 0.1% triton-X 100 in 1×PBS) three times, incubating the cells each time for 5 minutes. 100 µL blocking solution (10% FCS in PBS-Triton) was added and incubated for 1 hour at 25° C. The blocking solution was discarded and cells were incubated with the primary antibody in PBS-Triton at a dilution of 1:500 for 1 hour at RT (25° C.). [The primary antibody is Phospho-AKT (Ser 473); Cell Signaling; Cat. No. 9271]. The primary antibody solution was discarded and the cells were washed 3 times with PBS-Triton solution and incubated with the HRP-conjugated secondary antibody in PBS-Triton at a dilution of 1:500 for 1 hour at RT (25° C.). The cells were washed 3 times with PBS-Triton followed by two washes with PBS (to remove traces of triton-X 100). The OPD (o-phenylene diamine dihydrochloride) substrate was prepared for detection of the signal by dissolving one tablet set (two tablets) of SigmaFast OPD (Sigma, Cat No. P9187) in 20 mL distilled water. It should be protected from light. 100 µL OPD solutions was added to the wells and the plate was incubated in the dark for 3-5 minutes (depending upon the development of the color). The reaction was stopped by adding 50 µL 2 N $H_2SO_4$. The absorbance was measured at 490 nm. The values were expressed in the treated samples, in terms of percentage or fold decrease in AKT phosphorylation with respect to the induced sample. PI-103 (Calbiochem, USA) was used as a standard.

Results: % inhibition of mTOR at 1 µM and 10 µM is indicated in Table 2a.

$IC_{50}$ values of representative compounds for mTOR activity assay are indicated in Table 2b TABLE 2a

| Example No. | % Inhibition of mTOR activity at 1 µM | Example No. | % Inhibition of mTOR activity at 1 µM |
|---|---|---|---|
| 6 | + | 7 | + |
| 8 | + | 11 | + |
| 15 | + | 16 | + |
| 17 | + | 20 | + |
| 23 | + | 84 | + |
| Standard (PI-103) | 50 | | |
| % Inhibition of mTOR activity at 10 µM | | | |
| 26 | ++ | | |

% Inhibition Ranges
+ 50% ≥ % Inhibition ≥ 30%
++ % Inhibition > 50%

TABLE 2b

| Example No. | mTOR $IC_{50}$ (µM) | Example No. | mTOR $IC_{50}$ (µM) |
|---|---|---|---|
| 5 | ++ | 21 | ++ |
| 25 | ++ | 115 | + |
| Standard (PI-103) | 50% inhibition at 1 µM | | |

$IC_{50}$ Ranges in µM
+ $10 \geq IC_{50} > 5$
++ $5 \geq IC_{50} \geq 1$

Example 155

Cytotoxicity Assay

Propidium Iodide Assay
The assay was designed as in the reference, Anticancer Drugs, 2002, 13, 1-8, the disclosure of which is incorporated by reference for the teaching of the assay.

Cells from cell lines as mentioned in the table given below were seeded at a density of 3000 cells/well in a white opaque 96-well plate. Following incubation at 37° C./5% $CO_2$ for a period of 18-24 hours, the cells were treated with various concentrations (stock solution was prepared in DMSO and subsequent dilutions were made in media as per ATCC guidelines) of the representative compounds of present invention (refer table 3) for a period of 48 hours. At the end of treatment, the spent culture medium was discarded, the cells were washed with 1×PBS and 200 µl of 7 µg/ml propidium iodide was added to each well. The plates were frozen at −70° C. for at least 24 hours. For analysis, the plates were brought to RT, allowed to thaw and were read in PolarStar fluorimeter with the fluorescence setting. The percentage of viable cells in the non treated set of wells was considered to be 100 and the percentage viability following treatment was calculated accordingly. $IC_{50}$ values were calculated from graphs plotted using these percentages. Results for representative compounds of present invention in individual cell lines are shown in Table 3 and 4.

The abbreviations for the Cell Lines as used in Table 3 are:

| Type of Cancer | Abbreviation | Cell Line | Abbreviation |
|---|---|---|---|
| Lung | C1 | A549 | C1a |
| | | H460 | C1b |
| Prostate | C2 | PC3 | C2a |
| Ovarian | C3 | A2780 | C3a |
| | | SKOV3 | C3b |
| | | OVCAR 3 | C3c |
| Colon | C4 | HT29 | C4a |
| | | HCT116 | C4b |
| Pancreatic | C5 | PANC 1 | C5a |
| | | CAPAN1 | C5b |
| Breast | C6 | MDA MB 231 | C6a |
| | | MDA MB 468 | C6b |
| | | MCF7 | C6c |
| | | BT 549 | C6d |
| | | T47D | C6e |
| Multiple Myeloma | C7 | U266B1 | C7a |
| | | RPMI 8226 | C7b |
| Glioblastoma | C8 | U 373 | C8a |
| | | U 87 MG | C8b |
| Human melanoma | C9 | G361 | C9 |
| Cervical | C10 | HeLA S3 | C10 |
| Hypopharyngeal | C11 | FaDu | C11 |

TABLE 3

| Cell Lines | | Example No. | | | | | | | | |
|---|---|---|---|---|---|---|---|---|---|---|
| | | 1 | 2 | 3 | 5 | 6 | 7 | 9 | 10 | 11 |
| C1 | C1a | ++ | ++ | ++ | ++ | ++ | + | ++ | ++ | + |
| | C1b | ++ | ++ | ++ | -- | -- | + | ++ | ++ | + |
| C2 | C2a | ++ | ++ | ++ | -- | -- | + | ++ | ++ | + |
| C3 | C3a | ++ | ++ | ++ | ++ | ++ | -- | ++ | ++ | + |
| | C3b | -- | -- | -- | ++ | -- | -- | -- | -- | -- |
| | C3c | ++ | -- | ++ | ++ | ++ | -- | -- | ++ | -- |
| C4 | C4a | -- | + | -- | -- | -- | -- | -- | -- | -- |
| | C4b | ++ | -- | ++ | ++ | ++ | -- | -- | ++ | -- |
| C5 | C5a | ++ | -- | -- | ++ | ++ | -- | -- | -- | -- |
| | C5b | ++ | -- | -- | ++ | ++ | -- | -- | -- | -- |
| C6 | C6a | -- | ++ | -- | -- | -- | -- | -- | -- | -- |
| | C6b | -- | -- | -- | -- | -- | + | ++ | -- | + |
| | C6c | -- | -- | -- | -- | -- | + | -- | -- | -- |
| | C6d | -- | -- | -- | -- | -- | -- | ++ | -- | + |
| | C6e | -- | -- | -- | + | + | -- | -- | -- | -- |
| C9 | C9a | -- | -- | -- | -- | -- | + | -- | -- | -- |
| C11 | C11a | -- | -- | -- | ++ | ++ | -- | -- | -- | -- |

| Cell Lines | | Example No. | | | | | | | | |
|---|---|---|---|---|---|---|---|---|---|---|
| | | 12 | 18 | 20 | 21 | 23 | 24 | 25 | 26 | 27 |
| C1 | C1a | ++ | + | + | ++ | ++ | ++ | ++ | ++ | + |
| | C1b | ++ | + | + | ++ | ++ | ++ | ++ | ++ | + |
| C2 | C2a | ++ | + | + | ++ | -- | ++ | ++ | -- | + |
| C3 | C3a | ++ | -- | + | ++ | ++ | ++ | ++ | ++ | -- |
| | C3b | -- | -- | -- | ++ | -- | -- | ++ | -- | -- |
| | C3c | ++ | -- | -- | ++ | -- | -- | ++ | ++ | -- |
| C4 | C4a | -- | -- | -- | -- | -- | -- | -- | -- | -- |
| | C4b | ++ | -- | + | ++ | -- | + | ++ | -- | -- |
| C5 | C5a | -- | -- | -- | ++ | -- | -- | ++ | ++ | -- |
| | C5b | -- | -- | -- | ++ | -- | -- | ++ | ++ | -- |
| C6 | C6a | -- | -- | -- | ++ | -- | -- | ++ | -- | -- |
| | C6b | -- | + | -- | ++ | -- | -- | -- | -- | + |

TABLE 3-continued

| | | | | | | | | | |
|---|---|---|---|---|---|---|---|---|---|
| | C6c | -- | + | -- | ++ | -- | -- | ++ | -- | + |
| | C6d | -- | -- | -- | ++ | -- | -- | ++ | -- | -- |
| | C6e | -- | -- | -- | -- | -- | -- | ++ | -- | -- |
| C7 | C7a | -- | -- | -- | ++ | -- | -- | -- | -- | -- |
| | C7b | -- | -- | -- | ++ | -- | -- | -- | -- | -- |
| C8 | C8a | -- | -- | + | ++ | -- | ++ | -- | -- | -- |
| | C8b | -- | -- | + | ++ | -- | ++ | -- | -- | -- |
| C9 | C9a | -- | + | -- | ++ | -- | -- | -- | -- | + |

| Cell Lines | | Example No. | | | | | | | |
|---|---|---|---|---|---|---|---|---|---|
| | | 28 | 29 | 30 | 31 | 45 | 53 | 54 | 65 |
| C1 | C1a | + | ++ | + | ++ | ++ | ++ | ++ | ++ |
| | C1b | + | ++ | + | ++ | ++ | ++ | ++ | ++ |
| C2 | C2a | + | ++ | + | ++ | -- | -- | -- | -- |
| C3 | C3a | + | ++ | -- | ++ | -- | -- | -- | -- |
| | C3b | -- | -- | -- | -- | -- | -- | -- | -- |
| | C3c | -- | ++ | -- | -- | -- | -- | -- | -- |
| C4 | C4a | + | -- | -- | + | -- | -- | -- | -- |
| | C4b | -- | ++ | -- | -- | -- | -- | -- | -- |
| C5 | C5a | -- | -- | -- | -- | -- | -- | -- | -- |
| | C5b | -- | -- | -- | -- | -- | -- | -- | -- |
| C6 | C6a | + | -- | -- | ++ | -- | -- | -- | -- |
| | C6b | -- | -- | -- | -- | -- | -- | -- | -- |
| | C6c | -- | -- | + | -- | -- | -- | -- | -- |
| C9 | C9a | -- | -- | + | -- | -- | -- | -- | -- |

| Cell Lines | | Example No. | | | | | |
|---|---|---|---|---|---|---|---|
| | | 83 | 85 | 88 | 99 | 100 | 132 |
| C1 | C1a | + | ++ | ++ | ++ | ++ | ++ |
| | C1b | + | ++ | ++ | ++ | ++ | ++ |
| C2 | C2a | + | ++ | -- | ++ | -- | -- |
| C3 | C3a | ++ | ++ | -- | ++ | ++ | -- |
| | C3b | -- | -- | -- | -- | -- | -- |
| | C3c | -- | -- | -- | ++ | -- | -- |
| C4 | C4a | + | + | -- | -- | -- | -- |
| | C4b | -- | -- | -- | ++ | -- | -- |
| C5 | C5a | -- | -- | -- | -- | -- | -- |
| | C5b | -- | -- | -- | -- | -- | -- |
| C6 | C6a | ++ | ++ | -- | -- | -- | -- |
| | C6b | -- | -- | -- | -- | -- | -- |
| | C6c | -- | -- | -- | -- | -- | -- |
| C9 | C9a | -- | -- | -- | -- | -- | -- |

$IC_{50}$ Ranges in μM
+ $IC_{50} > 5$
++ $5 \geq IC_{50} \geq 0.01$
-- Not Done

TABLE 4

% inhibition at 1 μM

| Cell Lines | | Example No. | | | | | | | |
|---|---|---|---|---|---|---|---|---|---|
| | | 91 | 142 | 143 | 144 | 146 | 149 | 150 | 152 |
| C2 | C2a | ++ | + | + | + | ++ | + | + | + |
| C3 | C3a | ++ | + | + | + | ++ | + | + | + |

% Inhibition Ranges
+ 50% ≥ % Inhibition ≥ 30%
++ % Inhibition > 50%

Example 156

STAT3 Bioassay

Hela STAT3 Assay

Cells were seeded (Hela Stat3-luc, ATCC P/N 30-2002) in a white 96 well plate (Nunc cat.no.136101) at a density of 20,000cells/well in 179 μl volume per well (DMEM from Sigma containing 10% FCS). The plate was incubated for 24 hours at 37° C./5% $CO_2$. The cells (wells in triplicates) were then treated with 1 μl/well of 200× stock of the desired compound concentration prepared in 100% DMSO. Curcumin was used as a standard or positive control, added 10 μg/ml in triplicate. DMSO was used as medium control (1 μl/well added in triplicates). The plate was incubated at 37° C./5% $CO_2$ for 1 hour. 20 μl/well Oncostatin M (Oncostatin M, Human, Recombinant, *E. coli*, Cat.No. 496260, 10 μg from Calbiochem) was added to treated wells, induction control (in triplicate) (1000 ng/ml stock prepared in serum free medium to get final concentration 100 ng/ml). The plate was then incubated for 7-8 hours at 37° C./5% $CO_2$ for induction. A typical assay would consist of triplicate of medium control, triplicate of induction control, triplicate of positive/standard control and test compounds at desired concentration in triplicates. For termination Luciferase assay protocol was followed where the culture medium was removed from all the wells.

Luciferase Assay

200 μl well of PBS was added to remove traces of medium and compound. The PBS was discarded. 40 μl/well of 1× lysis buffer was added to all the wells. The plate was incubated at RT for 20 minutes with intermittent shaking. 100 μl/well of LAB reagent was added to all the wells in dark. {LAB reagent for 1 plate=8 ml Luciferase assay buffer (LAB)+1 ml Coenzyme A (Sigma cat no. C3019) (2.1 mg/ml stock in LAB)+ 530 μL of ATP (Sigma cat.no.A2383) (5.85 mg/ml stock in LAB)+1 ml luciferin reagent (Promega cat no.245355) (2 mg/ml stock in LAB, protect from light)}.

The luminescence was immediately read on polar star. The values were expressed as percentage inhibition, in terms of treated values to that STAT3 (induction control). $IC_{50}$ values were calculated from graphs using these percentages. Results for representative compounds of present invention are shown in Table 5.

1× Lysis Buffer

| Final concentration | Stock | Quantity for 100 ml |
|---|---|---|
| 125 mM Tris phosphate buffer pH 7.8 | 0.2M | 12.5 ml |
| 10 mM DTT | 0.2M | 155 mg |
| 50% glycerol | 100% | 10 ml |
| 5% Triton X-100 | 100% | 1 ml |
| Distilled water | | To make volume 100 ml |

1M Tris Phosphate Buffer:

Dissolve 12.114 gm tris(hydroxymethyl)aminomethane (Trizma, Sigma Aldrich) in 70 ml distilled water and adjust pH to 7.8 using ortho-phosphoric acid and then make up the volume 100 ml with distilled water.

Luciferase Assay Buffer

| Final concentration | |
|---|---|
| 20 mM Tricine (pH 7.8) | 1000 ml |
| 1.07 mM Mg•ALBA | 3.58 gm |
| 2.67 mM $MgSO_4$ | 520 mg |
| 0.1 mM EDTA | 657 mg |
| 33.3 mM DTT | 37 mg |
| | 5.1 gm |

TABLE 5

Results for STAT3 activity

| Example No. | $IC_{50}$ (μM) | Example No. | $IC_{50}$ (μM) |
|---|---|---|---|
| 1 | ++ | 2 | ++ |
| 4 | +++ | 5 | +++ |
| 6 | ++ | 8 | +++ |
| 9 | ++ | 10 | +++ |
| 13 | ++ | 14 | ++ |
| 15 | +++ | 16 | ++ |
| 20 | +++ | 21 | ++ |
| 22 | +++ | 24 | + |
| 25 | +++ | 26 | +++ |
| 28 | + | 115 | ++ |

$IC_{50}$ Ranges in μM
+ $IC_{50}$ > 10
++ 10 ≥ $IC_{50}$ > 5
+++ 5 ≥ $IC_{50}$ ≥ 0.1

Example 157

In Vitro Screening to Identify Inhibitors of IL-6 and TNF-α

Human Monocyte Assay

The assay was designed as in the reference, Physiol. Res., 2003, 52, 593-598, the disclosure of which is incorporated by reference for the teaching of the assay.

Peripheral blood mononuclear cells (hPBMC) were harvested from human blood and suspended in RPMI 1640 culture medium containing 10% FCS, 100 U/mL penicillin and 100 mg/mL streptomycin (assay medium). Monocytes in the hPBMCs were counted using a Coulter Counter following which the cells were resuspended at $2 \times 10^5$ monocytes/mL. A cell suspension containing $2 \times 10^4$ monocytes was aliquoted per well of a 96-well plate. Subsequently, the hPBMCs were incubated for 4-5 hours at 37° C., 5% $CO_2$ (During the incubation, the monocytes adhered to the bottom of 96-well plastic culture plate). Following the incubation, the non-adherent lymphocytes were washed with assay medium and the adherent monocytes re-fed with assay medium. After a 48-hour incubation period (37° C., 5% $CO_2$), monocytes were pretreated with various concentrations of representative compounds of present invention (refer to table 6 and 7) (prepared in DMSO) or vehicle (0.5% DMSO) for 30 minutes and stimulated with 1 μg/ml LPS (*Escherchia coli* 0111:B4, Sigma Chemical Co., St. Louis, Mo.). The incubation was continued for 5 hours at 37° C., 5% $CO_2$. Supernatants were harvested, assayed for IL-6 and TNF-α by ELISA as described by the manufacturer (BD Biosciences, USA). Dexamethasone (10 μM) was used as standard for this assay. The 50% inhibitory concentration ($IC_{50}$) values were calculated by a nonlinear regression method. Biological results for both IL-6 and TNFα are indicated in Table 6 and Table 7 respectively.

TABLE 6

| Example No. | IL-6 ($IC_{50}$ μM) |
|---|---|
| 1 | ++ |
| 2 | ++ |
| 3 | + |
| 4 | ++ |
| 5 | ++ |
| 6 | ++ |
| 9 | ++ |
| 10 | ++ |

TABLE 6-continued

| Example No. | IL-6 (IC$_{50}$ μM) |
|---|---|
| 11 | + |
| 13 | ++ |
| 14 | ++ |
| 16 | ++ |
| 17 | ++ |
| 19 | ++ |
| 21 | ++ |
| 22 | + |
| 23 | ++ |
| 25 | ++ |
| 26 | ++ |
| 28 | ++ |
| 30 | + |
| 34 | ++ |
| 35 | ++ |
| 36 | + |
| 39 | ++ |
| 40 | ++ |
| 41 | ++ |
| 42 | + |
| 43 | + |
| 44 | ++ |
| 45 | ++ |
| 46 | + |
| 47 | + |
| 50 | ++ |
| 51 | ++ |
| 52 | ++ |
| 53 | ++ |
| 54 | ++ |
| 55 | ++ |
| 56 | ++ |
| 57 | ++ |
| 58 | ++ |
| 59 | ++ |
| 60 | ++ |
| 61 | ++ |
| 62 | ++ |
| 63 | ++ |
| 64 | ++ |
| 65 | ++ |
| 66 | ++ |
| 67 | ++ |
| 68 | ++ |
| 69 | ++ |
| 70 | ++ |
| 72 | + |
| 73 | + |
| 74 | ++ |
| 84 | ++ |
| 87 | ++ |
| 88 | ++ |
| 99 | ++ |
| 101 | ++ |
| 104 | + |
| 105 | ++ |
| 106 | + |
| 107 | ++ |
| 109 | + |
| 110 | + |
| 112 | + |
| 113 | ++ |
| 114 | + |
| 115 | + |
| 117 | + |
| 118 | + |
| 127 | + |
| 128 | ++ |
| 129 | + |
| 130 | ++ |
| 131 | + |
| 134 | ++ |
| 135 | ++ |
| 137 | + |
| 138 | + |
| 139 | + |
| 141 | ++ |
| 142 | + |
| 143 | ++ |
| 144 | + |
| 145 | ++ |
| 146 | + |
| 148 | + |
| 149 | + |
| 150 | + |
| 151 | ++ |
| 152 | ++ |

IC$_{50}$ Ranges in μM
+ IC$_{50}$ ≥ 5
++ 5 > IC$_{50}$ ≥ 0.001

TABLE 7

| Example No. | TNF-α | Example No. | TNF-α |
|---|---|---|---|
| 1 | ++ | 4 | ++ |
| 5 | + | 6 | ++ |
| 10 | ++ | 13 | ++ |
| 14 | ++ | 16 | ++ |
| 19 | ++ | 21 | ++ |
| 45 | ++ | 105 | ++ |

IC$_{50}$ Ranges in μM
+ 15 ≥ IC$_{50}$ > 1
++ 1 ≥ IC$_{50}$ > 0.001

Example 158

Inhibition of Production of Cytokines

Synovial Tissue Assay

The assay was designed as in the reference, Lancet, 2(8657), 244-7, Jul. 29 (1989), the disclosure of which is incorporated by reference for the teaching of the assay.

Stock Solution: Compounds of the present invention were dissolved in DMSO to obtain a stock solution of 20 mM.

Synovial tissue was obtained from rheumatoid arthritis patients undergoing knee replacement surgery. The tissue was minced into small pieces and digested in RPMI medium containing 100 U/ml penicillin-G, 100 μg/ml streptomycin, 50 ng/ml amphotericin B (GIBCO; USA), 1.33 mg/ml collagenase Type I (Worthington Biochemical Corporation, New Jersey), 0.5 μg/ml DNAse Type I (Sigma Aldrich; St. Louis, Mo.) and 8.33 U/ml heparin (Biological E. Limited, India) for 3 hours at 37° C., 5% CO$_2$. The digested tissue was filtered through a membrane (mesh size 70 micron; Sigma Aldrich). Subsequently, the cells were washed 3 times and resuspended in complete medium (RPMI supplemented with 5% FBS and 5% human serum-AB+) at a concentration of 1×10$^6$ cells/ml. All cell washes in this assay were performed using Rosewall Park Memorial Institute (RPMI)-1640 medium (JRH; Australia). For the experiment, 100 μl of cell suspension was added to the wells of a 96-well culture plate. Following cell plating, 100 μl of the culture medium and 1 μl of various concentrations (0.01, 0.03, 0.1, 0.3, 1, 3, 10, 30 and 100 μM) of the compounds of present invention dissolved in DMSO were added to the cells. The final concentration of DMSO was adjusted to 0.5%. For experimental purposes, 1 μl of 20× concentrated solution of the compounds of present invention were dissolved in 200 μl cell suspension to achieve a final concentration of 0.01, 0.03, 0.1, 0.3, 1, 3, 10, 30 and 100 μM. The vehicle (0.5% DMSO) was used as control. 10 μM dexamethasone (Sigma Aldrich) or 1 μM 7-hydroxyfluorinide (7HF) were used as standards for the experiments. The plates were incubated for 16 hours at 37° C., 5% $CO_2$. Subsequently, the supernatants were harvested and stored at −70° C. The amounts of TNF-α, IL-6 and interleukin-8 (IL-8) in the supernatants were assayed using OptiEIA ELISA sets, (BD BioSciences Pharmingen). The protocol followed was as per manufacturers instructions. The 50% inhibitory concentration ($IC_{50}$) values were calculated by a nonlinear regression method using the GraphPad software (Prism 3.03). The cytotoxicity of test compounds in synovial cells was assessed by MTS assay. Absorbance was measured at 490 nm. Percent cytotoxicity was calculated by the equation:

$$\% \text{ Cytotoxicity} = (A-B)/A \times 100$$

where, A is the absorbance of cells treated with DMSO alone and B is the absorbance of cells treated with the test article.
Results: Compounds of the present invention inhibited the spontaneous production of IL-6 and/or TNF-α and/or IL-β and/or IL-8 from freshly isolated synovial tissue cells from rheumatoid arthritis patients. The $IC_{50}$ of IL-6, TNF-α and IL-8 inhibition are provided in the Table 8.

TABLE 8

| Example No. | Synovial tissue ($IC_{50}$ μM) | | |
|---|---|---|---|
| | IL-6 | TNF-α | IL-8 |
| 4 | ++ | ++ | + |
| 5 | ++ | ++ | + |
| 6 | + | ++ | + |
| 9 | ++ | ++ | + |
| 13 | ++ | ++ | + |
| 14 | ++ | ++ | + |
| 16 | ++ | ++ | + |
| 19 | + | + | + |
| 21 | ++ | ++ | ++ |
| 25 | ++ | ++ | + |

$IC_{50}$ Ranges in μM
+ 3 ≥ $IC_{50}$ > 0.3
++ 0.3 ≥ $IC_{50}$ > 0.01

In-Vivo Studies

All experiments were carried out in accordance with the guidelines of the Committee for the Purpose of Control and Supervision of Experiments on Animals (CPCSEA), Tamil Nadu, India. Procedures using laboratory animals were approved by the Institutional Animal Ethics Committee (IAEC) of Piramal Life Sciences Limited, Mumbai, India.

Example 159

Ulcerative Colitis

The efficacy of compounds of the present invention on the gross pathology of colitis and proinflammatory mediators was determined by following the method described in *Am. J. Physiol. Gastrointest. Liver Physiol.* 295 (6): G1237-45 (2008), the disclosure of which is incorporated by reference for the teaching of the assay.
Induction of Colitis C57BL/6J mice (6 weeks of age, weighing 18-22 gms) were obtained from Jackson Laboratories (Bar Harbor, Me.) and housed in individually ventilated cage (IVC) system. Colitis was induced in mice by replacing drinking water with 3% (w/v) DSS (molecular weight 35-50 kDa, ICN Biomedicals, Aurora, Ohio, US) in water. This solution was made available to the experimental animals ad libitum, from day 0 to day 10. A batch of six naïve animals received water instead of DSS during this period.

DSS-induction of colitis was manifested with increase in clinical disease activity index associated with weight loss and presence of blood in feces.
Treatment The animals were weighed every day and the record of body weights was maintained. The compound of Example 25 (10 mg/kg, prepared at a concentration of 1 mg/mL in 0.5% (w/v) CMC after mixing a drop of Tween 20) was administered orally daily to the colitis induced animals. This treatment was initiated on day 6 and continued up to day 10. During this period, DSS control animals received DSS, positive control animals received 5-aminosalicylic acid (5-ASA, 25 mg/kg, p.o.) and naïve animals received 0.5% CMC once daily.
Evaluation:

At the end of DSS treatment period, mice were humanely euthanized with 15% urethane (i.p.). The whole colon (i.e., including ceacum, proximal colon and distal colon) was excised.

The colon was macrosopically assessed by determining
a) Rectal bleeding/blood in faeces
b) Stool consistency
c) Blood in colon
d) Colon length
e) % weight loss
f) Blood hemoglobin concentration Disease Activity Index: various features were scored as delineated in the following table.

Disease activity index is the sum of scores of all features.

| Feature scored | Score | Description |
|---|---|---|
| % Weight loss | 0 | No change/increase |
| | 1 | 0-5% Reduction |
| | 2 | 5-10% Reduction |
| | 3 | 10-15% Reduction |
| | 4 | 10-20% Reduction |
| Rectal Bleeding | 0 | Absent |
| | 1 | Slightly present |
| | 2 | Heavy |
| Stool Consistency | 0 | Normal |
| | 1 | Slightly loose |
| | 2 | Loose |
| | 3 | Diarrhoea |
| Blood in Colon | 0 | Absent |
| | 1 | Slightly present |
| | 2 | Markedly present |

Figure 2:
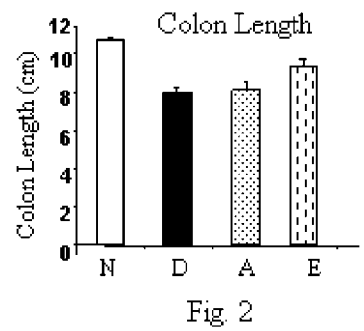
FIG. 2 is a graph depicting effect of compound of Example 25 on DSS induced shortening of colon in C57BL/6J mice. 5-ASA was used as positive control
Figure 3:
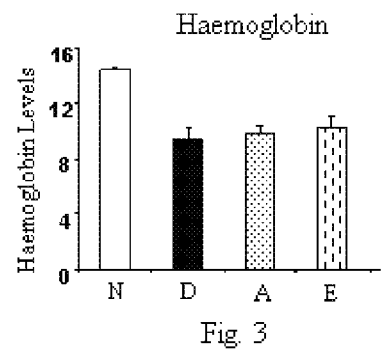
FIG. 3 is a graph depicting effect of compound of Example 25 on DSS induced decrease in haematocrit in C57BL/6J mice. 5-ASA was used as positive control
Figure 4:
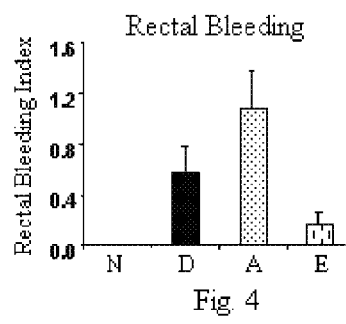
FIG. 4 is a graph depicting effect of compound of Example 25 on DSS induced rectal bleeding in C57BL/6J mice. 5-ASA was used as positive control
Figure 5:
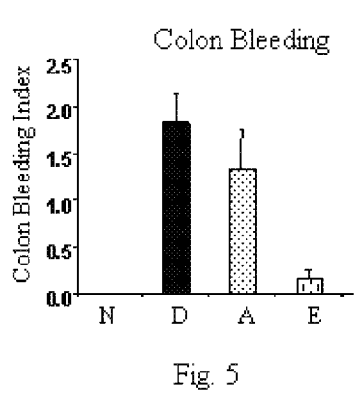
FIG. 5 is a graph depicting effect of compound of Example 25 on DSS induced colon bleeding in C57BL/6J mice. 5-ASA was used as positive control
Figure 6:
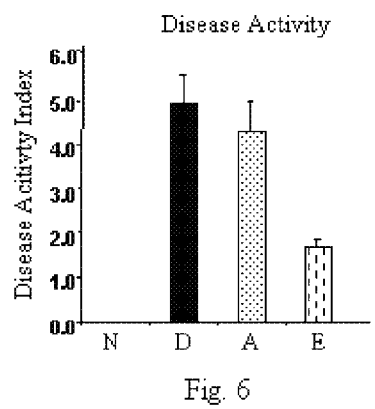
FIG. 6 is a graph depicting effect of compound of Example 25 on DSS induced disease activity index in C57BL/6J mice. 5-ASA was used as positive control

Results:
1. DSS-induction of colitis was manifested with significant increase in clinical disease activity index associated with weight loss, decrease in colon length, reduction in hematocrit, increased rectal bleeding, increase in colon blood and loose stools (FIGS. 1-6).
2. Compound of Example 25 attenuated DSS-induced body weight loss (FIG. 1)
3. Compound of Example 25 inhibited DSS-induced (i) shortening of colon, and (ii) decrease in hematocrit (FIGS. 2 and 3)
4. Compound of Example 25 improved rectal bleeding index (FIG. 4)
5. Compound of Example 25 attenuated the DSS-induced colon bleeding (FIG. 5)
6. Compound of Example 25 reduced DSS-induced disease activity index (FIG. 6)

It should be noted that, as used in this specification and the appended claims, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:
1. A compound of formula (I)

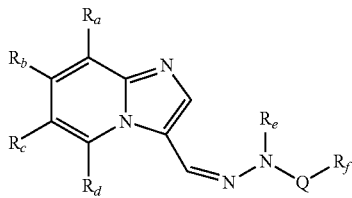

(I)

wherein,
$R_a$, $R_b$ and $R_d$ are independently selected from hydrogen, hydroxy, halogen, cyano, nitro, —$COR_1$, —$COOR_1$, —$CONH_2$, —$NR_1R_2$, —$C_1$-$C_8$ alkyl, halo-$C_1$-$C_8$ alkyl and —$C_1$-$C_8$ alkoxy;
$R_c$ is halogen or heteroaryl;
$R_e$ is hydrogen, —$C_1$-$C_8$ alkyl, —$C_6$-$C_{14}$ aryl or heteroaryl;
Q is —$SO_2$, —$C(O)NR_1$ or —$C(S)NR_1$;
$R_f$ is —$C_1$-$C_8$ alkyl, —$(CR_1R_2)_p$—$C_3$-$C_8$ cycloalkyl, —$(CR_1R_2)_p$—$C_6$-$C_{14}$ aryl, —$(CR_1R_2)_p$ heterocyclyl, —$(CR_1R_2)_p$heteroaryl, —$C_3$-$C_8$cycloalkyl, —$C_6$-$C_{14}$aryl, heteroaryl or heterocyclyl;
$R_1$ and $R_2$ are independently selected from hydrogen and lower alkyl;
p is independently an integer from 1 to 3;
with the proviso that when Q is —$SO_2$, then $R_c$ is not halogen;
wherein each of the above alkyl, haloalkyl, alkoxy, cycloalkyl, aryl, heteroaryl and heterocyclyl are unsubstituted or substituted with one or more of the same or different groups selected from halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo-$C_1$-$C_6$ alkyl, halo-$C_1$-$C_6$ alkoxy, —$C_1$-$C_6$ alkoxy, haloalkoxy, —$C_3$-$C_8$ cycloalkyl, —$(CR_1R_2)_p$-aryl, —$C_6$-$C_{10}$ aryl, —NHCOMe, —$S(O)_2Me$, aryloxy, heterocyclyl and heteroaryl; or
a stereoisomer, tautomer, N-oxide or a pharmaceutically acceptable salt thereof.

2. The compound according to claim 1, wherein
$R_a$, $R_b$ and $R_d$ are independently selected from hydrogen and —$C_1$-$C_8$ alkyl;
$R_c$ is halogen or heteroaryl;
$R_e$ is hydrogen or —$C_1$-$C_8$ alkyl;
Q is —$SO_2$, —$C(O)NR_1$ or —$C(S)NR_1$;
$R_f$ is —$C_1$-$C_8$ alkyl, —$(CR_1R_2)_p$—$C_3$-$C_8$ cycloalkyl, —$(CR_1R_2)_p$—$C_6$-$C_{14}$ aryl, —$(CR_1R_2)_p$-heterocyclyl, —$(CR_1R_2)_p$-heteroaryl, —$C_3$-$C_8$ cycloalkyl, —$C_6$-$C_{14}$ aryl, heteroaryl or heterocyclyl;
$R_1$ and $R_2$ are independently selected from hydrogen and lower alkyl;
p is independently an integer from 1 to 3;
with the proviso that when Q is —$SO_2$, then $R_1$ is not halogen;
wherein each of the above alkyl, cycloalkyl, aryl, heterocyclyl and heteroaryl are unsubstituted or substituted with one or more of the same or different groups selected from halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo-$C_1$-$C_6$ alkyl, halo-$C_1$-$C_6$ alkoxy, —$C_1$-$C_6$ alkoxy, —$C_3$-$C_8$ cycloalkyl, —$(CR_1R_2)_p$—$C_6$-$C_{10}$ aryl, —$C_6$-$C_{10}$ aryl, —NHCOMe, —$S(O)_2Me$, aryloxy, heterocyclyl and heteroaryl; or
a stereoisomer, tautomer, N-oxide or a pharmaceutically acceptable salt thereof.

3. The compound according to claim 1, wherein
$R_a$, $R_b$ and $R_d$ are independently selected from hydrogen and —$C_1$-$C_4$ alkyl;
$R_c$ is halogen or heteroaryl;
$R_e$ is hydrogen or —$C_1$-$C_4$ alkyl;
Q is —$SO_2$, —$C(O)NH$ or —$C(S)NH$;
$R_f$ is —$C_1$-$C_8$ alkyl, —$(CR_1R_2)_p$—$C_6$-$C_{14}$aryl, —$(CR_1R_2)_p$ heterocyclyl, —$C_3$-$C_8$ cycloalkyl, —$C_6$-$C_{14}$ aryl, heterocyclyl, or heteroaryl;
$R_1$ and $R_2$ are independently selected from hydrogen and lower alkyl;
p is independently an integer from 1 to 3;
with the proviso that when Q is —$SO_2$, then $R_c$ is not halogen;
wherein each of the above alkyl, cycloalkyl, aryl, heteroaryl and heterocyclyl are optionally and independently substituted with one or more of the same or different groups selected from halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo—$C_1$-$C_6$ alkyl, halo-$C_1$-$C_6$ alkoxy, —$C_1$-$C_6$ alkoxy, —NHCOMe, —$S(O)_2Me$, aryloxy, heterocyclyl and heteroaryl; or
a stereoisomer, tautomer, N-oxide or a pharmaceutically acceptable salt thereof.

4. The compound according to claim 1, wherein,
$R_a$, $R_b$ and $R_d$ are independently selected from hydrogen and —$C_1$-$C_4$ alkyl;
$R_c$ is halogen or heteroaryl;
$R_e$ is hydrogen or —$C_1$-$C_4$ alkyl;
Q is —$C(O)NH$ or —$C(S)NH$;
$R_f$ is —$C_1$-$C_8$ alkyl, —$(CR_1R_2)_p$—$C_6$-$C_{14}$ aryl, —$(CR_1R_2)_p$-heterocyclyl, —$C_3$-$C_8$ cycloalkyl, —$C_6$-$C_{14}$ aryl or heteroaryl;
$R_1$ and $R_2$ are independently selected from hydrogen and lower alkyl;
p is independently an integer from 1 to 3;
wherein each of the above alkyl, cycloalkyl, aryl and heteroaryl are optionally and independently substituted with one or more of the same or different groups selected from halogen, hydroxy, cyano, amino, nitro, alkoxy, —$C_1$-$C_6$ alkyl and halo —$C_1$-$C_6$ alkyl; or
a stereoisomer, tautomer, N-oxide or a pharmaceutically acceptable salt thereof.

5. The compound according to claim 1, wherein
$R_a$, $R_b$ and $R_d$ are independently selected from hydrogen and —$C_1$-$C_4$ alkyl;
$R_c$ is halogen or heteroaryl;
$R_e$ is hydrogen or —$C_1$-$C_4$ alkyl;
Q is —$C(O)NH$ or —$C(S)NH$;

$R_f$ is —$(CR_1R_2)_p$-heterocyclyl, —$(CR_1R_2)_p$—$C_6$-$C_{14}$ aryl or —$C_6$-$C_{14}$ aryl;

$R_1$ and $R_2$ are independently selected from hydrogen and lower alkyl;

p is independently an integer from 1 to 3;

wherein each of the above alkyl, aryl and heteroaryl are optionally and independently substituted with one or more of the same or different groups selected from halogen, hydroxy, cyano, amino, nitro, alkoxy, —$C_1$-$C_6$ alkyl and halo —$C_1$-$C_6$ alkyl; or a stereoisomer, tautomer, N-oxide or a pharmaceutically acceptable salt thereof.

6. The compound according to claim 1, wherein $R_a$, $R_b$ and $R_d$ are independently selected from hydrogen and —$C_1$-$C_4$ alkyl;

$R_c$ is halogen;

$R_e$ is hydrogen or —$C_1$-$C_4$ alkyl;

Q is —C(O)NH or —C(S)NH;

$R_f$ is —$(CR_1R_2)_p$-heterocyclyl, —$(CR_1R_2)_p$—$C_6$-$C_{14}$ aryl or —$C_6$-$C_{14}$ aryl;

$R_1$ and $R_2$ are independently selected from hydrogen and lower alkyl;

p is independently an integer from 1 to 3;

wherein each of the above alkyl, aryl and heteroaryl are optionally and independently substituted with one or more of the same or different groups selected from halogen, hydroxy, cyano, amino, nitro, alkoxy, —$C_1$-$C_6$ alkyl and halo-$C_1$-$C_6$ alkyl; or a stereoisomer, tautomer, N-oxide or a pharmaceutically acceptable salt thereof.

7. The compound according to claim 1, wherein $R_a$, $R_b$ and $R_d$ are independently selected from hydrogen and —$C_1$-$C_4$ alkyl;

$R_c$ is heteroaryl;

$R_e$ is hydrogen or —$C_1$-$C_4$ alkyl;

Q is —$SO_2$, —C(O)$NR_1$ or —C(S)$NR_1$;

$R_f$ is —$C_1$-$C_8$ alkyl, —$(CR_1R_2)_1$—$C_3$-$C_8$ cycloalkyl, —$(CR_1R_2)_p$—$C_6$-$C_{14}$ aryl, —$(CR_1R_2)_p$-heterocyclyl, —$(CR_1R_2)_p$-heteroaryl, —$C_3$-$C_8$ cycloalkyl, —$C_6$-$C_{14}$ aryl, heteroaryl or heterocyclyl;

$R_1$ and $R_2$ are independently selected from hydrogen and lower alkyl;

p is independently an integer from 1 to 3;

wherein each of the above alkyl, cycloalkyl, aryl, heterocyclyl and heteroaryl are optionally and independently substituted with one or more of the same or different groups selected from halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo—$C_1$-$C_6$ alkyl, —$C_1$-$C_6$ alkoxy, —$C_3$-$C_8$ cycloalkyl, —$(CR_1R_2)_p$—$C_6$-$C_{10}$ aryl, —$C_6$-$C_{10}$ aryl, —NHCOMe, —$S(O)_2$Me, aryloxy, heterocyclyl and heteroaryl; or a stereoisomer, tautomer, N-oxide or a pharmaceutically acceptable salt thereof.

8. The compound according to claim 1, wherein $R_a$, $R_b$ and $R_d$ are independently selected from hydrogen and —$C_1$-$C_4$ alkyl;

$R_c$ is heteroaryl;

$R_e$ is hydrogen or —$C_1$-$C_4$ alkyl;

Q is —$SO_2$, —C(O)NH or —C(S)NH;

$R_f$ is —$C_1$-$C_8$ alkyl, —$(CH_2)_p$—$C_6$-$C_{14}$ aryl, —$(CH_2)_p$-heterocyclyl, —$C_3$-$C_8$ cycloalkyl, —$C_6$-$C_{14}$ aryl, heteroaryl or heterocyclyl;

p is independently an integer from 1 to 3;

$R_1$ and $R_2$ are independently selected from hydrogen and lower alkyl;

wherein each of the above alkyl, aryl, heterocyclyl and heteroaryl are optionally and independently substituted with one or more of the same or different groups selected from halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo—$C_1$-$C_6$ alkyl, —$C_1$-$C_6$ alkoxy, —$C_3$-$C_8$ cycloalkyl, —$(CR_1R_2)_p$—$C_6$-$C_{10}$ aryl, —$C_6$-$C_{10}$ aryl, —NHCOMe, —$S(O)_2$Me, aryloxy, heterocyclyl and heteroaryl; or a stereoisomer, tautomer, N-oxide or a pharmaceutically acceptable salt thereof.

9. The compound according to claim 1, wherein $R_a$, $R_b$ and $R_d$ are independently selected from hydrogen and methyl;

$R_c$ is halogen or heteroaryl selected from indolyl, pyrrolyl, pyridyl, pyrimidinyl and quinolinyl wherein each of indolyl, pyrrolyl, pyridyl, pyrimidinyl and quinolinyl is optionally substituted with one or more groups selected from halogen, —$C_1$-$C_6$-alkyl, —$C_1$-$C_6$-alkoxy, and halo—$C_1$-$C_6$-alkyl;

$R_e$ is hydrogen or —$C_1$-$C_4$ alkyl;

Q is —$SO_2$, —C(O)NH or —C(S)NH;

$R_f$ is —$C_1$-$C_8$ alkyl, —$(CH_2)_p$—$C_6$-$C_{14}$ aryl, —$(CH_2)_p$-heterocyclyl, —$C_3$-$C_8$-cycloalkyl, —$C_6$-$C_{14}$ aryl, heterocyclyl or heteroaryl;

p is independently an integer from 1 to 3;

$R_1$ and $R_2$ are independently selected from hydrogen and lower alkyl;

with the proviso that when Q is —$SO_2$, then $R_c$ is not halogen;

wherein each of the above alkyl, cycloalkyl, aryl, heteroaryl and heterocyclyl are optionally and independently substituted with one or more of the same or different groups selected from halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo—$C_1$-$C_6$ alkyl, halo—$C_1$-$C_6$ alkoxy, —$C_1$-$C_6$ alkoxy, —$C_3$-$C_8$ cycloalkyl, —$(CR_1R_2)_p$—$C_6$-$C_{10}$ aryl, —$C_6$-$C_{10}$ aryl, —NHCOMe, —$S(O)_2$Me, aryloxy, heterocyclyl and heteroaryl group;

a stereoisomer, tautomer, N-oxide or a pharmaceutically acceptable salt thereof.

10. The compound according to claim 1, wherein $R_a$, $R_b$ and $R_d$ are independently selected from hydrogen and —$C_1$-$C_4$ alkyl;

$R_c$ is heteroaryl;

$R_e$ is hydrogen or —$C_1$-$C_4$alkyl;

Q is —$SO_2$;

$R_f$ is —$C_1$-$C_8$ alkyl, —$(CR_1R_2)_p$—$C_6$-$C_{14}$ aryl, —$C_3$-$C_8$ cycloalkyl, —$C_6$-$C_{14}$ aryl, heterocyclyl or heteroaryl;

$R_1$ and $R_2$ are independently selected from hydrogen and lower alkyl;

p is independently an integer from 1 to 3;

wherein each of the above alkyl, cycloalkyl, aryl, heterocyclyl and heteroaryl are unsubstituted or substituted with one or more of the same or different groups selected from halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo—$C_1$-$C_6$ alkyl, halo—$C_1$-$C_6$ alkoxy, —$C_1$-$C_6$ alkoxy, —$C_3$-$C_8$ cycloalkyl, —$(CR_1R_2)_p$—$C_6$-$C_{10}$aryl, —$C_6$-$C_{10}$ aryl, —NHCOMe, —$S(O)_2$Me, aryloxy, heterocyclyl and heteroaryl group; or a stereoisomer, tautomer, N-oxide or a pharmaceutically acceptable salt thereof.

11. The compound according to claim 1, wherein $R_a$, $R_b$ and $R_d$ are independently selected from hydrogen and methyl;

$R_c$ is heteroaryl selected from indolyl, pyrrolyl, pyridyl, pyrimidinyl and quinolinyl, wherein each of indolyl, pyrrolyl, pyridyl, pyrimidinyl and quinolinyl is optionally substituted with one or more groups selected from halogen, —$C_1$-$C_6$-alkyl, —$C_1$-$C_6$-alkoxy, and halo—$C_1$-$C_6$-alkyl;

$R_e$ is hydrogen or —$C_1$-$C_4$ alkyl;

Q is —$SO_2$;

$R_f$ is —$(CH_2)_p$—$C_6$-$C_{14}$ aryl, —$C_3$-$C_8$ cycloalkyl, —$C_6$-$C_{14}$ aryl, heteroaryl or heterocyclyl;

$R_1$ and $R_2$ are independently selected from hydrogen and lower alkyl;

p is independently an integer from 1 to 3;

wherein each of the above alkyl, cycloalkyl, aryl, heterocyclyl and heteroaryl are unsubstituted or substituted with one or more of the same or different groups selected from halogen, hydroxy, carbonyl, carboxy, ester, ether, acyl, acyloxy, cyano, amino, amide, imino, alkylthio, thioester, sulfonyl, nitro, —$C_1$-$C_6$ alkyl, halo—$C_1$-$C_6$ alkyl, halo—$C_1$-$C_6$ alkoxy, —$C_1$-$C_6$ alkoxy, —$C_3$-$C_8$ cycloalkyl, —$(CR_1R_2)_p$—$C_6$-$C_{10}$ aryl, —$C_6$-$C_{10}$aryl, —NHCOMe, —$S(O)_2$Me, aryloxy, heterocyclyl and heteroaryl group; or a stereoisomer, tautomer, N-oxide or a pharmaceutically acceptable salt thereof.

12. The compound according to claim 1, selected from:

N-methyl-N'-((6-(pyridin-3-yl)imidazo[1,2-a]pyridin-3-yl)methylene)benzenesulfonohydrazide;

N,3-dimethyl-N'-((6-pyridin-3-yl)imidazo[1,2-a]pyridine-3-yl)methylene) benzenesulfonohydrazide;

N,4-dimethyl-N'-((6-(pyridine-3-yl)imidazo[1,2-a]pyridine-3-yl)methylene) benzenesulfonohydrazide;

2-Fluoro-N-methyl-N'-((6-(pyridine-3-yl)imidazo[1,2-a]pyridine-3-yl)methylene) benzenesulfonohydrazide;

3-Fluoro-N-methyl-N'-((6-(pyridine-3-yl)imidazo[1,2-a]pyridine-3-yl) methylene)benzenesulfonohydrazide;

4-Fluoro-N-methyl-N'-((6-(pyridine-3-yl)imidazo[1,2-a]pyridine-3-yl)methylene) benzenesulfonohydrazide;

3-Bromo-N-methyl-N'-((6-(pyridine-3-yl)imidazo[1,2-a]pyridine-3-yl)methylene) benzenesulfonohydrazide;

4-Bromo-N-methyl-N'-((6-(pyridine-3-yl)imidazo[1,2-a]pyridine-3-yl)methylene) benzenesulfonohydrazide;

2-Cyano-N-methyl-N'-((6-(pyridine-3-yl)imidazo[1,2-a]pyridine-3-yl)methylene) benzenesulfonohydrazide;

(E)-3-cyano-N-methyl-N'-((6-(pyridin-3-yl)imidazo[1,2-a]pyridin-3-yl)methylene)benzenesulfonohydrazide;

4-Cyano-N-methyl-N'-((6-(pyridine-3-yl)imidazo[1,2-a]pyridine-3-yl)methylene) benzenesulfonohydrazide;

4-Methoxy-N-methyl-N'-((6-(pyridine-3-yl)imidazo[1,2-a]pyridine-3-yl) methylene)benzenesulfonohydrazide;

2,4-Difluoro-N-methyl-N'-((6-(pyridine-3-yl)imidazo[1,2-a]pyridine-3-yl)methylene) benzenesulfonohydrazide;

2,6-Difluoro-N-methyl-N'-((6-(pyridine-3-yl)imidazo[1,2-a]pyridine-3-yl)methylene) benzenesulfonohydrazide;

3,4-difluoro-N-methyl-N'-((6-(pyridine-3-yl)imidazo[1,2-a]pyridine-3-yl)methylene) benzenesulfonohydrazide;

3,5-Difluoro-N-methyl-N'-((6-(pyridine-3-yl)imidazo[1,2-a]pyridine-3-yl)methylene) benzenesulfonohydrazide;

3-Chloro-2-fluoro-N-methyl-N'-((6-(pyridine-3-yl)imidazo[1,2-a]pyridine-3-yl) methylene)benzenesulfonohydrazide;

3-Chloro-4-fluoro-N-methyl-N'-((6-(pyridine-3-yl)imidazo[1,2-a]pyridine-3-yl) methylene)benzenesulfonohydrazide;

2-Fluoro-N,5-dimethyl-N'-((6-(pyridine-3-yl)imidazo[1,2-a]pyridine-3-yl)methylene) benzenesulfonohydrazide;

3-Fluoro-N,4-dimethyl-N'-((6-(pyridine-3-yl)imidazo[1,2-a]pyridine-3-yl)methylene) benzenesulfonohydrazide;

5-Fluoro-N,2-dimethyl-N'-((6-(pyridine-3-yl)imidazo[1,2-a]pyridine-3-yl)methylene) benzenesulfonohydrazide;

3-(3-((2-(5-fluoro-2-methylphenylsulfonyl)-2-methylhydrazono)methyl)imidazo[1,2-a]pyridin-6-yl)pyridine 1-oxide;

4-Bromo-N,3-dimethyl-N'-((6-(pyridine-3-yl)imidazo[1,2-a]pyridine-3-yl) methylene)benzenesulfonohydrazide;

N-methyl-N'-((6-(pyridine-3-yl)imidazo[1,2-a]pyridine-3-yl)methylene)-3,5-bis (trifluoromethyl)benzenesulfonohydrazide;

3-Cyano-4-fluoro-N-methyl-N'-((6-(pyridine-3-yl)imidazo[1,2-a]pyridine-3-yl) methylene)benzenesulfonohydrazide;

N,2-dimethyl-5nitro-N'-((6-pyridin-3-yl)imidazo[1,2-a]pyridine-3-yl) methylene)benzenesulfonohydrazide;

2-Bromo-4,6-difluoro-N-methyl-N'-((6-(pyridine-3-yl)imidazo[1,2-a]pyridine-3-yl) methylene)benzenesulfonohydrazide;

N,2,4,6-tetramethyl-N'-((6-(pyridine-3-yl)imidazo[1,2-a]pyridine-3-yl)methylene) benzenesulfonohydrazide;

N-methyl-1-phenyl-N'-((6-pyridin-3-yl)imidazo[1,2-a]pyridine-3-yl)methylene) benzenesulfonohydrazide;

N-methyl-N'-((6-(pyridine-3-yl)imidazo[1,2-a]pyridine-3-yl)methylene)thiophene-2-sulfonohydrazide;

N-methyl-N'-((6-(pyridine-3-yl)imidazo[1,2-a]pyridine-3-yl)methylene) quinoline-8-sulfonohydrazide;

N-methyl-N'-((6-(pyridine-3-yl)imidazo[1,2-a]pyridine-3-yl)methylene) cyclohexanesulfonohydrazide;

3-Fluoro-N,4-dimethyl-N'-((6-(pyridine-3-yl)imidazo[1,2-a]pyridine-3-yl)methylene) benzenesulfonohydrazide;

3-Cyano-4-fluoro-N-methyl-N'-((6-(pyridine-3-yl)imidazo[1,2-a]pyridine-3-yl) methylene)benzenesulfonohydrazide;

(E)-2,3,4-Trifluoro-N-methyl-N'-((6-(pyridin-3-yl)imidazo[1,2-a]pyridin-3-yl) methylene)benzenesulfonohydrazide;

(E)-4-bromo-2,5-difluoro-N-methyl-N'-((6-(pyridin-3-yl)imidazo[1,2-a]pyridin-3-yl) methylene)benzenesulfonohydrazide;

(E)-2-bromo-4-fluoro-N-methyl-N'-((6-(pyridin-3-yl)imidazo[1,2-a]pyridin-3-yl) methylene)benzenesulfonohydrazide;

(E)-N-methyl-N'-((6-(pyridin-3-yl)imidazo[1,2-a]pyridin-3-yl)methylene)-3-(trifluoromethyl) benzenesulfonohydrazide;

(E)-4-bromo-2,6-dichloro-N-methyl-N'-((6-(pyridin-3-yl)imidazo[1,2-a]pyridin-3-yl) methylene)benzenesulfonohydrazide;

(E)-3-chloro-N-methyl-N'-((6-(pyridin-3-yl)imidazo[1,2-a]pyridin-3-yl) methylene)benzenesulfonohydrazide;

(E)-2-chloro-N-methyl-N'-((6-(pyridin-3yl)imidazo[1,2-a]pyridin-3-yl)methylene)-4-(trifluoromethyl)benzenesulfonohydrazide;
(E)-2-chloro-4-fluoro-N-methyl-N'((6-(pyridin-3-yl)imidazo[1,2-a]pyridin-3-yl) methylene)benzenesulfonoydrazide;
(E)-N,1,2-trimethyl-N'-((6-(pyridin-3-yl)imidazo[1,2-a]pyridin-3-yl)methylene)-1H-imidazole-4-sulfonohydrazide;
(E)-4-chloro-N,2,5-trimethyl-N'((6-(pyridin-3-yl)imidazo[1,2-a]pyridin-3-yl)methylene) benzenesulfonohydrazide;
(E)-2,5-difluoro-N-methyl-N'-((6-(pyridin-3-yl)imidazo[1,2-a]pyridin-3-yl)methylene) benzenesulfonohydrazide;
(E)-5-fluoro-2-methoxy-N-methyl-N'((6-(pyridin-3-yl)imidazo[1,2-a]pyridin-3-yl) methylene)benzenesulfonohydrazide;
(E)-4-Iodo-N-methyl-N'-((6-(pyridin-3-yl)imidazo[1,2-a]pyridin-3-yl) methylene)benzenesulfonohydrazide;
(E)-2'-Fluoro-N-methyl-N'-((6-(pyridin-3-yl)imidazo[1,2-a]pyridin-3-yl)methylene)-5'-(trifluoromethyl)biphenyl-4-sulfonohydrazide;
4-Methyl-3-(1-methyl-2-((6-(pyridin-3-yl)imidazo[1,2-a]pyridin-3-yl)methylene) hydrazinylsulfonyl)benzoic acid;
4-Methoxy-3-(1-methyl-2-((6-(pyridin-3-yl)imidazo[1,2-a]pyridin-3-yl) methylene)hydrazinylsulfonyl)benzamide;
(E)-N,2,5-trimethyl-N'((6-(pyridin-3-yl)imidazo[1,2-a]pyridin-3-yl)methylene) benzenesulfonohydrazide;
(E)-2,5-dibromo-N-methyl-N'-((6-(pyridin-3-yl)imidazo[1,2-a]pyridin-3-yl)methylene) benzenesulfonohydrazide;
(E)-2,5-dimethoxy-N-methyl-N'((6-(pyridin-3-yl)imidazo[1,2-a]pyridin-3-yl)methylene) benzenesulfonohydrazide;
(E)-N,2-dimethyl-N'-((6-(pyridin-3-yl)imidazo[1,2-a]pyridin-3-yl)methylene) benzenesulfonohydrazide;
(E)-N-methyl-N'-((6-(pyridin-3-yl)imidazo[1,2-a]pyridin-3-yl)methylene)-2-(trifluoromethoxy)benzenesulfonohydrazide;
(E)-5-chloro-2-methoxy-N-methyl-N-'-((6-(pyridin-3-yl)imidazo[1,2-a]pyridin-3-yl) methylene)benzenesulfonohydrazide;
(E)-4-bromo-N-methyl-N'-((6-(pyridin-3-yl)imidazo[1,2-a]pyridin-3-yl)methylene)-2-(trifluoromethoxy)benzenesulfonohydrazide;
(E)-2-bromo-N-methyl-N'-((6-(pyridin-3-yl)imidazo[1,2-a]pyridin-3-yl)methylene)-5-(trifluoromethyl)benzenesulfonohydrazide;
(E)-N-methyl-2-nitro-N'-((6-(pyridin-3-yl)imidazo[1,2-a]pyridin-3-yl) methylene)benzenesulfonohydrazide;
(E)-N-methyl-2-(methylsulfonyl)-N'-((6-(pyridin-3-yl)imidazo[1,2-a]pyridin-3-yl) methylene)benzenesulfonohydrazide
(E)-N-methyl-2-phenoxy-N'-((6-(pyridin-3-yl)imidazo[1,2-a]pyridin-3-yl) methylene)benzenesulfonohydrazide;
(E)-N-methyl-N'-((6-(pyridin-3-yl)imidazo[1,2-a]pyridin-3-yl)methylene) hexane-1-sulfonohydrazide;
(E)-N-methyl-2-morpholino-N'-((6-(pyridin-3-yl)imidazo[1,2-a]pyridin-3-yl)methylene)-5-(trifluoromethyl)benzenesulfonohydrazide;
(E)-N,2-dimethyl-5-(methylsulfonyl)-N'-((6-(pyridin-3-yl)imidazo[1,2-a]pyridin-3-yl) methylene)benzenesulfonohydrazide;
(E)-2-bromo-N-methyl-N'-((6-(pyridin-3-yl)imidazo[1,2-a]pyridin-3-yl)methylene) benzenesulfonohydrazide;
(E)-2-chloro-N-methyl-N'-((6-(pyridin-3-yl)imidazo[1,2-a]pyridin-3-yl)methylene)-5-(trifluoromethyl)benzenesulfonohydrazide;
(E)-N-methyl-6-morpholino-N'-((6-(pyridin-3-yl)imidazo[1,2-a]pyridin-3-yl)methylene) pyridine-3-sulfonohydrazide
(E)-Methyl 1-methyl-5-(1-methyl-2-((6-(pyridin-3-yl)imidazo[1,2-a]pyridin-3-yl) methylene)hydrazinylsulfonyl)-1H-pyrrole-2-carboxylate;
(E)-N,4-dimethyl-N'-((6-(pyridin-3-yl)imidazo[1,2-a]pyridin-3-yl)methylene)-3,4-dihydro-2H-pyrido[3,2-b][1,4]oxazine-7-sulfonohydrazide;
(E)-N-methyl-N'-((6-(pyridin-3-yl)imidazo[1,2-a]pyridin-3-yl)methylene)pyridine-3-sulfonohydrazide;
(E)-N-methyl-4-phenoxy-N'-((6-(pyridin-3-yl)imidazo[1,2-a]pyridin-3-yl)methylene) benzenesulfonohydrazide;
(E)-Methyl 3-(1-methyl-2-((6-(pyridin-3-yl)imidazo[1,2-a]pyridin-3-yl)methylene) hydrazinylsulfonyl)thiophene-2-carboxylate;
(E)-N-methyl-N'-((6-(pyridin-3-yl)imidazo[1,2-a]pyridin-3-yl)methylene)biphenyl-4-sulfonohydrazide;
(E)-Methyl 5-(1-methyl-2-((6-(pyridin-3-yl)imidazo[1,2-a]pyridin-3-yl)methylene)hydrazinylsulfonyl) furan-2-carboxylate;
(E)-4-chloro-N-methyl-3-nitro-N'-((6-(pyridin-3-yl)imidazo[1,2-a]pyridin-3-yl)methylene) benzenesulfonohydrazide;
(E)-5-bromo-2-methoxy-N-methyl-N'-((6-(pyridin-3-yl)imidazo[1,2-a]pyridin-3-yl) methylene)benzenesulfonohydrazide;
(E)-3-chloro-N,2-dimethyl-N'-((6-(pyridin-3-yl)imidazo[1,2-a]pyridin-3-yl)methylene) benzenesulfonohydrazide;
(E)-5-chloro-2-fluoro-N-methyl-N'-((6-(pyridin-3-yl)imidazo[1,2-a]pyridin-3-yl) methylene)benzenesulfonohydrazide;
(E)-4-Fluoro-N,2-dimethyl-N'-((6-(pyridin-3-yl)imidazo[1,2-a]pyridin-3-yl)methylene) benzenesulfonohydrazide;
(E)-2-methoxy-N,6-dimethyl-N'-((6-(pyridin-3-yl)imidazo[1,2-a]pyridin-3-yl) methylene)benzenesulfonohydrazide;
(E)-4-Bromo-2-chloro-N-methyl-N'-((6-(pyridin-3-yl)imidazo[1,2-a]pyridin-3-yl) methylene)benzenesulfonohydrazide;
(E)-2-chloro-N-methyl-N'-((6-(pyridin-3-yl)imidazo[1,2-a]pyridin-3-yl)methylene) benzenesulfonohydrazide;
(E)-N-(4-(1-methyl-2-((6-(pyridin-3-yl)imidazo[1,2-a]pyridin-3-yl)methylene) hydrazinylsulfonyl)phenyl)acetamide;
N'-((6-(6-fluoropyridine-3-yl)imidazo[1,2-a]pyridine-3-yl)methylene)-n,2-dimethyl-5-nitrobenzenesulfonohydrazide;
(E)-N-ethyl-2-methyl-5-nitro-N'-((6-(pyridin-3-yl)imidazo[1,2-a]pyridin-3-yl) methylene)benzenesulfonohydrazide;
N,2-dimethyl-5-nitro-N'-((6-(pyridine-4-yl)imidazo[1,2-a]pyridin-3-yl)methylene) benzenesulfonohydrazide;
5-Fluoro-N,2-dimethyl-N'-((6-(pyridine-4-yl)imidazo[1,2-a]pyridine-3-yl)methylene) benzenesulfonohydrazide;
(E)-5-Fluoro-N'-((6-(2-fluoropyridin-3-yl)imidazo[1,2-a]pyridin-3-yl)methylene)-N,2-dimethylbenzenesulfonohydrazide;

(E)-5-Fluoro-N'-((6-(2-fluoropyridin-3-yl)imidazo[1,2-a] pyridin-3-yl)methylene)-2-methoxy-N-methylbenzenesulfonohydrazide;

(E)-3-fluoro-N'-((6-(2-fluoropyridin-3-yl)imidazo[1,2-a] pyridin-3-yl)methylene)-N-methylbenzenesulfonohydrazide;

(E)-5-chloro-2-fluoro-N'46-(2-fluoropyridin-3-yl)imidazo[1,2-a]pyridin-3-yl)methylene)-N-methylbenzenesulfonohydrazide;

(E)-5-bromo-N'-((6-(2-fluoropyridin-3-yl)imidazo[1,2-a] pyridin-3-yl)methylene)-2-methoxy-N-methylbenzenesulfonohydrazide (E)-N'-((6-(2-fluoropyridin-3-yl)imidazo[1,2-a]pyridin-3-yl)methylene)-2,5-dimethoxy-N-methylbenzenesulfonohydrazide;

(E)-N'-((6-(2-fluoropyridin-3-yl)imidazo[1,2-a]pyridin-3-yl)methylene)-N,2-dimethyl-5-(methylsulfonyl)benzenesulfonohydrazide;

(E)-N'-((6-(2-fluoropyridin-3-yl)imidazo[1,2-a]pyridin-3-yl)methylene)-N-methylhexane-1-sulfonohydrazide;

(E)-N'-((6-(2-fluoropyridin-3-yl)imidazo[1,2-a]pyridin-3-yl)methylene)-2-methoxy-N,4-dimethylbenzenesulfonohydrazide;

(E)-2-bromo-N'-((6-(2-fluoropyridin-3-yl)imidazo[1,2-a] pyridin-3-yl)methylene)-N-methylbenzenesulfonohydrazide;

(E)-2-cyano-N'-((6-(2-fluoropyridin-3-yl)imidazo[1,2-a] pyridin-3-yl)methylene)-N-methylbenzenesulfonohydrazide;

(E)-N'-((6-(2-fluoropyridin-3-yl)imidazo[1,2-a]pyridin-3-yl)methylene)-2-methoxy-N,5-dimethylbenzenesulfonohydrazide;

N,2-Dimethyl-5-nitro-N'-((6-(quinolin-3-yl)imidazo[1,2-a]pyridine-3-yl)methylene) benzenesulfonohydrazide;

(E)-5-Fluoro-N,2-dimethyl-N'-((8-methyl-6-(pyridin-3-yl)imidazo[1,2-a]pyridin-3-yl)methylene)benzenesulfonohydrazide;

(E)-3,5-Difluoro-N-methyl-N'-((8-methyl-6-(pyridin-3-ypimidazo[1,2-a]pyridin-3-yl)methylene)benzenesulfonohydrazide;

(E)-4-Bromo-2,6-difluoro-N-methyl-N'-((8-methyl-6-(pyridin-3-yl)imidazo[1,2-a]pyridin-3-yl)methylene) benzenesulfonohydrazide;

(E)-N,3-dimethyl-N'-((8-methyl-6-(pyridin-3-yl)imidazo [1,2-a]pyridin-3-yl)methylene)benzenesulfonohydrazide;

(E)-2-cyano-N-methyl-N'-((8-methyl-6-(pyridin-3-yl) imidazo[1,2-a]pyridin-3-yl)methylene)benzenesulfonohydrazide;

(E)-3-cyano-4-fluoro-N-methyl-N'-((8-methyl-6-(pyridin-3-yl)imidazo[1,2-a]pyridin-3-yl)methylene)benzenesulfonohydrazide;

(E)-3-cyano-N-methyl-N'-((8-methyl-6-(pyridin-3-yl) imidazo[1,2-a]pyridin-3-yl)methylene)benzenesulfonohydrazide;

(E)-4-Bromo-N,3-dimethyl-N'-((8-methyl-6-(pyridin-3-yl)imidazo[1,2-a]pyridin-3-yl)methylene)benzenesulfonohydrazide;

(E)-3-Methoxy-N-methyl-N'-((8-methyl-6-(pyridin-3-yl) imidazo[1,2-a]pyridin-3-yl)methylene)benzenesulfonohydrazide;

(E)-N-methyl-N'-((8-methyl-6-(pyridin-3-yl)imidazo[1, 2-a]pyridin-3-yl)methylene)-3-nitrobenzenesulfonohydrazide;

(E)-3-Chloro-N-methyl-N'-((8-methyl-6-(pyridin-3-yl) imidazo[1,2-a]pyridin-3-yl)methylene)benzenesulfonohydrazide;

(E)-N-methyl-N'-((8-methyl-6-(pyridin-3-yl)imidazo[1, 2-a]pyridin-3-yl)methylene)-3-(trifluoromethyl)benzenesulfonohydrazide;

(E)-2-Bromo-4,6-difluoro-N-methyl-N'-((8-methyl-6-(pyridin-3-yl)imidazo[1,2-a]pyridin-3-yl)methylene) benzenesulfonohydrazide;

(E)-4-Chloro-N-methyl-N'-((8-methyl-6-(pyridin-3-yl) imidazo[1,2-a]pyridin-3-yl)methylene)-3-nitrobenzenesulfonohydrazide;

(E)-2-Bromo-4-fluoro-N-methyl-N'((8-methyl-6-(pyridin-3-yl)imidazo[1,2-a]pyridin-3-yl)methylene)benzenesulfonohydrazide;

(E)-N'-((6-(1H-indol-2-yl)imidazo[1,2-a]pyridin-3-yl) methylene)-5-fluoro-N,2-dimethylbenzenesulfonohydrazide;

(E)-5-fluoro-N,2-dimethyl-N'-((6-(1-methyl-1H-indol-3-yl)imidazo[1,2-a]pyridin-3-yl)methylene benzenesulfonohydrazide;

2-Cyano-N-methyl-N'((7-methyl-6-(pyridin-3-yl)imidazo [1,2-a]pyridin-3-yl)methylene) benzenesulfonohydrazide;

5-Fluoro-N,2-dimethyl-N'-((7-methyl-6-(pyridin-3-yl) imidazo [1,2-a]pyridin-3-yl) methylene)benzenesulfonohydrazide;

N,3-dimethyl-N'-((7-methyl-6-(pyridin-3-yl)imidazo [1,2-a]pyridin-3-yl) methylene)benzenesulfonohydrazide;

3-Fluoro-N-methyl-N'((7-methyl-6-(pyridin-3-yl)imidazo[1,2-a]pyridin-3-yl)methylene) benzenesulfonohydrazide;

3-Chloro-N-methyl-N'-((7-methyl-6-(pyridin-3-yl)imidazo[1,2-a]pyridin-3-yl)methylene )benzenesulfonohydrazide;

N-methyl-N'-((7-methyl-6-(pyridin-3-yl)imidazo[1,2-a] pyridin-3-yl)methylene)-3-(trifluoromethyl)benzenesulfonohydrazide;

3-Bromo-N-methyl-N'((7-methyl-6-(pyridin-3-yl)imidazo[1,2-a]pyridin-3-yl) methylene)benzenesulfonohydrazide;

5-Fluoro-N,2-dimethyl-N'-((7-methyl-6-(pyridin-3-yl) imidazo [1,2-a]pyridin-3-yl) methylene)benzenesulfonohydrazide;

N'-((6-(2,4-dimethoxypyrimidin-5-yl)imidazo[1,2-a]pyridin-3-yl)methylene)-5-fluoro-N,2-dimethylbenzenesulfonohydrazide;

(E)-5-Fluoro-N,2-dimethyl-N'-((5-methyl-6-(pyridin-3-yl)imidazo[1,2-a]pyridin-3-yl)methylene)benzenesulfonohydrazide;

(E)-N,3-dimethyl-N'-((5-methyl-6-(pyridin-3-yl)imidazo [1,2-a]pyridin-3-yl)methylene)benzenesulfonohydrazide;

(E)-5-fluoro-N,2-dimethyl-N'-((6-(6-methylpyridin-3-yl) imidazo[1,2-a]pyridin-3-yl)methylene)benzenesulfonohydrazide;

(E)-N-methyl-N'-((6-(6-methylpyridin-3-yl)imidazo[1,2-a]pyridin-3-yl)methylene)-2-(trifluoromethoxy)benzenesulfonohydrazide;

(E)-5-Fluoro-2-methoxy-N-methyl-N'-((6-(6-methylpyridin-3-yl)imidazo [1,2-a]pyridin-3-yl)methylene)benzenesulfonohydrazide;

(E)-N,2-dimethyl-N'((6-(6-methylpyridin-3-yl)imidazo [1,2-a]pyridin-3-yl)methylene)benzenesulfonohydrazide;

(E)-5-fluoro-N'-((6-(5-fluoropyridin-3-yl)imidazo[1,2-a] pyridin-3-yl)methylene)-N,2-dimethyl benzenesulfonohydrazide;

(E)-5-Fluoro-N'-((6-(5-fluoropyridin-3-yl)imidazo[1,2-a]pyridin-3-yl)methylene)-2-methoxy-N-methyl benzenesulfonohydrazide;

(E)-5-Fluoro-N'-((6-(6-fluoro-5-methylpyridin-3-yl)imidazo[1,2-a]pyridin-3-yl)methylene)-N,2-dimethyl benzenesulfonohydrazide;

(E)-N'-((6-(6-Chloropyridins-3-yl)imidazo[1,2-a]pyridin-3-yl)methylene)-5-fluoro-N,2-dimethylbenzenesulfonohydrazide;

(E)-N'-((6-(1H-Pyrrol-2-yl)imidazo[1,2-a]pyridin-3-yl)methylene)-5-fluoro-N,2-dimethyl benzenesulfonohydrazide;

(E)-5-fluoro-N'-((6-(6-methoxypyridin-3-yl)imidazo[1,2-a]pyridin-3-yl)methylene)-N,2-dimethyl benzenesulfonohydrazide;

(E)-5-Fluoro-N-((6-(2-methoxypyrimidin-5-yl)imidazo[1,2-a]pyridine-3-yl)methylene)-N,2-dimethylbenzenesulfonohydrazide;

(E)-5-fluoro-N,2-dimethyl-N'-((6-(5-(trifluoromethyl)pyridin-3-yl)imidazo [1,2-a]pyridin-3-yl)methylene)benzenesulfonohydrazide;

(E)-5-Fluoro-N,2-dimethyl-N-((6-(pyrimidin-5-ypimidazo[1,2-a]pyridin-3-yl)methylene)benzenesulfonohydrazide;

(E)-N-benzyl-1-methyl-2-((6-(pyridin-3-yl)imidazo[1,2-a]pyridin-3-yl)methylene)hydrazinecarboxamide;

(E)-1-methyl-2-((6-(pyridin-3-yl)imidazo[1,2-a]pyridin-3-yl)methylene)-N-p-tolylhydrazinecarboxamide;

(E)-N-(2-fluoro-5-methylphenyl)-1-methyl-2-((6-(pyridin-3-yl)imidazo[1,2-a]pyridin-3-yl)methylene)hydrazinecarboxamide;

(E)-N-(5-fluoro-2-methylphenyl)-1-methyl-2-((6-(pyridin-3-yl)imidazo[1,2-a]pyridin-3-yl)methylene)hydrazinecarboxamide;

N-benzyl-2-((6-bromoimidazo[1,2-a]pyridin-3-yl)methylene)-1-methyl hydrazinecarboxamide;

(6-bromoimidazo[1,2-a]pyridin-3-yl)methylene)-N-(2-fluoro-5-methylphenyl)-1-methylhydrazinecarboxamide;

(6-bromoimidazo[1,2-a]pyridin-3-yl)methylene)-N-(5-fluoro-2-methlphenyl)-1-methylhydrazinecarboxamide;

(E)-1-methyl-N-(2-morpholinoethyl)-2-((6-(pyridin-3-yl)imidazo[1,2-a]pyridin-3-yl)methylene)hydrazinecarbothioamide;

(E)-N-(4-cyanophenyl)-1-methyl-2-((6-(pyridin-3-yl)imidazo[1,2-a]pyridin-3-yl)methylene)hydrazinecarbothioamide;

(E)-N-(4-methoxyphenyl)-1-methyl-2-((6-(pyridin-3-yl)imidazo[1,2-a]pyridin-3-yl)methylene)hydrazinecarbothioamide;

2-((6-bromoimidazo[1,2-a]pyridin-3-yl)methylene)-1-methyl-N-(2-morpholinoethyl)hydrazinecarbothioamide;

2-((6-bromoimidazo[1,2-a]pyridin-3-yl)methylene)-1-methyl-N-(4-(trifluoromethyl)phenyl)hydrazinecarbothioamide; or a stereoisomer, tautomer, N-oxide or a pharmaceutically-acceptable salt thereof.

13. A pharmaceutical composition, comprising a therapeutically effective amount of a compound of formula (I) according claim 1 or a pharmaceutically acceptable salt thereof and a pharmaceutically acceptable excipient or carrier.

14. A method for the treatment of a disease mediated by PI3K (phosphatidylinositol-3-kinase) or mTOR (mammalian target of rapamycin) or STAT3(Signal transducer and activator of transcription 3) or a combination thereof, comprising, administering to a mammal in need thereof a therapeutically effective amount of a compound of formula (I) according to claim 1 or a pharmaceutically acceptable salt thereof, wherein the disease is cancer is selected from the group consisting of small-cell-lung cancer, non-small-cell lung cancer, prostate cancer, ovarian cancer, colorectal cancer, pancreatic cancer, breast cancer and glioblastoma.

15. A method for the treatment of a disease mediated by TNF-α or IL-6, comprising administering to a mammal in need thereof a therapeutically effective amount of a compound of formula (I) according to claim 1 or a pharmaceutically acceptable salt thereof, wherein the disease mediated by TNF-α or IL-6 is selected from the group consisting of psoriasis, inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, atherosclerosis, ulcerative colitis, and ankylosing spondylitis.

16. The method according to claim 15, wherein the disease mediated by TNF-α or IL-6is selected from the group consisting of rheumatoid arthritis, Crohn's disease, ulcerative colitis, psoriasis and atherosclerosis.

17. A process for the preparation of a compound of formula (I)

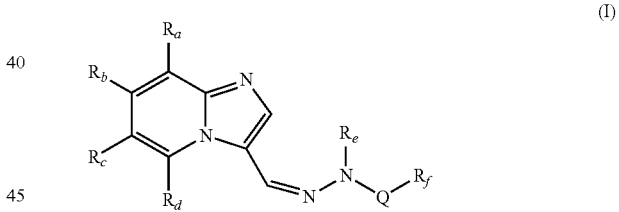

wherein, Q is $SO_2$; $R_a$, $R_b$ and $R_d$ are hydrogen or methyl; $R_c$, $R_e$ and $R_f$ are as defined for formula (I) in claim 1, comprising refluxing a compound of formula (3)

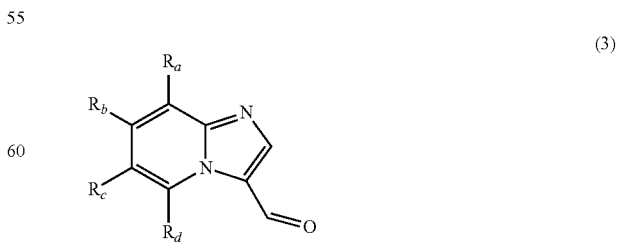

with a compound of formula $H_2N-NH-R_e$ in presence of an alcoholic solvent followed by reacting with a compound of formula $R_fSO_2X$, wherein Q is $SO_2$; X is halogen, $R_a$, $R_b$ and $R_d$ are independently hydrogen or methyl, $R_c$, $R_e$ and $R_f$ are as defined above for formula (I) in presence of pyridine as a base;

optionally converting the resulting compound into a pharmaceutically acceptable salt.

18. A process for the preparation of a compound of formula (I)

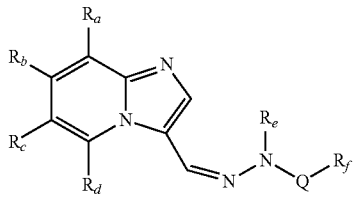
(I)

wherein, Q is —C(O)NH or —C(S)NH; $R_a$, $R_b$ and $R_d$ are independently hydrogen or methyl, $R_c$, $R_e$ and $R_f$ are as defined for formula (I) in claim 1, which comprises, refluxing a compound of formula (3)

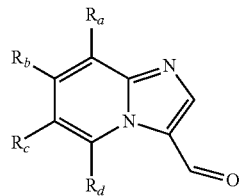
(3)

with a compound of formula $H_2N$—NH—$R_e$ in presence of an alcoholic solvent followed by reacting with a compound of formula O=C=N=$R_f$ or S=C=N=$R_f$, wherein $R_a$, $R_b$ and $R_d$ are hydrogen or methyl, $R_c$, $R_e$ and $R_f$ are as defined above for formula (I);

optionally converting the resulting compound into a pharmaceutically acceptable salt.

* * * * *